United States Patent
York et al.

(10) Patent No.: US 11,193,057 B2
(45) Date of Patent: Dec. 7, 2021

(54) FLUORESCENT PARTICLES

(71) Applicant: LIFE TECHNOLOGIES CORPORATION, Carlsbad, CA (US)

(72) Inventors: Adam York, Eugene, OR (US); Eric Welch, Eugene, OR (US); Kyle Gee, Springfield, OR (US); Xin Wang, Eugene, OR (US); Robert Aggeler, Eugene, OR (US); Yi-Zhen Hu, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 157 days.

(21) Appl. No.: 16/324,730

(22) PCT Filed: Aug. 24, 2017

(86) PCT No.: PCT/US2017/048467
§ 371 (c)(1),
(2) Date: Feb. 11, 2019

(87) PCT Pub. No.: WO2018/044688
PCT Pub. Date: Mar. 8, 2018

(65) Prior Publication Data
US 2019/0194532 A1    Jun. 27, 2019

Related U.S. Application Data

(60) Provisional application No. 62/380,874, filed on Aug. 29, 2016.

(51) Int. Cl.
*C09K 11/02* (2006.01)
*C09K 11/06* (2006.01)
(Continued)

(52) U.S. Cl.
CPC ............ *C09K 11/025* (2013.01); *C09B 68/41* (2013.01); *C09K 11/06* (2013.01);
(Continued)

(58) Field of Classification Search
CPC ............ G01N 33/5005; G01N 33/582; G01N 33/533; H04L 12/1822; H04L 12/1895;
(Continued)

(56) References Cited

U.S. PATENT DOCUMENTS 6,838,289 B2    1/2005   Bell et al.
8,067,506 B2 *  11/2011  Chen .................... C08J 3/03
                                                525/450
(Continued)

FOREIGN PATENT DOCUMENTS

WO    WO-2007027159 A1    3/2007

OTHER PUBLICATIONS

Reisch et al. Fluorescent polymer nanoparticles based on dyes: seeking brighter tools for bioimaging. Small. 2016, vol. 12, No. 15, pp. 1968-1992. (Year: 2016).*

(Continued)

*Primary Examiner* — Shafiqul Haq

(57) ABSTRACT

Water-soluble, fluorescent particles and compositions, kits, and methods of making and using such particles are disclosed. Processes for preparing fluorescent particles and for (Continued)

controlling the size, polydispersity and optical properties of such particles also are provided.

16 Claims, 12 Drawing Sheets

(51) Int. Cl.
| | | |
|---|---|---|
| *G01N 33/50* | (2006.01) | |
| *G01N 33/58* | (2006.01) | |
| *H04L 12/18* | (2006.01) | |
| *C09B 67/00* | (2006.01) | |
| *G01N 33/533* | (2006.01) | |
| *H04L 29/08* | (2006.01) | |

(52) U.S. Cl.
CPC ....... *G01N 33/5005* (2013.01); *G01N 33/533* (2013.01); *G01N 33/582* (2013.01); *H04L 12/1822* (2013.01); *H04L 12/1827* (2013.01); *H04L 12/1895* (2013.01); *C09K 2211/1416* (2013.01); *C09K 2211/1483* (2013.01); *H04L 67/10* (2013.01)

(58) Field of Classification Search
CPC ..... H04L 12/1827; H04L 67/10; C09B 68/41; C09K 2211/1416; C09K 11/025; C09K 11/06; C09K 2211/1483
See application file for complete search history.

(56) References Cited

U.S. PATENT DOCUMENTS

| | | |
|---|---|---|
| 2008/0070319 A1 | 3/2008 | Makino |
| 2008/0242806 A1* | 10/2008 | Chen .................... G01N 33/582 |
| | | 525/450 |
| 2012/0282632 A1 | 11/2012 | Chiu et al. |
| 2015/0140549 A1 | 5/2015 | Mehrpouyan et al. |

OTHER PUBLICATIONS

Grazon et al. Ultrabright BODIPY-tagged polystyrene nanoparticles: study of concentration effect on photophysical properties. J. Phys. Chem. C 2014, vol. 118, p. 13945-13952. (Year: 2014).*

Grazon et al. Fluorescent core-shell nanoparticles and nanocaptules using comb-like macromolecular RAFT agents: synthesis and functionalizaiton thereof. Polym. Chem. 2016, vol. 7, pp. 4272-4283. (Year: 2016).*

Grazon et al. Ultrabright fluorescent polymeric nanoparticles made from a new family of BODIPY monomers. Macromolecules 2013, vol. 46, pp. 5167-5176. (Year: 2013).*

International Preliminary Reporton Patentability for International Application No. PCT/US2017/048467 dated Mar. 5, 2019, 10 pages.

International Search Report and Written Opinion for Application No. PCT/US2017/048467, dated Dec. 15, 2017, 15 pages.

* cited by examiner

FLUORESCENT PARTICLES

FIELD

Fluorescent particles and methods for their preparation and use are provided. Processes and devices for preparing sub-micron sized fluorescent particles and for controlling the size, polydispersity and optical properties of such particles also are provided.

BACKGROUND

Semiconducting polymers are an important class of materials that can conduct charge and exhibit photoluminescence with high quantum efficiency. Due to their exceptional optical and electrical properties, semiconducting polymers have been used in optoelectronic devices and display technologies. Water-soluble derivatives of semiconducting polymers have been implemented as fluorescent probes in a variety of biological applications (e.g., flow cytometry, immunoassays, ELISA assays and molecular imaging). Semiconducting polymers also have been used in the preparation of water-soluble fluorescent nanoparticles. Water-soluble, fluorescent nanoparticles can include a hydrophobic, fluorescent polymer encapsulated by an amphiphilic molecule. This amphiphilic molecule can be attached to a ligand (e.g., nucleic acid, peptide or protein, an enzyme substrate, biotin or streptavidin) that can interact with a specific target molecule (e.g., a molecule that binds to or specifically recognizes the ligand, such as a cell surface receptor, antibody, antigen or nucleic acid). Due to their high absorption cross-section, fluorescent nanoparticles can be exceptionally bright and when properly formulated exhibit minimal aggregation and self-quenching in biological applications. These properties impart fluorescent nanoparticles with a distinct advantage over existing technologies utilizing water-soluble derivatives of conjugated polymers.

Fluorescent nanoparticles can be prepared using various methods, including nanoprecipitation, emulsion formation and condensation methods. Existing processes attempt to control the optical properties and the diameter of the nanoparticles by adjusting the ratio of the fluorescent polymers and amphiphilic molecules during the process of forming the particles. Despite on-going efforts to develop water-soluble, fluorescent nanoparticles, however, large-scale production of sub-micron sized fluorescent particles with robust physical and optical properties and low polydispersity remains a challenge. Thus, there exists a need for improved processes and devices for preparing narrowly dispersed, bright, thermally and optically stable, fluorescent nanoparticles that are colloidally stable in aqueous media and exhibit favorable optical properties (e.g., high extinction coefficient and quantum yield and efficient energy transfer), even under intense irradiation. In addition, there exists a need for bright, fluorescent particles that present surface reactive groups for covalent attachment of ligands and that can be precisely tuned to absorb and emit light at specific wavelengths ranging from, e.g., the violet to red region of the electromagnetic spectrum. Further, fluorescent nanoparticle technologies have yet to be optimized for use in complicated multiplex assays (e.g., flow cytometry). For example, flow cytometry assays utilizing multiple lasers are particularly prone to problems associated with background fluorescence (also referred to as "spillover"). This issue is particularly pronounced when fluorescent particles having different excitation and emission profiles are utilized in the detection of multiple types of cells. Thus, bright, fluorescent particles with narrow band absorption and emission profiles are needed that do not contribute to background fluorescence and spillover problems, such as are frequently encountered in multiplex fluorescence applications (e.g., flow cytometry).

SUMMARY

Provided herein are novel fluorescent particles, compositions, kits, and methods for preparing and using these particles and compositions. The fluorescent particles described herein are soluble in aqueous environments (e.g., water or buffer). Water-soluble, fluorescent particles are ideally suited for use in various types of biological applications and emit bright, visible light with high quantum efficiency upon excitation at an appropriate wavelength of light (e.g., resulting from irradiation with a laser). The disclosed particles are photostable and do not dim significantly when dissolved in an aqueous medium (e.g., deionized water, borate buffer, carbonate buffer, or phosphate buffer). The disclosed particles also resist oxidative degradation or aggregation after exposure to elevated temperatures. Because the fluorescent particles resist aggregation, the particles do not suffer from aggregation-induced quenching of fluorescence. In addition to thermal stability, the fluorescent particles exhibit minimal shifts in emission peak that can result from high intensity and/or prolonged irradiation, making them particularly suitable for use in biological applications (e.g., cell imaging by fluorescence microscopy and flow cytometry). The disclosed fluorescent particles also exhibit minimal background fluorescence, which is especially important when the particles are implemented in multi-color flow cytometry experiments. These types of experiments can use particles that include sets of fluorophores that are capable of energy transfer (e.g., FRET). Highly efficient energy transfer between donor and acceptor fluorophores can be achieved using the particles disclosed herein by selecting materials with compatible properties to optimize packing of the fluorophores within a polymer matrix. For example, energy transfer efficiencies between donor and acceptor fluorophores of greater than 90% can be achieved for particles disclosed herein containing as little as 1 mol % acceptor fluorophore.

In one aspect, the water-dispersible fluorescent particles described herein include an internal hydrophobic region comprising a mixture of a first hydrophobic polymer and a second hydrophobic polymer, wherein the first hydrophobic polymer is fluorescent and has a first solubility parameter and the second hydrophobic polymer is non-fluorescent and has a second solubility parameter, and wherein the first and second solubility parameters differ by less than 1 $cal^{1/2}$ $cm^{-3/2}$; and an external region encapsulating the internal hydrophobic region, wherein the external region comprises an amphiphilic polymer, wherein the amphiphilic polymer comprises at least one hydrophobic segment embedded in the internal hydrophobic region and at least one hydrophilic segment that renders the particle dispersible in water. In certain embodiments, the internal hydrophobic region comprises a mixture of one or more first hydrophobic polymers and one or more second hydrophobic polymers, wherein the first hydrophobic polymer is fluorescent and has a first solubility parameter and the second hydrophobic polymer is non-fluorescent and has a second solubility parameter, and wherein the first and second solubility parameters differ by less than 1 $cal^{1/2}$ $cm^{-3/2}$; and an external region encapsulating the internal hydrophobic region, wherein the external region comprises one or more amphiphilic polymers, wherein each of the one or more amphiphilic polymers comprises at least one hydrophobic segment embedded in the internal hydrophobic region and at least one hydrophilic segment that renders the particle dispersible in water.

Water-dispersible, fluorescent particles provided herein can have a mean hydrodynamic diameter of about 20 nm to about 100 nm as measured by dynamic light scattering (DLS). In some embodiments, the mean hydrodynamic diameter of the particle is about 35 nm to about 60 nm as measured by DLS. Water-dispersible, fluorescent particles disclosed herein can include a hydrophobic internal region and an external region encapsulating the hydrophobic internal region. The hydrophobic internal region can include a mixture of one or more fluorescent, first hydrophobic polymers and one or more non-fluorescent, second hydrophobic polymers, wherein the solubility parameters of the first and second hydrophobic polymers differ by less than 1 $cal^{1/2}$ $cm^{-3/2}$. For example, the mixture can be a homogeneous blend of the one or more first and second hydrophobic polymers. In certain embodiments, the solubility parameters of the first and second hydrophobic polymers can differ by less than 0.5 $cal^{1/2}$ $cm.^{-3/2}$. The first and/or second hydrophobic polymer(s) can have a solubility parameter from about 8.0 $cal^{1/2}$ $cm^{-3/2}$ to 10.0 $cal^{1/2}$ $cm^{-3/2}$. The fluorescent polymer(s) can have a number average molecular weight ($M_n$) of about 10,000 g/mol to about 90,000 g/mol. For example, the fluorescent polymer(s) can have a number average molecular weight ($M_n$) of about 20,000 g/mol to about 40,000 g/mol. The non-fluorescent polymer(s) can have a number average molecular weight ($M_n$) of about 1000 g/mol to about 10,000 g/mol. For example, the non-fluorescent polymer(s) can have a number average molecular weight ($M_n$) of about 1200 g/mol to about 3000 g/mol. The weight ratio of the one or more first fluorescent, hydrophobic polymer to the one or more second non-fluorescent hydrophobic polymer in the internal region can be about 1:10 to about 10:1. In some embodiments, the weight of the one or more fluorescent polymer relative to the sum total weight of first and second non-fluorescent hydrophobic polymers in the internal region can be about 50% to 99%. In some embodiments, the weight of the fluorescent and non-fluorescent hydrophobic polymers within the internal region relative to the total weight of the particle is about 20% to about 80%. In other embodiments, the weight of the fluorescent and non-fluorescent hydrophobic polymers within the internal region relative to the total weight of the particle is about 70% to 95%.

The hydrophobic internal region of the fluorescent particles provided herein can include one or more first hydrophobic fluorescent polymers. The hydrophobic, fluorescent polymer can include a non-fluorescent, hydrophobic polymer that is linked to one or more organic dyes, wherein the non-fluorescent hydrophobic polymer is optionally the same as the second hydrophobic polymer linked to one or more organic dyes. Alternatively, the hydrophobic fluorescent polymer(s) can include a fluorescent, hydrophobic polymer that is linked to one or more organic dyes. The organic dye can be selected from a boron dipyrromethenes (4,4-difluoro-4-bora-3a,4a-diaza-s-indacene, BODIPY dyes), cyanines, xanthenes, sulfonated pyrenes, rhodamines, coumarins, and derivatives thereof. For example, the organic dye can be selected from BODIPY dyes, coumarins (e.g., PACIFIC BLUE, PACIFIC GREEN, PACIFIC ORANGE), rhodamines, fluorescein, aminofluorescein, carboxyfluorescein, aminorhodamine, carboxyrhodamine, cyanine dyes (e.g., cyanine 2, cyanine 3, cyanine 3.5, cyanine 5, cyanine 5.5, cyanine 7), Nile red, ALEXA FLUOR 405, ALEXA FLUOR 594, ALEXA FLUOR 633, ALEXA FLUOR 647, ALEXA FLUOR 700, xanthenes and sulfonated xanthenes (e.g., ALEXA FLUOR 594, ALEXA FLUOR 633, ALEXA FLUOR 647, ALEXA FLUOR 700), silicon rhodamines, and derivatives and combinations thereof.

The one or more first hydrophobic fluorescent polymer can be a conjugated polymer. In some embodiments, the one or more first hydrophobic fluorescent polymer is a semiconducting polymer. For example, the one or more first hydrophobic fluorescent polymer can include a monomer residue having a structure of the formula, —[Ar]n-, wherein Ar is an aryl or heteroaryl and is optionally substituted with one or more optionally substituted substituents selected from halogen, hydroxyl, C1-C12 alkyl, C2-C12 alkene, C2-C12 alkyne, C3-C12 cycloalkyl, C1-C12 haloalkyl, C1-C12 alkoxy, C2-C18(hetero)aryloxy, and C2-C18(hetero)arylamino. The one or more first hydrophobic polymer can include a component group selected from optionally substituted arylene, heteroarylene, arylene vinylene, heteroarylene vinylene, arylene ethylene, heteroarylene, ethylene, phenylene, thienylene, fluorenylene, spirobifluorenylene, indenofluorenylene, pyridylene, bipyridylene, carbazoylene, indenocarbazolylene, benzothiazolylene, and oxadiazolylene. The one or more first hydrophobic polymer can be selected from the group consisting of polyphenylene-ether, polyarylenevinylenes, polyaryleneethynylene, dibenzosilole polymers, fluorene polymers, phenylene vinylene polymers, phenylene polymers, benzothiazole polymers, thiophene polymers, carbazole fluorene polymers, boron-dipyrromethene polymers, and derivatives and copolymers thereof. The one or more first hydrophobic polymer can be selected from poly(9,9-dihexylfluorenyl-2,7-diyl) (PDHF), poly(9,9-dioctylfluorenyl-2,7-diyl) (PFO), (poly{9,9-dioctyl-2,7-divinylene-fluorenylene}-alt-co-{2-methoxy-5-(2-ethylhexyloxy)-1,4-phenylene}] (PFPV), poly[(9,9-dioctylfluorenyl-2,7-diyl)-co-(4,7-di-2-thienyl-2,1,3-benzothiadiazole)] (PFTBT), poly[(9,9-dioctylfluorenyl-2,7-diyl)-9-co-(4,7-di-2-thienyl-2,1,3-benzothiadiazole)] (PF-0.1TBT)), poly[(9,9-dioctylfluorenyl-2,7-diyl)-alt-co-(1,4-benzo-(2,1',3)-thiadiazole)] (PFBT), poly[(9,9-di(2-ethylhexyl)fluorenyl-2,7-diyl)-alt-2,5-difluoro-1,4-benzene] (PFDFB), poly[(9,9-di(2-ethylhexyl)fluorenyl-2,7-diyl)-alt-1,4-benzene] (PFB), poly[(9,9-di(2-ethylhexyl)fluorenyl-2,7-diyl)-alt-4,4'-diphenyl-5,6-difluoro-1,4-benzo-(2,1,3)-thiadiazole] (PFDPDFBT), poly[(9,9-di(2-ethylhexyl)fluorenyl-2,7-diyl)-alt-4,4'-diphenyl-1,4-benzo-(2,1,3)-thiadiazole] (PFDPBT), (poly[(9,9-di(2-ethylhexyl)fluorenyl-2,7-diyl)-alt-4,4'-diphenyl-5-fluoro-1,4-benzo-(2,1,3)-thiadiazole] (PFDPFBT), poly[2-methoxy-5-(2-ethylhexyloxy)-1,4-phenylenevinylene] (MEH-PPV)), poly[2-methoxy-5-(2-ethylhexyloxy)-1,4-(1-cyanovinylene-1,4-phenylene)] (CN-PPV), poly(BODIPY), and derivatives and combinations thereof. The one or more first hydrophobic polymer can be selected from poly(9,9-dihexylfluorenyl-2,7-diyl) (PDHF), poly(9,9-dioctylfluorenyl-2,7-diyl) (PFO)), (poly[{9,9-dioctyl-2,7-divinylene-fluorenylene}-alt-co-{2-methoxy-5-(2-ethylhexyloxy)-1,4-phenylene}] (PFPV), poly[(9,9-dioctylfluorenyl-2,7-diyl)-co-(4,7-di-2-thienyl-2,1,3-benzothiadiazole)] (PFTBT), poly[(9,9-dioctylfluorenyl-2,7-diyl)-alt-co-(1,4-benzo-(2,1',3)-thiadiazole)] (PFBT), poly[2-methoxy-5-(2-ethylhexyloxy)-1,4-phenylenevinylene] (MEH-PPV)), poly(BODIPY) and derivatives and combinations thereof. In certain embodiments, the one or more first hydrophobic polymer can be selected from poly(9,9-dioctylfluorenyl-2,7-diyl) (PFO)), poly[(9,9-dioctylfluorenyl-2,7-diyl)-alt-co-(1,4-benzo-(2,1',3)-thiadiazole)] (PFBT), poly(BODIPY) and derivatives and combinations thereof. For example, the one or more first hydrophobic polymer can be polyfluorene or polyfluorene-co-benzothiazole or a copolymer of polyfluorene and polyfluorene-co-PBT, wherein the copolymer includes about 2 mol % or less of PBT.

The hydrophobic internal region of the fluorescent particles provided herein can include one or more second, non-fluorescent, hydrophobic polymers. Examples of non-fluorescent, hydrophobic polymer(s) includes poly(alkyl methacrylates), poly(alkyl acrylates), poly(alkyl methacrylamides), poly(alkyl acrylamides), polystyrenes, including, e.g., substituted polystyrenes such as alkyl substituted polystyrenes, wherein alkyl is selected from $C_{1-10}$ alkyl (e.g., methyl-dodecyl)), polylactic acid, polycaprolactone, and poly(vinyl acetate).

The water-dispersible fluorescent particles disclosed herein further include an external region encapsulating the hydrophobic internal region that includes one or more amphiphilic polymers, each including at least one hydrophobic segment embedded in the hydrophobic internal region of the particle and at least one hydrophilic segment that renders the particle dispersible in water. The amphiphilic polymer(s) can have a number average molecular weight ($M_n$) of about 2000 g/mol to about 25,000 g/mol. For example, the amphiphilic polymer(s) can have a number average molecular weight ($M_n$) of about 3500 g/mol to about 10,000 g/mol.

The solubility parameter of the at least one hydrophobic segment of the one or more amphiphilic polymers typically differs from the solubility parameter of the one or more non-fluorescent, hydrophobic polymers by less than 1 $cal^{1/2}$ $cm^{-3/2}$. Similar solubility parameters can be achieved when the hydrophobic segment of the amphiphilic polymer includes one or more monomer units having the same composition as those used in the first hydrophobic polymer and/or the second hydrophobic polymer. For example, the hydrophobic segment of the one or more amphiphilic polymer can include a group selected from polystyrene, alkyl methacrylates, alkyl acrylates, alkyl methacrylamides, alkyl acrylamides, alkyl substituted polystyrene, wherein alkyl is selected from C1-10 alkyl (e.g., methyl-dodecyl), polylactic acid, polycaprolactone, and poly(vinyl acetate). The hydrophilic segment of the one or more amphiphilic polymer can include a water-soluble polymer, such as, e.g., PEO, poly (acrylamide), poly(N-2-hydroxypropylmethacrylamide, poly(N,N-dimethylacrylamide), poly(N-methyl methacrylamide), and polyzwitterions, polyvinylpyrrolidone (PVP), and polyvinyl alcohol (PVA). Additional examples of water-soluble polymers include neutral (i.e., uncharged) polymers, such as poly(acrylamide), poly(methacrylamide), poly(m-ethyl vinyl ether), poly(vinyl pyrrolidone) (PVP), polyvinyl alcohol (PVA), poly(2-ethyl-2-oxazoline), and poly(2-methyl-2-oxazoline). Exemplary acrylamide and methacrylamide-based polymers can include residues of monomer units, such as, e.g., N—R acrylamide or N—R methacrylamide, wherein R is methyl, ethyl, propyl, isopropyl or H; N,N-dimethylacrylamide, N,N-dimethylmethacrylamide, N,N-diethylacrylamide, N, N diethylmethacrylamide, N-2-hydroxypropyl methacrylamide), or a combination of these monomer units. In certain embodiments, the uncharged, water-soluble polymer is poly(N-methyl methacrylamide) (PMMAm). Alternatively, the water-soluble polymer can be a charged polymer (e.g., a polyelectrolyte). Exemplary charged, water-soluble polymers include polyacrylic acid, polymethacrylic acid, poly(diallyldimethylammonium chloride), poly(sodium-4-styrenesulfonate), poly(ethyleneimine), poly(N,N-dimethylaminoethyl acrylate), poly(N,N-diethylethylamino acrylate), poly(allylamine), poly[bis(2-chloroethyl)ether-co-1,3-bis[3-(dimethylamino)propyl] urea]; or poly(vinylsulfonic acid, sodium salt).

The hydrophilic segment of the one or more amphiphilic polymer can be selected from vinyl polymers (e.g., poly (sodium 4-styrenesulfonate)), acrylic polymers (CR(X)—CH2), where X is H, low chain alkyl (C1-C2), or CN and R is $COOR^1$ (acrylates and methacrylates) or $CONR^1$ (acrylamides and methacrylamides) (e.g., poly(N,N-dimethylacrylamide)). $R^1$ and $R^2$ can be independently H, low chain alkyl alcohols (e.g. poly(N-2-hydroxypropyl methacrylamide), poly(2-hydroxyethyl methacrylate), poly (2-ethyl-2-oxazoline), polyzwitterions, and combinations thereof. In some embodiments, the hydrophilic segment of the one or more amphiphilic polymer is a copolymer of an acrylate monomer with an acrylamide or styrene monomer. In some embodiments, the hydrophilic segment of the one or more amphiphilic polymer can be a copolymer of a polyethylene glycol or polyethylene oxide monomer with an acrylamide or styrene monomer. In some embodiments, the one or more amphiphilic polymer includes a polyethylene-oxide (PEO) segment. A polymer that includes a polyethylene-oxide segment is referred to herein interchangeably as polyethylene glycol (PEG). In some embodiments, the one or more amphiphilic polymer is polylactic-acid-PEO (PLA-PEO) or polystyrene-PEO (PS-PEO).

Also provided herein is a fluorophore that is capable of transferring energy to an organic dye. Thus, in another aspect, a fluorophore is provided herein, including a hydrophobic, semiconducting, fluorescent polymer including a first fluorescent polymer unit and a second fluorescent polymer unit linked to an organic dye, as disclosed herein, wherein the fluorescent polymer includes 5 mol % or less of the second fluorescent polymer unit, wherein upon excitation at an appropriate wavelength of light, the fluorescent polymer transfers energy to the organic dye, such that the organic dye emits light at a second wavelength. In certain embodiments, the organic dye is a BODIPY dye. The first fluorescent polymer unit can include, e.g., polyfluorene or a derivative thereof. The fluorescent polymer unit can include at least 93 mol % of the first fluorescent polymer unit. The second fluorescent polymer unit can include polyfluorene or a derivative thereof, and the polyfluorene or derivative thereof can include a pendant group that is linked to the organic dye. In some embodiments, the fluorophore further includes 5 mol % or less of a third fluorescent polymer unit. Examples of third fluorescent polymer units include, without limitation, poly[(9,9-dioctylfluorenyl-2,7-diyl)-alt-co-(1,4-benzo-(2,1',3)-thiadiazole)] (PFBT), poly[(9,9-dioctylfluorenyl-2,7-diyl)-alt-co-(4,7-di(thiophen-2-yl)benzo[c][1,2,5]thiadiazole)] (PBT2T), poly[(9,9-dioctylfluorenyl-2,7-diyl)-alt-co-(bithiophene)] (PF2T), poly[3-hexylthiophene-2,5-diyl] (PHT), poly[(9,9-dioctyl-2,7-divinylenefluorenylene)-alt-co-(9,10-anthracene)] (PVFA), poly[2,6-(4,4-bis-(2-ethylhexyl)-4H-cyclopenta[2,1-B; 3,4-B'] dithiophene)-alt-4,7(2,1,3-benzothiadiazole)] (PCPTBT), poly[2-methoxy-5-(2-ethylhexyloxy)-1,4-phenylenevinylene] (MEH-PPV)), poly[2-methoxy-5-(2-ethylhexyloxy)-1,4-(1-cyanovinylene-1,4-phenylene)] (CN-PPV), poly(BODIPY) or a derivative thereof.

In yet another aspect, a fluorescent particle is provided that includes a fluorophore, as disclosed herein, wherein upon excitation at an appropriate wavelength of light, the fluorescent polymer transfers energy to the organic dye, such that the organic dye emits light at a second wavelength, the efficiency of energy transfer is greater than 80%.

In yet another aspect, a water-dispersible, fluorescent particle is provided including: a hydrophobic internal region, including a mixture of a fluorophore, as disclosed herein, and one or more non-fluorescent, hydrophobic polymers, as disclosed herein. The particle can include more than one hydrophobic polymer, in which case the solubility parameters of the first and second hydrophobic polymers differ by less than 1 $cal^{1/2}$ $cm^{-3/2}$. The particle can further include an external region encapsulating the hydrophobic internal region that includes one or more amphiphilic polymers, as disclosed herein, each including at least one hydrophobic segment embedded in the hydrophobic internal region of the particle and at least one hydrophilic segment that renders the particle dispersible in water.

Also provided herein are methods for packaging of fluorophores within the hydrophobic core of a water-dispersible particle that includes reactive surface groups in a single processing step. Thus, provided herein are flash nanoprecipitation methods for preparing fluorescent nanoparticles. Thus, in yet another aspect, a method for preparing the water-dispersible, fluorescent particles, as disclosed herein, is provided, including: dissolving one or more amphiphilic polymers and one or more fluorescent, first hydrophobic polymers and one or more non-fluorescent, second hydrophobic polymers in an organic solvent to provide a first solution, wherein the weight of fluorescent polymer relative to the total weight of the hydrophobic polymers in the polymer solution can be 95% or less (e.g., 70% to 95%; or 20% to 80%). The weight of fluorescent polymer relative to the total weight of all hydrophobic polymers in the particle and the hydrophobic segments of the amphiphilic polymer in the polymer solution can be 60% or less (e.g., 45 wt. % or less). The method further includes introducing the first solution into water or an aqueous solution including a buffering agent or salt to provide sub-micron sized water-dispersible, fluorescent particles. In some embodiments, the first solution is introduced at a flow rate of 10 m/sec or greater to flash precipitate fluorescent particles having a mean intensity hydrodynamic diameter about 20 nm to about 100 nm, as measured by DLS.

Also provided herein are conjugates including a water-dispersible, fluorescent particle, as disclosed herein, linked to a ligand. The ligand can be a biomolecule such as, for example, an amino acid, peptide, protein, polysaccharide, nucleoside, nucleotide, nucleic acid base, oligonucleotide, or a nucleic acid polymer. Representative examples of ligands include, without limitation, an antibody or fragment thereof, a fluorescent protein, and a metal binding protein, an enzyme, an enzyme inhibitor, an enzyme substrate, avidin or a derivative thereof, a hapten, psoralen, a drug, a hormone, a lipid, a lipid assembly, a synthetic polymer, a microparticle, a biological cell, a virus, a biotin, a dextran, a growth factor, a lectin, a lipopolysaccharide, a microorganism, a metal chelating moiety, and a peptide toxin. A conjugate, as disclosed herein, can further include a target molecule, wherein the ligand is associated with the target molecule.

In yet another aspect, a composition is provided, including a particle or conjugate, as disclosed herein; and an aqueous medium, wherein the particle or conjugate is dispersed in the aqueous medium.

In yet another aspect, a cell is provided, including a particle or conjugate, as disclosed herein. The particle or conjugate can reside within the cytoplasm or nucleus of the cell, on or within a portion of the cell membrane, or can be associated with the surface of the cell.

The fluorescent particles and conjugates disclosed herein can be used in various life sciences applications (e.g., cell labeling, imaging and flow cytometry). Thus, in yet another aspect is provided a method of labeling cells, including contacting a cell with the particle or conjugate, as disclosed herein, for a time sufficient to allow the particle to bind to the surface of the cell or enter into the cell. In some embodiments, the method includes contacting the cell with a conjugate, as disclosed herein, wherein the affinity molecule binds to a target molecule on the surface of the cell.

In yet another aspect, a method for detecting a target molecule in a sample is provided, including: providing a sample that is suspected of containing a target molecule; contacting the sample with a conjugate, as disclose herein, wherein the ligand is capable of interacting with the target molecule in the sample, under conditions whereby the ligand can bind to the target molecule, if present; exciting the sample with light having an appropriate wavelength; and detecting the light emitted from the particle.

Further provided herein are kits for using fluorescent particles, as disclosed herein, in various life sciences applications. Thus, in yet another aspect, a kit for labeling cells is provided, including: a conjugate, as disclosed herein, wherein the ligand is capable of binding to a target molecule that is in or on the surface of a cell; and instructions for labeling the cell with the conjugate and detecting the labeled cell. In yet another aspect, a kit is provided for detecting a target molecule in a sample is provided, including: a conjugate, as disclosed herein, wherein the ligand is capable of binding to a target molecule in a sample; and instructions for binding the ligand to the target molecule, if present, and detecting the light emitted from the particle.

DESCRIPTION OF THE FIGURES

The following figures form part of the present specification and are included to further demonstrate certain aspects of the present invention. The invention may be better understood by reference to one or more of these figures in combination with the detailed description of specific embodiments presented herein.

DETAILED DESCRIPTION

Figure 1:
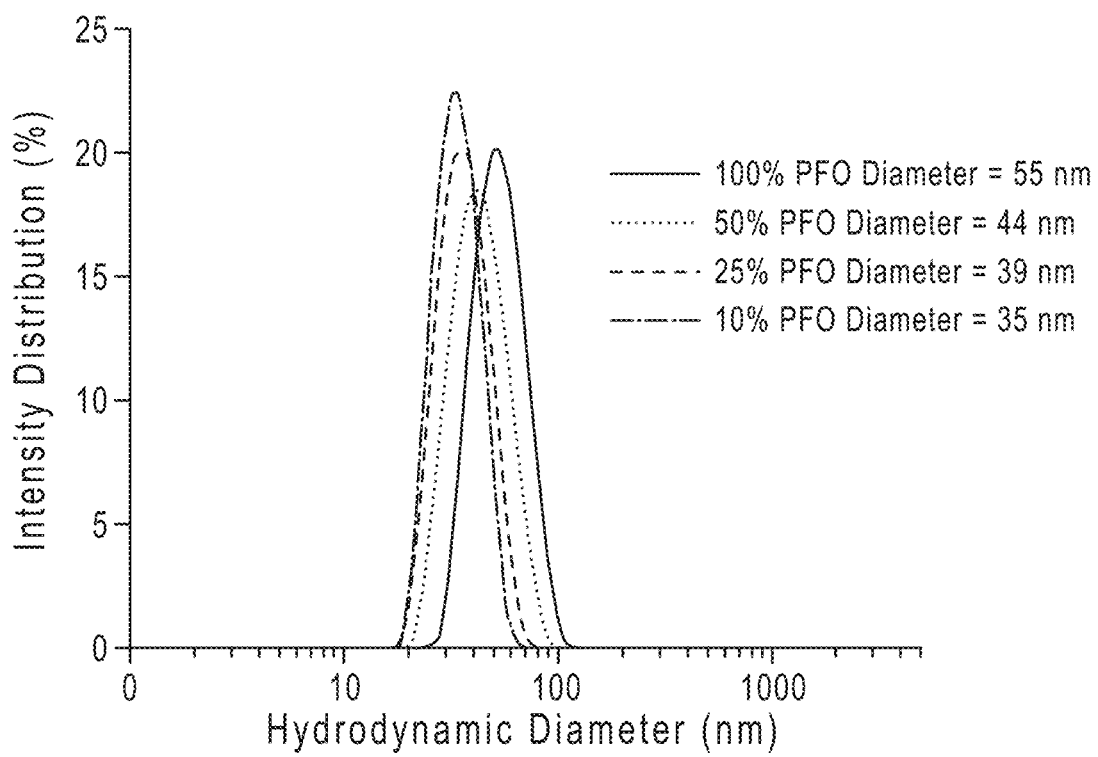
FIG. 1 is a plot showing the change in particle size and fluorescent intensity distribution with different amounts of hydrophobic polymer in the NP core.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, the term "about", when used to describe a numerical value, shall encompass a range up to ±15% of that numerical value, unless the context clearly dictates otherwise.

While compositions and methods are described in terms of "comprising" various components or steps (interpreted as meaning "including, but not limited to"), the compositions and methods can also "consist essentially of" or "consist of" the various components and steps, such terminology should be interpreted as defining essentially closed-member groups.

"Polymer" as used herein refers to a substance composed of molecules that include multiple repetitions of one or more types of monomer units linked to each other in amounts sufficient to provide a set of properties that does not vary substantially upon addition or removal of one or a few monomer units. A polymer includes a backbone (i.e., the connected chain of atoms that span the length of the molecule) and can include one or more pendant groups attached to the backbone portion of a monomer unit or to the terminus of the polymer. The pendant group can be functionally and chemically different from the monomer units that form the backbone chain. A polymer can be characterized by its degree of polymerization (DP), where DP is defined as the number of monomeric or repeat units in the polymer which is determined by the molecular weight (number average) of the polymer divided by the molecular weight of the repeat unit. Hydrophobic fluorescent polymers disclosed herein typically have a degree of polymerization that ranges from about 5 to about 250. In certain embodiments, the non-fluorescent polymer has DP of about 5 to about 50; or about 50 to about 100; or about 100 to about 150; or about 150 to about 200; or about 200 to about 250; or an amount between these values. Non-fluorescent polymers can have a degree of polymerization of about 3 to about 150. In certain embodiments, the non-fluorescent polymer has DP of about 5 to about 20; or about 20 to about 50; or about 50 to about 100; or about 100 to about 150; or an amount between these values. Polymers that can be implemented in the formulations described herein include linear polymers and branched polymers. A "linear polymer" includes a linear sequence of monomer units, whereas a "branched polymer" can include additional polymer chains (i.e., branches) that issue from the backbone of the polymer. The polymer can be a homopolymer or a copolymer. A copolymer can include a random or alternating arrangement of monomer units. A linear polymer with a sequence (also referred to as a "segment") of monomer units of a common type that is joined to a sequence of monomer units of a different type is referred to herein as a "block polymer" or "block copolymer". A block copolymer can include two or more blocks (i.e., segments). A branched polymer in which the chemical composition of the monomer units of the branched chains is different than those of the main chain is referred to as a "graft copolymer".

"Fluorescent polymer" is used herein to refer to a polymer that includes one or more groups that can absorb and emit light. Depending on the composition, a fluorescent polymer can absorb and/or emit light in the near ultraviolet (UV) to far infrared (IR) range of the electromagnetic spectrum. A fluorescent polymer can be a conjugated polymer that exhibits semiconductive properties. "Fluorescent polymer," as used herein, also refers to a polymer that is linked to one or more fluorophore, such as a fluorescent, organic dye through a side chain on the backbone of the polymer (e.g., pendant group) or a terminal unit of the polymer (e.g., end group). The polymer that is linked to one or more fluorophores can be a conjugated polymer or can be a polymer that does not contain conjugated segments or exhibit semiconductive properties or exhibit fluorescence properties. A "fluorescent polymer" also refers to an amphiphilic polymer where one or more hydrophilic and/or hydrophobic segments of the polymer is attached to a fluorophore. An amphiphilic polymer attached to a fluorophore also is referred to herein as an "amphiphilic fluorescent polymer."

"Conjugated polymer" is used herein to refer to a polymer that contains an extended series of unsaturated bonds. The conjugated polymer can have semiconductive properties (i.e., exhibit a direct band gap that leads to an efficient absorption or emission at the band edge). The backbone of the conjugated polymer can contain alternating double and single bonds. A conjugated polymer can be conjugated along the full length of its backbone or can contain conjugated segments together with non-conjugated segments.

"Conjugated" is used herein to refer to an unsaturated organic system having adjacent atoms with pi electrons where there is overlap of a p-orbital with another across an intervening sigma bond. In larger atoms, d-orbitals can be involved. The atoms can be $sp^2$ or sp hybridized carbon atoms or other atoms with unshared electron pairs which can be hybridized into p orbitals.

"Water-soluble" and "water-dispersible" are used interchangeably herein to mean a material that can be soluble or suspendable (e.g., dispersible) in an aqueous-based solution, such as in water or water-based solutions or buffer solutions, including those used in biological or molecular detection systems. While water-soluble particles may not be truly "dissolved" in the sense the term is used to describe individually solvated small molecules, they are solvated and suspended in solvents that are compatible with their outer surface layer. Thus, a particle that is readily dispersed in water is considered water-soluble or water-dispersible. A water-soluble particle is also considered hydrophilic, since its surface is compatible with water and with water solubility. The use of one or more amphiphilic molecules in the fluorescent particle can increase the hydrophilicity of the material and can improve the solubility or dispersibility of the material in an aqueous environment.

"Solubility parameter" is used herein to refer to a numerical value that indicates the relative solvency behavior of a specific solvent and/or material (e.g. polymer). For example, the solubility parameter is an indication of solubility for a material in a particular solvent. The solubility parameter also can provide a numerical estimate of the degree of interaction between materials. The solubility of a material can vary as a function of composition, molecular weight, solvent type, temperature, and degrees of freedom upon mixing. Materials with similar solubility parameters can interact with each other and result in solvation, miscibility or swelling. Solubility parameters for many materials are provided in the literature and are typically reported in units of $MPa^{1/2}$ or $cal^{1/2}$ $cm^{-3/2}$. A particularly useful expression for the solvency behavior of a material is the Hildebrand Solubility Parameter, defined as the square route of the cohesive energy density. The units for the Hildebrand solubility parameter ($\delta$) are (calories per $cm^3$)$^{1/2}$, or $cal^{1/2}$ $cm^{-3/2}$ or $J^{1/2}$ $m^{-3/2}$, if reported in SI units. Other solubility scales can be used to assess the miscibility of materials, disclosed herein, including, for example, Hansen solubility parameters, calculating a material's solubility parameter through group contributions or estimating a material's solubility parameter by matching it to solvents that readily dissolve a given material. For materials without reported solubility parameters, solubility parameters can be estimated based on literature values for similar compounds or experimentally determined. A representative method for experimentally measuring the solubility parameter for a material (e.g., a hydrophobic polymer) involves dissolving the material in various solvents spanning a range of solubility parameters. An upper and lower solubility parameter for the material can be established based on the solubility of the material in the selected solvents to establish a solubility parameter range.

"Hydrophobic" is used herein to refer to a surface property of a solid, or a bulk property of a liquid, where the solid or liquid exhibits greater miscibility or solubility in a low-dielectric medium than it does in a higher dielectric medium. By way of example, a material that is more soluble in a hydrocarbon solvent such as decane than in methanol would be considered hydrophobic. Hydrophobic polymers and hydrophobic segments of amphiphilic polymers disclosed herein have a solubility parameter of 10.0 or less (calories per $cm^3$)$^{1/2}$.

"Hydrophilic" is used herein to refer to a surface property of a solid, or a bulk property of a liquid, where the solid or liquid exhibits greater miscibility or solubility in a high-dielectric medium than it does in a lower dielectric medium. By way of example, a material that is more soluble in a polar organic solvent (e.g., methanol) than in a hydrocarbon solvent such as decane would be considered hydrophilic.

"Dye" or "organic dye" or "fluorescent dye," is used herein to refer to an organic compound that exhibits fluorescence when excited at an appropriate wavelength of light and emits light at a higher wavelength than the excitation wavelength. An organic dye can be an energy acceptor or an energy donor in a Förster resonance energy transfer (FRET) process.

"Arene" is used herein to refer to an aromatic hydrocarbon molecule with a conjugated cyclic molecular structure. Arenes can include monocyclic or polycyclic aromatic structures and can be optionally substituted at one or more substitutable positions. Representative examples of arenes include benzene, anthracene, naphthalene, indene and fluorene.

"Aryl" is used herein to refer to any organic radical derived from an arene by loss of one hydrogen atom. An aryl group can be formed from an aromatic ring or a plurality of fused aromatic rings and can be optionally substituted at one or more substitutable positions. Typical aryl groups contain 1 to 5 aromatic rings, which may be fused and/or linked. Representative examples of aryl groups include phenyl, naphthyl, indenyl and fluorenyl.

"Heteroarene" is used herein to refer to an arene in which at least one carbon atom in at least one aromatic ring is replaced by a heteroatom (e.g., nitrogen, oxygen, sulfur, and phosphorus), such that the aromaticity of the compound is retained, and can be optionally substituted at one or more substitutable positions. Examples of heteroarenes include thiophene, carbazole, pyridine, pyrimidine, furan, oxadiazole spirofluorene, indenofluorene, thienopyrazine, dithienosilole, quinoxaline, benzothiadiazole, thienobenzothiophene, thienothiophene and triarylamine.

"Heteroaryl" is used herein to refer to any organic radical derived from a heteroarene by loss of one hydrogen atom and can be optionally substituted at one or more substitutable positions. Exemplary heteroaryl groups include furanyl, thienyl, pyridyl, pyridazinyl, pyrrolyl, N-lower alkyl-pyrrolo, pyrimidyl, pyrazinyl, triazinyl, tetrazinyl, triazolyl, tetrazolyl, imidazolyl, bipyridyl, tripyridyl, tetrapyridyl, phenazinyl, phenanthrolinyl, purinyl, perylene, perylene diimide, kidetopyrrolopyrrole, benzothiodiazol, benzoxadiazol, thienopyrazine and the like. Additional examples of heteroaryl groups include fused ring systems, such as, for example, benzofuryl, benzothienyl, benzopyrrolyl, dibenzofuryl, dibenzothienyl, phenanthrolinyl, carbazolyl and azacarbazolyl groups.

"Dibenzosilole" is used herein to refer to a compound having a fused aromatic ring structure similar to fluorene with the exception that the C9 carbon of fluorene is substituted with a silicon atom. A dibenzosilole optionally can be substituted at one or more substitutable positions as described herein. An organic radical derived from dibenzosilole by loss of one hydrogen atom is referred to herein interchangeably as a "dibenzosilole group" or "dibenzosilyl group." A compound that includes a dibenzosilole group that is substituted with one or more polymerizable groups is referred to herein as a "dibenzosilole monomer". Polymerizable groups can be attached at any position of the dibenzosilole monomer; however, polymerizable groups typically are attached at the 2- and 7-positions of the dibenzosilole monomer. A polymer formed by polymerization of one or more dibenzosilole monomers is referred to herein as a "dibenzosilole polymer" or "poly(dibenzosilole)." A polymer that includes dibenzosilole groups that are linked through the 2 and 7 positions is also referred to as a "poly(2,7-dibenzosilole)." A dibenzosilole polymer can be a homopolymer that includes a plurality of linked dibenzosilole monomer residues. The monomer residues in a dibenzosilole homopolymer can include the same or different pendant groups. Alternatively, a dibenzosilole polymer can be a copolymer that includes one or more dibenzosilole monomer residues having the same or different pendant groups and one or more monomer residues that do not include a dibenzosilole group.

Provided herein are water-dispersible, fluorescent particles that exhibit narrow-band emission and exceptional brightness and include a combination of hydrophobic and amphiphilic polymers. Also provided herein are novel hydrophobic and amphiphilic polymers for use in such fluorescent particles, as well as methods for preparing fluorescent particles. The disclosed fluorescent particles are dispersible in aqueous medium (e.g., water or buffers) and can be used in various applications that require solubility in aqueous environments, such as are frequently encountered in life sciences applications.

Each water-dispersible, fluorescent particle includes a hydrophobic internal region, also referred to herein as the "core" of the particle. The hydrophobic internal region of the particle includes a one or more hydrophobic polymers. The hydrophobic polymers include one or more hydrophobic segments. In certain embodiments, the internal region of the particle includes a mixture of hydrophobic polymers. The mixture can be a homogeneous polymer blend (also referred to herein as a "miscible blend"). A "miscible blend" refers to a homogeneous mixture having a single-phase structure. Homogeneous polymer blends typically exhibit a single glass transition ($T_g$) temperature. In certain embodiments, the hydrophobic internal region of the particle includes a mixture of one or more fluorescent, hydrophobic polymers and one or more non-fluorescent, second hydrophobic polymers. The hydrophobic polymers include one or more hydrophobic segments. Typically, the mixture is a miscible blend of the fluorescent and non-fluorescent, hydrophobic polymers and the one or more non-fluorescent, second hydrophobic polymers.

The fluorescent particle further includes an external region encapsulating the hydrophobic internal region that includes one or more amphiphilic polymers. The external region of the particle is also referred to herein as the "shell" of the particle. The amphiphilic polymer(s) includes at least one hydrophobic segment and at least one hydrophilic segment. At least some of the hydrophilic segments in the amphiphilic polymer are exposed on the surface of the particle to render the particle dispersible in water. In certain embodiments, the hydrophilic segments of the amphiphilic polymer extend outward from the particle to facilitate dispersion of the particle in aqueous media. In certain embodiments, the amphiphilic polymer includes reactive functional groups that can provide sites for covalent attachment of ligands. The hydrophobic segment(s) of the amphiphilic polymer(s) are selected to be miscible with the hydrophobic internal region of the particle, such that the hydrophobic segment is embedded within the hydrophobic internal region of the particle. There is no requirement to form strong chemical bonds (e.g., covalent or ionic) between the hydrophobic polymers within the core of the particle and the amphiphilic polymers. Rather, it is believed that the hydrophobic segments of the amphiphilic polymers and hydrophobic polymers interact via weaker intermolecular hydrophobic interactions to maintain the structure of the particle in aqueous solution. Because hydrophobic segments of the amphiphilic polymer are embedded within the internal, hydrophobic region of the core, the amphiphilic polymer provides a stable, outer shell that retains and protects the mixture of hydrophobic polymers in the internal core region of the particle. As a result, the hydrophobic fluorescent and non-fluorescent polymers, if present, within the core of the particle are not exposed at the exterior surface of the particles. For particles that include FRET-capable fluorophores within the hydrophobic internal region of the particle, the particle's external hydrophilic shell can minimize inter-particle energy transfer between the encapsulated fluorophores, even for sub-micron sized particles that include a high concentration of fluorophores and/or are within the Förster energy transfer range. The amphiphilic shell also protects the encapsulated fluorophores from the external media and restricts leaching or release from the particle even upon prolonged exposure to aqueous environments. This resistance to leaching of the fluorophore from the particle distinguishes the instant particles from those utilized in drug-delivery applications requiring release of a therapeutic agent from the particle.

The hydrophobic polymers and hydrophobic polymer segments of the amphiphilic polymer(s) residing within the internal region of the particles are typically selected to be miscible. Miscible polymers and polymer segments can blend into each other without separating, even after storage of the particles in aqueous environments for extended periods of time. In addition, the use of miscible hydrophobic polymers and segments, as disclosed herein, also has a surprising impact on the ultimate size of the particle when produced using the precipitation methods disclosed herein. It was found that when miscible hydrophobic polymers and segments of the amphiphilic polymer(s) are subjected to the flash nanoprecipitation methods disclosed herein, the resulting particles have diameters that are significantly smaller and have a narrower distribution of sizes than when non-miscible components are used under the same reaction conditions. Without wishing to be bound by theory, the reduction in particle size is thought to occur because the rate of particle core growth matches the rate at which the hydrophobic block deposits on the growing core during precipitation of the particle. Due to their miscibility, the hydrophobic reaction components can better blend together, thus resulting in more compact and smaller particles. For hydrophobic polymers and segments to be miscible, the solubility parameters for the hydrophobic polymers and segments typically differ by less than about 1 $cal^{1/2}$ $cm^{-3/2}$. In certain embodiments, the solubility parameters differ by less than about 0.9 $cal^{1/2}$ $cm^{-3/2}$; or less than $0.8^{-3/2}$ $cal^{1/2}$ $cm^{-3/2}$; or less than $0.7^{-3/2}$ $cal^{1/2}$ $cm^{-3/2}$; or less than $0.6^{-3/2}$ $cal^{1/2}$ $cm^{-3/2}$ or less than $0.5^{-3/2}$ $cal^{1/2}$ $cm.^{-3/2}$ In other embodiments, the solubility parameters differ by less than about 0.1 $cal^{1/2}$ $cm^{-3/2}$; or less than 0.05 $cal^{1/2}$ $cm^{-3/2}$; or less than 0.01 $cal^{1/2}$ $cm^{-3/2}$.

Solubility parameters for the hydrophobic fluorescent and non-fluorescent polymers used within the internal region of the fluorescent particles disclosed herein typically range from about 8.0 $cal^{1/2}$ $cm^{-3/2}$ to about 10.0 $cal^{1/2}$ $cm^{-3/2}$. In certain embodiments, the Hildebrand solubility parameter of the hydrophobic, fluorescent polymers and non-fluorescent polymers can be about 8.0 $cal^{1/2}$ $cm^{-3/2}$ to about 10.0 $cal^{1/2}$ $cm^{-3/2}$. In certain embodiments, a hydrophobic, fluorescent or non-fluorescent polymer can, independently, have a solubility parameter about 8.5 to about 9.5 $cal^{1/2}$ $cm.^{-3/2}$ More specifically, the solubility parameter for a hydrophobic, fluorescent or non-fluorescent polymer can be, independently, about 8.5 cal$^{1/2}$ cm$^{-3/2}$ to 8.7 cal$^{1/2}$ cm$^{-3/2}$; or 8.7 cal$^{1/2}$ cm$^{-3/2}$ to 8.9 cal$^{1/2}$ cm$^{-3/2}$; or 8.9 cal$^{1/2}$ cm$^{-3/2}$ to 9.1 cal$^{1/2}$ cm$^{-3/2}$; or 9.1 cal$^{1/2}$ cm$^{-3/2}$ to 9.3 cal$^{1/2}$ cm$^{-3/2}$; or 9.3 cal$^{1/2}$ cm$^{-3/2}$ to 9.5 cal$^{1/2}$ cm.$^{-3/2}$. In certain embodiments, the internal region of the particle includes a hydrophobic, fluorescent polymer having a the Hildebrand solubility parameter of 9.1 cal$^{1/2}$ cm$^{-3/2}$ to 9.3 cal$^{1/2}$ cm$^{-3/2}$, and a hydrophobic, non-fluorescent polymer having a the Hildebrand solubility parameter of 8.8 cal$^{1/2}$ cm$^{-3/2}$ to 9.3 cal$^{1/2}$ cm$^{-3/2}$.

The amounts of fluorescent and non-fluorescent polymers in the particles disclosed herein can be varied depending on the desired optical and physical properties. The total amount of hydrophobic polymer (i.e., fluorescent and non-fluorescent, hydrophobic polymers) used in the particle can vary but needs to be an amount that induces formation of particles during the precipitation process. If an insufficient quantity of hydrophobic polymer is used in the precipitation process disclosed herein, the resulting product will likely include a substantial quantity of micelles. Micelle formation generally can be avoided when the relative amount of hydrophobic polymers relative to the total weight of the particle is greater than 20%; or about 20% to about 80%; or about 25% to about 50%; or about 30% to about 35%.

The amount of fluorescent hydrophobic polymer(s) relative to the total amount of amphiphilic and non-fluorescent polymers in the particle also can be adjusted to tune the optical properties of the fluorescent particles disclosed herein. Typically, the amount of fluorescent polymer in the particle is 50% or less by weight. For example, the amount of fluorescent polymer can be about 0.5% to 10%; or about 10% to 20%; or about 20% to 30%; or about 30% to about 40%; or about 40% to about 50%. In certain embodiments, the weight percentage of fluorescent polymer in the particle is about 5% to about 40%; or about 10% to about 20%; or about 20% to about 30%; or about 30% to about 40%. In certain embodiments, particle includes about 10% to about 35% by weight fluorescent polymer.

The hydrophobic internal region of the particle can include a mixture of one or more fluorescent, hydrophobic polymers and one or more non-fluorescent, second hydrophobic polymers. In general, the ratio of the fluorescent, hydrophobic polymer to the non-fluorescent hydrophobic polymer in the internal region of the particle is about 1:200 to about 200:1 by weight. For example, fluorescent particles provided herein can have a weight ratio of fluorescent to non-fluorescent hydrophobic polymers of about 1:100 to about 100:1; or about 1:50 to about 50:1 or about 1:20 to about 20:1; or 1:10 to about 10:1. In certain embodiments, the weight ratio of fluorescent to non-fluorescent hydrophobic polymers is about 1:5 to 5:1; or about 2:1 to 4:1; or about 3:1. In certain embodiments (e.g., where the fluorescent polymer includes a conjugated polymer that is optionally linked to one or more small-molecule organic dyes), the weight ratio of fluorescent polymer to non-fluorescent polymer ranges is about 5:1; or about 4:1; or about 3:1; or about 2:1; or about 1:1. In other embodiments (e.g., the fluorescent polymer includes a non-fluorescent, hydrophobic polymer that is linked to one or more small-molecular organic dyes), the weight ratio of fluorescent to non-fluorescent hydrophobic polymers is about 9:1 to about 20:1.

The amount of hydrophobic, fluorescent polymer relative to the total weight of fluorescent and non-fluorescent hydrophobic polymers within the internal region of particle, expressed as a weight percentage, can be about 0.5% to about 95.5%; or about 0.5% to about 10%; or about 10%-25%; or about 25% to about 50%; or about 50% to about 75%; or about 75% to about 95%. In certain embodiments, the amount of hydrophobic, fluorescent polymer relative to the total amount of hydrophobic polymer within the internal region of particle is about 70% to about 95% by weight.

A hydrophobic, non-fluorescent polymer can be included in the internal region of the fluorescent particles disclosed herein. The non-fluorescent, hydrophobic polymer can range in size, but typically has a number average molecular weight ($M_n$) of about 1000 g/mol to about 10,000 g/mol, as measured by GPC. For example, $M_n$ for the non-fluorescent polymer can be about 1200 g/mol to about 3000 g/mol. In certain embodiments, $M_n$ for the non-fluorescent polymer is about 1500 to 2500 g/mol.

When the internal region incorporates more than one type of hydrophobic polymer, it is advantageous that the non-fluorescent polymer be miscible with other hydrophobic polymers residing within the core. Thus, hydrophobic, non-fluorescent polymers suitable for use in the particles provided herein typically have a solubility parameter ranging from 8 to 10 cal$^{1/2}$ cm$^{-3/2}$. Hydrophobic, non-fluorescent polymers having the requisite range of solubility parameters can be chosen from various classes of polymers, including, without limitation, vinyl polymers, acrylic polymers, polyvinyl esters, polyvinyl ketones, and polyesters.

Suitable vinyl polymers include vinyl aromatic compounds, such as styrene polymers (e.g., polymers prepared from styrene or substituted styrene) that can be optionally substituted with alkyl, aryl, halogen, haloalkyl. In certain embodiments, the vinyl aromatic compound is poly(α-methylstyrene) optionally substituted with H, alkyl, aryl, halogen, or haloalkyl.

Suitable acrylic polymers include a group represented as —CR(X)—CH$_2$, where X is H, alkyl (C1 to C4), aryl, heteroaryl, or CN; and R is COOR$^1$ (e.g., acrylates and methacrylates). Acrylic polymers can include a group represented as —CONR$^1$R$^2$ (e.g., acrylamides and methacrylamides), where R$^1$ and R$^2$ are independently selected from H, alkyl (C1 to C10), aryl, alkyl alcohols, alkyl halides, and combinations thereof.

Suitable polyvinyl esters include a group represented as —(COCOR(H)—CH$_2$), where R is alkyl, aryl or substituted alkyl.

Suitable polyvinyl ethers include a group represented as —(COR(H)—CH$_2$), where R is alkyl, aryl or substituted alkyl.

Suitable polyvinyl ketones include a group represented as —(CCOR(H)—CH$_2$), where R is alkyl, aryl or substituted alkyl.

Suitable polyesters include, e.g., polylactic acid, polycaprolactone.

Representative examples of hydrophobic, non-fluorescent polymers include, without limitation, poly(alkyl methacrylates), poly(alkyl acrylates), poly(alkyl methacrylamides), poly(alkyl acrylamides), alkyl substituted polystyrenes, wherein alkyl is selected from C$_{1-10}$ alkyl (e.g., methyl-dodecyl), polylactic acid, polycaprolactone, and poly(vinyl acetate). In certain embodiments, the non-fluorescent polymer can be a copolymer of two or more acrylic or vinyl polymers, such as, e.g., acrylamide-co-acrylates, acrylate-co-styrene, and the like.

Fluorescent particles provided herein can include one or more fluorescent polymers and/or organic dyes. A fluorescent polymer can include a group that can absorb and/or emit light having a wavelength from the UV to near-IR region of the electromagnetic spectrum. The fluorescent polymer can be hydrophilic or hydrophobic. In certain embodiments, the fluorescent polymer absorbs light but then transfers energy to an acceptor dye (e.g., a polymeric or small molecule organic dye) without itself emitting light, in which case the fluorescent polymer behaves as a donor dye in a fluorescence resonance energy transfer (e.g., FRET) process. Fluorescent polymers that are capable of undergoing a FRET process are particularly useful to produce a particle that emits brightly in the far-red or near-IR region of the spectrum.

Fluorescent polymers can include a conjugated segment. Extended conjugation within the polymer backbone allows the polymer to exhibit fluorescence emission upon excitation at an appropriate wavelength of light. In certain embodiments, the fluorescent polymer is a semiconducting polymer that is capable of absorbing and/or emitting light and/or transferring energy to an acceptor dye. Because the disclosed fluorescent polymers exhibit a host of favorable optical properties, this class of polymers is ideal for use in biological assays requiring a high level of sensitivity. In certain embodiments, fluorescent polymers are provided that emit bright, visible light upon UV excitation. For example, certain fluorescent polymers provided herein can absorb light having a wavelength below about 500 nm; or about 300 nm to about 500 nm. In certain embodiments, the fluorescent particle includes a polymer that absorbs light having a wavelength of about 300 nm to about 420 nm. In some embodiments, the polymer absorbs at about 350 nm to about 410 nm. For example, fluorescent polymers including a conjugated segment can be effectively irradiated using lasers emitting in the violet spectral (e.g., 405 nm). Upon irradiation at an appropriate wavelength, fluorescent polymers can emit light having a wavelength of greater than about 400 nm; or about 400 to about 800 nm.

The fluorescent polymer can range in size, but typically has a number average molecular weight ($M_n$) of about 10,000 g/mol to about 90,000 g/mol, as measured by GPC using a polystyrene size standard. In certain embodiments, $M_n$ for the fluorescent polymer is about 20,000 g/mol to about 40,000 g/mol. In certain embodiments, $M_n$ for the fluorescent polymer is about 25,000 g/mol to about 35,000 g/mol (e.g., about 30,000 g/mol).

The fluorescent polymer can be a homopolymer or a copolymer or oligomer and can be a linear or a branched polymer. Copolymers can be alternating, random and block polymers where the percentage of each monomer used to prepare the polymer can vary. The polymer can include monomer residues that provide additional conjugation such that their presence does not disrupt the conduction of electrons through the polymer or significantly degrade the optical properties of the polymer. Incorporation of additional aromatic monomer repeat units into conjugated polymers can be used to tailor both the energy levels of the polymer and the stability of the resulting compositions. In addition, incorporation of such groups into the polymer can be used to optimize light absorption, ionization potential, and/or electronic properties of the polymer for particular applications. For example, copolymerization of acetylene, phenylenes, p-phenylenevinylene, pyrene, naphthalene, fluorene, pyrrole, carbazole, aniline, thiophene, 3,4-ethylenedioxythiophene, p-phenylene sulfide, benzothiadiazole and dibenzosilole monomers with other types of conjugated monomers (e.g., arenes or heteroarenes) can provide conjugated polymers with altered fluorescence excitation and emission profiles. For example, incorporation of additional aromatic monomer residues (e.g., benzodithiazole, phenyl or thiophenyl) in the polymer backbone can alter the electronic properties of the polymer and shift the excitation and emission wavelength of the copolymer.

Also provided herein are conjugated polymers having a backbone formed from one or more monomer residues that include different types of aromatic groups. The aromatic group, which can be substituted or unsubstituted, can be an arene or heteroarene. Representative examples of aromatic groups for copolymerization in polymers described herein include, without limitation, benzene, naphthalene, fluorene, thiophene, carbazole, pyridine, pyrimidine, spirofluorene, indenofluorene, thienopyrazine, dithienosilole, quinoxaline, benzothiadiazole, thienobenzothiophene, thienothiophene and triarylamine groups.

The fluorescent polymer can include a monomer residue having a structure of the formula, —[Ar]n-, wherein Ar is an aryl or heteroaryl group that can be optionally substituted with one or more substituents, such as halogen, hydroxyl, C1-C12 alkyl, C2-C12 alkene, C2-C12 alkyne, C3-C12 cycloalkyl, C1-C12 haloalkyl, C1-C12 alkoxy, C2-C18(hetero)aryloxy, and C2-C18(hetero)arylamino. For example, the fluorescent polymer can include an optionally substituted arylene, heteroarylene, arylene vinylene, heteroarylene vinylene, arylene ethylene, heteroarylene, ethylene, phenylene, thienylene, fluorenylene, spirobifluorenylene, indenofluorenylene, pyridylene, bipyridylene, carbazoylene, indenocarbazolylene, benzothiazolylene, and oxadiazolylene.

Representative classes of fluorescent polymers include polyphenylene-ether, polyarylenevinylenes, polyaryleneethynylene, dibenzosilole polymers, fluorene polymers, phenylene vinylene polymers, phenylene polymers, benzothiazole polymers, thiophene polymers, carbazole fluorene polymers, boron-dipyrromethene polymer, and derivatives and copolymers thereof.

Specific, non-limiting, examples of fluorescent polymers include poly(9,9-dihexylfluorenyl-2,7-diyl) (PDHF), poly(9,9-dioctylfluorenyl-2,7-diyl) (PFO)), (poly[{9,9-dioctyl-2,7-divinylene-fluorenylene}-alt-co-{2-methoxy-5-(2-ethylhexyloxy)-1,4-phenylene}](PFPV), poly[(9,9-dioctylfluorenyl-2,7-diyl)-co-(4,7-di-2-thienyl-2,1,3-benzothiadiazole)] (PFTBT), poly[(9,9-dioctylfluorenyl-2,7-diyl)-9-co-(4,7-di-2-thienyl-2,1,3-benzothiadiazole)] (PF-0.1TBT)), poly[(9,9-dioctylfluorenyl-2,7-diyl)-alt-co-(1,4-benzo-(2,1',3)-thiadiazole)] (PFBT, also referred to as PBT herein), poly[(9,9-di(2-ethylhexyl)fluorenyl-2,7-diyl)-alt-2,5-difluoro-1,4-benzene] (PFDFB), poly[(9,9-di(2-ethylhexyl)fluorenyl-2,7-diyl)-alt-1,4-benzene] (PFB), poly[(9,9-di(2-ethylhexyl)fluorenyl-2,7-diyl)-alt-4,4'-diphenyl-5,6-difluoro-1,4-benzo-(2,1,3)-thiadiazole] (PFDPDFBT), poly[(9,9-di(2-ethylhexyl)fluorenyl-2,7-diyl)-alt-4,4'-diphenyl-1,4-benzo-(2,1,3)-thiadiazole] (PFDPBT), (poly[(9,9-di(2-ethylhexyl)fluorenyl-2,7-diyl)-alt-4,4'-diphenyl-5-fluoro-1,4-benzo-(2,1,3)-thiadiazole] (PFDPFBT), poly[2-methoxy-5-(2-ethylhexyloxy)-1,4-phenylenevinylene] (MEH-PPV)), poly[2-methoxy-5-(2-ethylhexyloxy)-1,4-(1-cyanovinylene-1,4-phenylene)] (CN-PPV), poly(BODIPY) and derivatives and combinations thereof.

In certain embodiments, the fluorescent polymer is poly(9,9-dihexylfluorenyl-2,7-diyl) (PDHF), poly(9,9-dioctylfluorenyl-2,7-diyl) (PFO), (poly[{9,9-dioctyl-2,7-divinylene-fluorenylene}-alt-co-{2-methoxy-5-(2-ethylhexyloxy)-1,4-phenylene}] (PFPV), poly[(9,9-dioctylfluorenyl-2,7-diyl)-co-(4,7-Di-2-thienyl-2,1,3-benzothiadiazole)] (PFTBT), poly[(9,9-dioctylfluorenyl-2,7-diyl)-alt-co-(1,4-benzo-(2,1',3)-thiadiazole)] (PFBT), poly[2-methoxy-5-(2-ethylhexyloxy)-1,4-phenylenevinylene] (MEH-PPV)), poly(BODIPY) or a derivative or combination thereof. In certain embodiments, the fluorescent polymer is poly(9,9-dioctylfluorenyl-2,7-diyl) (PFO), poly[(9,9-dioctylfluorenyl-2,7-diyl)-alt-co-(1,4-benzo-(2,1', 3)-thiadiazole)] (PFBT), poly(BODIPY) or a derivative or combination thereof. For example, the fluorescent polymer can be an optionally substituted polyfluorene or polyfluorene-co-benzothiazole.

Fluorescent polymers for use in the particles provided herein also can include an energy donor-acceptor structure. This class of polymers is ideal for preparing fluorescent particles for use in biological assays requiring a high level of sensitivity and emission in the far-red or near-IR regions of the spectrum. For example, fluorescent polymers utilizing a FRET system can emit bright visible or near-IR light upon UV excitation. The particles can include different combinations of energy acceptor and energy donor fluorophores to tune the excitation and emission properties of the particles. Representative examples of such combinations include, without limitation: 1) a mixture of two or more types of FRET-capable, fluorescent polymers, 2) a mixture of a FRET-capable polymer and an energy acceptor fluorophore (e.g., a small molecule, organic dye or fluorescent polymer), 3) a copolymer that includes at least one polymeric segment that functions as an energy donor and at least one polymeric segment that functions as an energy acceptor fluorophore, or 4) a copolymer that includes at least one polymeric segment that functions as an energy donor, at least one polymeric segment that functions as an energy acceptor, and at least one energy acceptor fluorophore (e.g., a small molecule, organic dye).

In certain embodiments, the fluorescent polymer includes monomer residues that facilitate energy transfer within the polymer chain (i.e., intrachain energy transfer) and/or between polymer chains (i.e., interchain energy transfer). For example, a fluorescent polymer can include a first type of monomer that is capable of functioning as an energy donor upon irradiation at light of an appropriate wavelength. The first type of monomer that can act as an energy donor to a second type of monomer, contained within the same polymer or within a different fluorescent polymer, is capable of functioning as an energy acceptor.

Thus, provided herein are fluorescent polymers that are capable of an intramolecular FRET process. In certain embodiments, the fluorescent polymer is a semiconducting polymer including a conjugated segment that is capable of absorbing light at a first wavelength and then transferring the absorbed energy to a different conjugated segment of the polymer that then can emit light at a different, second wavelength. In some embodiments, energy is transferred intramolecularly to another segment within the polymer, and the transferred energy is then relayed to an energy acceptor unit. For example, a narrow-band energy acceptor unit can be introduced into the backbone of the semiconducting polymer to facilitate intramolecular energy transfer. Intramolecular FRET also can be achieved using a fluorescent polymer that includes a conjugated segment that is capable of absorbing light at a first wavelength and includes pendant groups that include a fluorescent dye. In such a system, light absorbed by the conjugated segment of the polymer is transferred to the energy acceptor dye that then emits light at a different, second wavelength.

In some embodiments, the fluorescent and/or non-fluorescent, hydrophobic polymer within the particle core can be linked to a small molecule, organic dye. Fluorescent polymers that are linked to one or more organic dyes have applicability as donor-acceptor FRET systems. For example, a polymer can include a conjugated segment that can absorb light at a first wavelength (i.e., energy donor). The polymer can be attached to one or more organic dye units, where the dye serves as an energy acceptor and can emit light of a different wavelength. Alternatively, or in addition, one or more organic dyes can be linked to a non-fluorescent, hydrophobic polymer. In some embodiments, the particle core includes more than one type of hydrophobic polymer, each linked to a different organic dye. Systems including two different organic dyes that can function as donor-acceptor FRET systems (i.e., tandem FRET systems) are particularly well-suited for multi-color assays such as flow cytometry. For example, highly efficient energy transfer between two different organic dyes (e.g., BODIPY dyes) contained within individual particles can be achieved using excitation wavelengths exceeding 405 nm. Such systems are particularly useful in assays using lasers tuned beyond the violet spectral region. For example, and depending on the organic dyes utilized in the particular system, a blue (488 nm), green (532 nm), yellow (561 nm) or red (633 nm to 638 nm) laser can be used for irradiation of the fluorescent particle.

Also provided herein are fluorescent particles including one or more amphiphilic fluorescent polymers. Here, one or more organic dyes linked to the hydrophobic and/or hydrophilic segments of an amphiphilic polymer to provide a fluorescent, amphiphilic polymer. The location of attachment depends on the type of dye and whether fluorescence emission is benefitted by a hydrophobic or hydrophilic environment. For example, a hydrophobic segment of an amphiphilic polymer can be linked to a hydrophobic dye configured to reside within the hydrophobic internal region of the particle. Alternatively, a hydrophilic segment of an amphiphilic polymer can be linked to a hydrophilic dye configured to reside on or protrude from the surface of the particle. In other embodiments, a hydrophobic segment of the amphiphilic polymer can be linked to a hydrophilic dye, such that the hydrophilic dye resides within the hydrophilic shell of the particle. In yet other embodiments, a hydrophilic segment of the amphiphilic polymer can be linked to a hydrophobic dye, such that the hydrophobic dye resides within the hydrophobic core region of the particle.

Representative examples of organic dyes that can be linked to the amphiphilic and hydrophobic polymers disclosed herein include boron dipyrromethenes (4,4-difluoro-4-bora-3a,4a-diaza-s-indacenes), cyanines, xanthenes, sulfonated pyrenes, rhodamines, coumarins, and derivatives thereof. Exemplary organic dyes include BODIPY dyes, coumarins (e.g., PACIFIC BLUE, PACIFIC GREEN and PACIFIC ORANGE (available from Thermo Fisher Scientific; Waltham, Mass.)), rhodamines, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol; aminorhodamine, carboxyrhodamine, chlororhodamine, methylrhodamine, sulforhodamine, silicon rhodamine, and thiorhodamine, cyanine, indocarbocyanine, oxacarbocyanine, thiacarbocyanine, merocyanine, cyanines (e.g., cyanine 2, cyanine 3, cyanine 3.5, cyanine 5, cyanine 5.5, cyanine 7), oxadiazole derivatives, pyridyloxazole, nitrobenzoxadiazole, benzoxadiazole, pyrene derivatives, cascade blue, oxazine derivatives, Nile red, Nile blue, cresyl violet, oxazine 170, acridine derivatives, proflavin, acridine orange, acridine yellow, arylmethine derivatives, xanthene dyes, sulfonated xanthenes dyes, sulfonated pyrenes, auramine, crystal violet, malachite green, tetrapyrrole derivatives, porphyrin, phtalocyanine, and bilirubin. In certain embodiments, the organic dye is a near-infrared dye, such as, e.g., CY5.5 (GE Healthcare Life Sciences; Pittsburgh, Pa.), IRDYE 800 (Li-Cor; Lincoln, Nebr.), DYLIGHT 750 (Thermo Fisher Scientific) or indocyanine green (ICG), or a cyanine dye, such as, e.g., cyanine 2, cyanine 3, cyanine 3.5, cyanine 5, cyanine 5.5, cyanine 7. In certain embodiments, the organic dye is a xanthene or sulfonated xanthenes dyes, such as those commercially available under the tradenames ALEXA FLUOR 594, ALEXA FLUOR 633, ALEXA FLUOR 647 and ALEXA FLUOR 700 (Thermo Fisher Scientific). An additional example of a commercially available dye is ALEXA FLUOR 405 (Thermo Fisher Scientific).

As discussed above, the water-dispersible, fluorescent particles disclosed herein include an amphiphilic polymer. The amphiphilic polymer(s) includes at least one hydrophobic segment and at least one hydrophilic segment. At least some of the hydrophilic segments in the amphiphilic polymer are exposed on the surface of the particle to render the particle dispersible in water. Generally, the amphiphilic copolymer exhibits a surface tension when dissolved in water at 0.1 wt % of at least 50 dynes/cm. The amphiphilic polymer can range in size, but typically has a number average molecular weight ($M_n$) of about 2000 g/mol to about 25,000 g/mol, as measured by GPC. For example, the amphiphilic polymer can have $M_n$ of about 3500 g/mol to about 10,000 g/mol. In certain embodiments, $M_n$ of the amphiphilic polymer is about 3900 g/mol to about 9200 g/mol. The molecular weight of the hydrophilic and hydrophobic segments of the amphiphilic polymer can be independently varied. Typically, the hydrophilic block is at least 1000 g/mol to facilitate colloidal stability after particle formation; and the hydrophobic block is at least 1000 g/mol to enhance insolubility of the block in the chosen solvent and promote precipitation. Typically, the hydrophobic segment of the amphiphilic polymers has a $M_n$ of greater than about 1000 g/mol. For example, the $M_n$ of the hydrophobic segment can be about 1000 g/mol to about 5000 g/mol; and $M_n$ of the hydrophilic segment can be about 2000 g/mol to about 10,000 g/mol. In one embodiment, the amphiphilic polymer is a polystyrene-block-PEG copolymer, wherein the $M_n$ of the polystyrene is about 1700 g/mol and $M_n$ of the PEG block is about 7500 g/mol PEG.

The hydrophilic segment can include water-solubilizing groups to increase the hydrophilicity of the polymer. Water-solubilizing substituents described herein are sufficiently hydrophilic, such that they can be dispersed or dissolved in aqueous medium. The water-solubilizing group can carry a positive or negative charge. In some embodiments, the water-solubilizing group does not carry a positive or negative charge. Incorporation of uncharged water-solubilizing groups can provide an amphiphilic polymer having no net charge. Uncharged polymers may provide lower levels of non-specific binding to certain hydrophobic or cellular surfaces. Representative examples of water-solubilizing groups include carboxylic acids, amines, sulfonic acids, sulfonates, thiosulfate, phosphonate, boronate, ammonium, alkylammonium, alcohols, ethers, polyethers, amides, sulphonamides and derivatives and salts thereof and the like. Additional examples of water-solubilizing groups include non-charged, hydrophilic groups such as saccharides and polysaccharides (e.g., dextrans) and zwitterionic polymers. Water-solubilizing groups also include those having one or more alkylene oxide repeat units. For example, the water-solubilizing group can contain one or more ethylene glycol units, —($OCH_2CH_2$)—. Ethylene glycol oligomers or polymers are referred to herein as a "polyethylene glycol" (PEG) or "polyethylene oxide" (PEO) group. In certain embodiments, the hydrophilic segment includes a block of ethylene glycol units. The PEG block can be any length, however, typically includes between 45 to 230 ethylene glycol repeat units. In certain embodiments, the PEG group includes 50 to 175 ethylene glycol repeat units.

The hydrophobic segment(s) of the amphiphilic polymer(s) typically is selected to be miscible with the hydrophobic internal region of the particle, such that the hydrophobic segment is embedded within the hydrophobic internal region of the particle when the particle is in an aqueous environment. For the hydrophobic segment of the amphiphilic polymer to be miscible with the hydrophobic polymers in the core of the particle, the hydrophobic segment typically includes a monomer unit of the same composition as a monomer unit in one or more of the hydrophobic polymers.

The hydrophobic segment of the amphiphilic polymer can include any type of hydrophobic polymer that is miscible with the hydrophobic polymer(s) used in the preparation of the particle. For example, the hydrophobic segment can include a hydrophobic polymer selected from polystyrenes, alkyl methacrylates, alkyl acrylates, alkyl methacrylamides, alkyl acrylamides, alkyl substituted styrenes, wherein alkyl is selected from $C_{1-10}$ alkyl (e.g., methyl-dodecyl), lactic acid, caprolactone, and vinyl acetate. Exemplary hydrophobic segments can include, e.g., polystyrene, poly(α-methylstyrene), polymethyl methacrylate, poly(ethyl methacrylate), poly(butyl methacrylate), poly(butyl acrylate), poly(lactic acid), polycaprolactone, poly(vinyl acetate), poly(vinyl propionate), or poly(vinyl butyrate). In certain embodiments, the hydrophobic segment includes polystyrene, poly(α-methylstyrene), polymethyl methacrylate, poly(lactic acid), and polycaprolactone.

Graft, block or random amphiphilic copolymers can be used to prepare the fluorescent particles described herein. In certain embodiments, the external region of the fluorescent particle includes an amphiphilic block copolymer. It is believed that the hydrophobic block of the amphiphile associates with the growing particle core during synthesis, while the hydrophilic block sterically stabilizes the particle in solution. Once enough amphiphile deposits on the growing particle core, the hydrophilic block then arrests particle growth. As a result, amphiphilic block copolymers can facilitate formation of particularly stable particle dispersions in aqueous solution.

Representative examples of amphiphilic polymers include copolymers having a first block formed from acrylamide, methacrylamide, acrylate, methacrylate, oxazoline monomers and a second block formed from acrylamide, methacrylamide, acrylate, methacrylate, or styrene monomers. Illustrative, non-limiting examples of amphiphilic block copolymers include poly(acrylamide)-block-polystyrene, poly(N,N-dimethyl acrylamide)-block-polystyrene, poly(N-methyl methacrylamide)-block-polystyrene, poly(N-2-hydroxypropyl methacrylamide)-block-polystyrene, poly(acrylamide)-block-poly(methyl methacrylate), poly(N,N-dimethyl acrylamide)-block-poly(methyl methacrylate), poly(N-methyl methacrylamide)-block-poly(methyl methacrylate); poly(N-2-hydroxypropyl methacrylamide)-block-poly(methyl methacrylate), and poly(acrylamide)-block-poly(methyl methacrylate). Additional examples of amphiphilic block copolymers include a polystyrene derivative such as, e.g., poly(alpha-methyl styrene and poly(4-methyl styrene), polylactic-acid-PEO (PLA-PEO) and polystyrene-PEO (PS-PEO).

The amphiphilic polymer can further include a reactive functional group that can be used to couple the fluorescent particle to another substance (e.g., a protein, hapten, nucleic acid, or a solid support) to form a conjugate. In certain embodiments, the reactive group is linked to the amphiphilic polymer surrounding the hydrophobic core of the particle. The fluorescent particles disclosed herein can be linked to a substance covalently or non-covalently to form a conjugate. Substances can be conjugated to a reactive functional group on the particle, optionally through a linker. For example, a fluorescent particle bearing a reactive functional group can be conjugated to a substance (e.g., an antibody or fragment thereof) bearing a group capable of reacting with the reactive functional group. For example, a reactive group can reside on the hydrophilic portion of the amphiphilic polymer that extends outward from the particle surface, such that it is available for conjugation with a material bearing a functional group capable of reacting with the reactive group on the particle surface. Representative examples of reactive groups include a carboxylic acid, an activated ester (e.g., succinimidyl ester) of a carboxylic acid, a carboxylic ester, an acrylamide, an acyl an azide, an alkynyl, an acyl nitrile, an aldehyde, an alkyl halide, an allyl, an anhydride, an aniline, an amine, an aryl halide, an aziridine, a boronate, a diazoalkane, a haloacetamide, a halotriazine, a hydrazide, a hydrazine, an imido ester, an isocyanate, an isothiocyanate, a maleimide, a phosphoramidite, a reactive platinum complex, a silyl halide, a sulfonyl halide, a thiol, and a photoactivatable group such as, for example, an aryl azide, a benzophenone or a diazirine. Alternatively, the fluorescent particle can be bound non-covalently to a substance, as disclosed herein. For example, a conjugate can be prepared using a biotin-streptavidin affinity binding system, where one member of the conjugate is linked to streptavidin or a derivative thereof and the other member is linked to biotin or a derivative thereof.

The external shell can include one or more types and/or molecular weights of amphiphilic polymer. The composition and amount of amphiphilic polymer in the particle can be adjusted to control the number of the hydrophobic and hydrophilic segments in the shell region of the particle and to provide varying types and/or levels of functional groups on the particle surface. In certain embodiments, the amphiphilic polymer is a polystyrene-PEG copolymer. In certain embodiments, a mixture of two different polystyrene-PEG copolymers is used in the shell of the particle. Optionally, the amphiphilic polymer can include one or more reactive functional groups (e.g., an amine, NHS-ester, carboxylate, maleimide, alkyne, azide and the like) for attachment to ligands. In certain embodiments, a mixture of two different block copolymers of polystyrene and PEG (e.g., polystyrene-b-PEG) is used in the shell of the particle, where a portion of the PS-b-PEG copolymers (e.g., about 1 mol % to about 75 mol %) can include reactive functional groups (e.g., a carboxylic acid, amine, azide or alkyne). In certain embodiments, about 5 mol % to about 50 mol % of the PS-b-PEG copolymers can include reactive functional groups.

Substances that can be attached either covalently or non-covalently to the fluorescent particle include, without limitation, amino acids, peptides and proteins (e.g., antibodies or fragments thereof, fluorescent protein, and metal binding protein), nucleosides, nucleotides, nucleic acid bases, oligonucleotides, and nucleic acid polymers (e.g., DNA or RNA), and microorganisms, such as a biological cell (e.g., animal or plant cell, bacterium, yeast) or virus. Further examples of conjugated substances include avidin or a derivative thereof (e.g., streptavidin, neutravidin) and haptens (e.g., fluorescein, biotin, digoxigenin or DNP (2,4-dinitrophenyl)). In certain embodiments, the conjugate includes a fluorescent particle linked to an antibody, an antigen, streptavidin or biotin. Other conjugated substances include enzymes, polysaccharides (e.g., dextrans), dyes, semiconductor nanocrystals, and synthetic polymers. Alternatively, or in addition, the fluorescent particles can be attached to a solid support, e.g., particles, magnetic or non-magnetic beads, films, wells, plates, containers, and the like.

The water-dispersible, fluorescent particles provided herein can include a surface, reactive group suitable for coupling to a substance using a bioorthogonal conjugation reaction. Bioorthogonal conjugation chemistries are well-known to those skilled in the art and include, without limitation, cycloaddition reactions (e.g., click chemistry), reactions between amine and activated carboxylic acid ester groups, reactions between maleimide and thiol groups, and between hydrazine and aldehyde groups. In certain embodiments, the particle can be substituted either directly or through a linker to a terminal or cyclic alkyne or an azide group, such that the particle is capable of reacting with a compound bearing a functional group (e.g., an alkyne or azide) that is capable of reacting with the reactive functional group on the particle using a cycloaddition reaction (e.g., click chemistry). In certain embodiments, the fluorescent particle bears the alkyne functional group, whereas the reactive substance (e.g., antibody) bears an azido functional group, although the reverse is also possible. It often can be beneficial to eliminate the use of metal ion catalysts, such as copper, when performing cycloaddition or other types of conjugations due to the potential for metal ion-mediated fluorescence quenching and/or the harmful effect of metal or metal ions on live cells. For example, in systems including live cells, a strained, cyclic alkyne (e.g., DIBO) can be implemented in a cycloaddition reaction with a compound bearing an azido functional group to obviate the need for copper catalyst. In certain embodiments, for example, the fluorescent particle bears a strained, cyclic alkyne and the reactive substance (e.g., antibody) bears an azido group. In other embodiments, for example, the fluorescent particle bears an azido group and the reactive substance (e.g., antibody) bears a strained, cyclic alkyne. In either case, a copperless click cycloaddition reaction can be used to couple the azido and alkyne functional groups to form the conjugate.

Also provided herein are methods for preparing fluorescent particle conjugates. In general, a fluorescent particle including a surface reactive functional group, as disclosed herein, can be coupled to a substance, such as a ligand, biomolecule, support, or the like, optionally through a linker using methods that are well known in the art. The particles can be used directly after conjugation, or optionally, the conjugate can be purified prior to use in order to remove unwanted components in the sample, e.g., using size exclusion chromatography.

The physical properties, size and optical characteristics of the water-dispersible, fluorescent particles and conjugates provided herein can be tailored by altering the chemical composition and/or varying the relative amounts of fluorescent and non-fluorescent, hydrophobic and/or amphiphilic polymers used in the preparation of the particles. As discussed above, the hydrophobic internal region of the water-dispersible, fluorescent particles can include a mixture of one or more fluorescent, hydrophobic polymers and one or more non-fluorescent, hydrophobic polymers. Altering the types and relative amounts of fluorescent and non-fluorescent polymers contained within the internal region of the particle can affect the optical and physical properties of the particles. For example, optical properties, such as excitation and emission profiles and/or quantum yield, can be tuned by adjusting the type and ratio of fluorescent to non-fluorescent polymer. Thus, manipulation of the types and amounts of fluorescent material provides particles that can be excited by light in the UV, visible or near-IR portions of the electromagnetic spectrum using, for example, a laser tuned to 355 nm, 405 nm, 488 nm, 532 nm, 561 nm or 633 nm.

The type and amount of hydrophobic polymers contained within the internal region of the particle also can affect the size and surface characteristics, of the particle. For example, the relative amounts of fluorescent and non-fluorescent polymers contained within the internal region of the particle can dramatically impact the affinity of molecules such as proteins to the surface of the fluorescent particles. Surprisingly, incorporating hydrophobic, non-fluorescent polymer within the internal core region of the particle has been found to reduce the level of non-specific binding to the surface of the particle.

Several exemplary, non-limiting embodiments are provided herein to illustrate different compositions that can be used in the hydrophobic, internal region of a water-dispersible, fluorescent particle, as disclosed herein.

In certain embodiments, the internal region of the fluorescent particle includes a fluorescent polymer (e.g., polyfluorene or a copolymer or derivative thereof) having a solubility parameter of 9.1 cal$^{1/2}$ cm$^{-3/2}$ to 9.3 cal$^{1/2}$ cm$^{-3/2}$. The molecular weight ($M_n$) of the fluorescent polymer can range from about 15,000 to about 100,000; or about 25,000 g/mol to about 80,000 g/mol; or about 30,000 g/mol to about 70,000 g/mol. The internal region of the particle further includes a hydrophobic, non-fluorescent polymer (e.g., polystyrene). The molecular weight ($M_n$) of the hydrophobic, non-fluorescent polymer can range from about 1000 g/mol to about 10,000 g/mol, e.g., about 1200 g/mol to about 3000 g/mol. The ratio of the fluorescent polymer (e.g., PFO) to non-fluorescent polymer (e.g., PS) can vary from about 1:1 to about 4:1 by weight. In certain embodiments, the ratio is about 3:1 by weight. The molecular weight of non-fluorescent polymer can range from about 1000 to about 10,000. In some embodiments, the non-fluorescent polymer is polystyrene having a $M_n$ of about 1200 g/mol to about 3000 g/mol. The mixture of hydrophobic polymers are encapsulated by an amphiphilic polymer, as described herein, yielding sub-micron sized, water-dispersible, fluorescent nanoparticles that emit indigo light (about 415 to 465 nm) upon excitation at about 345 nm to 415 nm.

In other embodiments, the internal region of the particle can include a conjugated, fluorescent polymer that includes one or more pendant groups, at least one of which can be linked to a fluorescent organic dye. The fluorescent polymer can harvest light, and the absorbed energy can be transferred (e.g., via a FRET mechanism) to the organic dye that is linked to the polymer. In such a construction, the fluorescent polymer functions as an energy donor, while the organic dye functions as an energy acceptor. In one embodiment, the internal region of the fluorescent particle includes a fluorescent polymer, such as a polyfluorene, that is linked to a hydrophobic, organic dye, such as a boron-dipyrromethene or a derivative thereof. A representative example of such a copolymer is PFO-co-(Fluorene-BODIPY 493/503). In other embodiments, the fluorescent copolymer can include a first, light-harvesting segment. The energy absorbed by the first segment is then transferred to a second segment within the polymer that then transfers the energy to an organic dye that is linked to the polymer. In this type of two-step FRET construction, the first segment of the fluorescent polymer functions as an energy donor that relays energy to the second segment, and the second segment then transfers energy to the light-emitting organic dye. Exemplary BODIPY dyes that can be used in FRET relay polymers emit at about 500 nm to 800 nm and include, without limitation, BODIPY 493/503, BODIPY FL, BODIPY 530/550, BODIPY R6G, BODIPY 576/589, BODIPY 581/591, BODIPY-TMR, BODIPY 630/650, BODIPY 650/665 (all available from Thermo Fisher Scientific). One representative example of such a relay polymer is a copolymer of a polyfluorene and PBT that is linked to a BODIPY dye, represented as (PFO)$_{xn}$-co-(PBT)$_{yn}$co-(Fluorene-BODIPY), where n refers to the degree of polymerization, or number of repeat units. One- and two-step FRET polymers typically have a $M_n$ that ranges from about 10,000 to about 60,000 g/mol. In some embodiments, $M_n$ is about 15,000 g/mol to about 45,000 g/mol.

In other embodiments, the internal region of the particle includes a mixture of a one-step or two-step FRET polymer and a hydrophobic, non-fluorescent polymer (e.g., polystyrene). In certain embodiments, the hydrophobic polymer has a molecular weight of about 1200 to about 3000 g/mol. The ratio of the 1-step or 2-step FRET polymer relative to non-fluorescent hydrophobic polymer can vary from about 1:1 to about 4:1 by weight. In certain embodiments, the ratio is about 3:1 by weight. The mixture of hydrophobic polymers is encapsulated by an amphiphilic polymer, as described herein, yielding sub-micron sized, water-dispersible, fluorescent particles that emit over a range of wavelengths. Representative particles incorporating such mixtures can emit green to red light from about 500 nm to about 680 nm upon excitation at about 345 nm to about 415 nm.

Also provided herein are water-dispersible fluorescent particles that include a fluorophore within the particle's internal region. The fluorophore can be a copolymer of a first fluorescent polymer unit and a second fluorescent polymer unit linked to an organic dye (e.g., a BODIPY dye). The dye can be linked either directly or indirectly via a linker to a reactive functional group (e.g., pendant group) on the second fluorescent polymer unit. Upon excitation at an appropriate wavelength of light, the fluorescent polymer can transfer energy (e.g., via an intramolecular FRET mechanism) to the organic dye, such that the organic dye emits light at a second wavelength. Suitable polymers for use as first and/or second fluorescent polymer units in such a system can include a semiconducting polymer, as disclosed herein, such as, e.g., polyfluorene or a derivative thereof. By way of illustration, the fluorescent polymer can be a copolymer including a first block of PFO (i.e., 9,9-dioctylfluorenyl-2,7-diyl) and a second block of a polyfluorene derivative (e.g., 9-(3-aminopropyl)-9-methyl-9H-fluorenyl-2,7-diyl)) carrying a reactive pendant group (e.g., NH$_2$) for conjugation to an organic dye, represented as (PFO)$_{xn}$-co-(NH$_2$—PF)$_{yn}$, where x and y refer to mol % monomer used in the polymerization reaction and n refers to the degree of polymerization, or number of repeat units. Optionally, the fluorophore can further include a third fluorescent polymer unit that is different from the first and second polymer units. The third unit can linked to the first and/or second fluorescent unit to form a fluorescent copolymer. Upon excitation at an appropriate wavelength of light, the third polymer unit can transfer ("relay") energy from the first to the second polymer unit linked to the organic dye, such that the organic dye emits light at a second wavelength. The third fluorescent unit also can be a semiconducting polymer. Examples of semiconducting polymers for use in the third unit include, e.g., poly[(9,9-dioctylfluorenyl-2,7-diyl)-alt-co-(1,4-benzo-(2,1',3)-thiadiazole)] (PFBT), poly[(9,9-dioctylfluorenyl-2,7-diyl)-alt-co-(4,7-di(thiophen-2-yl)benzo[c][1,2,5]thiadiazole)] (PBT2T), poly[(9,9-dioctylfluorenyl-2,7-diyl)-alt-co-(bithiophene)] (PF2T), poly[3-hexylthiophene-2,5-diyl] (PHT), poly[(9,9-dioctyl-2,7-divinylenefluorenylene)-alt-co-(9,10-anthracene)] (PVFA), poly[2,6-(4,4-bis-(2-ethyl-hexyl)-4H-cyclopenta[2,1-B; 3,4-B'] dithiophene)-alt-4,7(2, 1,3-benzothiadiazole)] (PCPTBT), poly[2-methoxy-5-(2-ethylhexyloxy)-1,4-phenylenevinylene] (MEH-PPV)), poly [2-methoxy-5-(2-ethylhexyloxy)-1,4-(1-cyanovinylene-1,4-phenylene)] (CN-PPV), poly(BODIPY), or a derivative or copolymer thereof. In particular embodiments, the third unit of the fluorescent polymer includes PFBT (i.e., PBT) or a derivative or copolymer thereof. An exemplary copolymer that includes three fluorescent units and bearing a pendant group for attachment to an organic dye is poly[(9,9-dioc-tylfluorenyl-2,7-diyl)$_{xn}$-co-(4,7-dibromobenzo[c][1,2,5] thiadiazole)$_{yn}$-co-(tert-butyl-4-(2,7-dibromo-9-methyl-9H-fluoren-9-yl)propylcarbamate)$_{zn}$], represented as (PFO)$_{xn}$-co-(PBT)$_{yn}$-co-(NH$_2$—PF)$_{zn}$, where x, y, z and n are as described above.

It was surprisingly found that when fluorophores including particular ratios of first, second and optionally third polymer units, as disclosed herein, are condensed into water-dispersible fluorescent particles, the FRET energy transfer efficiency (i.e., the efficiency of energy transfer from the first and second donor polymer units (and third polymer unit, if present) to the acceptor dye) is markedly improved relative to the FRET efficiency exhibited for the identical fluorophore in solution. For example, the fluorophore can exhibit a solution-state FRET efficiency of 25% or less and a FRET efficiency of 80% or greater (i.e., at least a 2-fold enhancement) when packaged into particulate form. In certain embodiments, the efficiency of energy transfer for the fluorophore can be greater than about 80% (e.g., 85% or greater; or about 90% or greater; or about 95% or greater; or about 96% to about 99%). Energy transfer efficiency can be significantly improved (e.g., at least a 2-fold increase) for particles including a fluorophore having at least 90% of the first fluorescent unit and 10 mol % or less of the second fluorescent unit. In certain embodiments, a significant FRET enhancement can be achieved for a fluorophore including 93 mol % or more of the first fluorescent polymer unit and about 5 mol % or less (e.g., about 1 mol %, 2 mol %, 3 mol %, 4 mol % or 5 mol %) of the second fluorescent polymer unit. In other embodiments, a significant (i.e., 2-fold or greater) FRET enhancement can be achieved for a fluorophore including a third fluorescent unit, as disclosed herein. A fluorophore including three fluorescent units and exhibiting significant FRET enhancement when packaged into particulate form can include, for example, at least 90% of the first fluorescent unit and 10 mol % or less of combined second and third fluorescent units. In certain embodiments, e.g., the fluorophore can include about 93 mol % or more of the first fluorescent polymer unit; about 5 mol % or less (e.g., about 1 mol %, 2 mol %, 3 mol %, 4 mol % or 5 mol %) of the second fluorescent polymer unit; and 5 mol % or less (e.g., about 1 mol % to about 3 mol %) of a third fluorescent polymer unit.

In yet other embodiments, water-dispersible, fluorescent particles are provided that include a hydrophobic internal region, including a mixture of one or more fluorescent, first hydrophobic polymers and one or more non-fluorescent, second hydrophobic polymers, wherein the amount of the one or more fluorescent, first hydrophobic polymer relative to the sum total weight of first and second hydrophobic polymers in the internal region is about 25% to 90%. In some embodiments, the relative amount of fluorescent, hydrophobic polymer is about 60% to about 80%. The one or more first hydrophobic polymer is optionally linked to one or more fluorescent organic dyes and has a number average molecular weight ($M_n$) of about 20,000 g/mol to about 40,000 g/mol, and a solubility parameter of 9.1 cal$^{1/2}$ cm$^{-3/2}$ to 9.3 cal$^{1/2}$ cm$^{-3/2}$. The second hydrophobic polymer can include residues of vinyl aromatic monomers, has a number average molecular weight ($M_n$) of about 1200 g/mol to about 3000 g/mol, and a solubility parameter of 8.8 cal$^{1/2}$ cm$^{-3/2}$ to 9.3 cal$^{1/2}$ cm$^{-3/2}$, and the solubility parameters of the first and second hydrophobic polymers differ by less than 1 cal$^{1/2}$ cm$^{-3/2}$. The fluorescent particle further includes an external region encapsulating the hydrophobic internal region that includes one or more amphiphilic polymers, each including at least one hydrophobic segment embedded in the hydrophobic internal region of the particle and at least one hydrophilic segment that renders the particle dispersible in water. The solubility parameter of the at least one hydrophobic segment of the one or more amphiphilic polymers differs from the solubility parameter of the one or more non-fluorescent, hydrophobic polymers by less than 1 cal$^{1/2}$ cm$^{-3/2}$.

In yet other embodiments, the internal region of the particle can include one or more hydrophobic, fluorescent polymers. In one exemplary system, the internal region includes a mixture of two or more hydrophobic, fluorescent polymers. For example, the internal region can include two different, miscible fluorescent polymers. In one type of construction, each fluorescent polymer has distinct excitation and emission properties. For example, one polymer can be excited at a first wavelength and can emit at a second wavelength. The second polymer within the hydrophobic core can be excited at a third wavelength, which can be the same or different than the first wavelength, and can emit at a fourth wavelength. Alternatively, the first polymer harvests light at a first wavelength and then transfers the absorbed energy to the second polymer within the hydrophobic core, which then can emit light at a second wavelength (e.g., via an intermolecular FRET mechanism). In certain embodiments, each hydrophobic, fluorescent polymer is a semiconducting polymer.

In yet another embodiment, the internal region of the particle includes a hydrophobic, non-fluorescent polymer that is linked to a fluorescent organic dye. In other systems, the internal region of the particle includes a two or more types of miscible, hydrophobic, non-fluorescent polymers, each linked to a different fluorescent organic dye. The dyes can be excited and/or emit at different wavelengths of light. In certain embodiments, the organic dyes within the internal region of the particle are capable of intermolecular energy transfer. Upon excitation at an appropriate wavelength of light, the dye linked to the first polymer and the dye linked to the second polymer are capable of transferring energy, e.g., via an intermolecular FRET mechanism. The excitation and emission wavelengths can differ slightly from the solution-state values upon packaging of the dyes into particles. In a representative system, the donor fluorophore is polystyrene-BODIPY 493/503 (excitation 505 nm, emission 518 nm) and the acceptor is polystyrene-BODIPY-TMR (excitation 551 nm, emission 578 nm). The ratio of donor to acceptor dye contained within the internal region of the particle can vary but generally ranges from about 2:1 to about 20:1 by weight, depending on the desired excitation/ emission profile and/or brightness of the particle. In certain embodiments, the ratio of donor dye to acceptor dye is about 10:1 to about 15:1 by weight. The first and second hydrophobic, non-fluorescent polymers contained within the internal region of the particle are selected such that they are miscible and can be formed of the same type and number of monomer units or can be formed from different types and/or numbers of monomers units. For example, the hydrophobic, non-fluorescent polymer can include a polystyrene derivative (e.g., amino polystyrene) that is linked to a fluorescent, organic dye. In certain embodiments, the molecular weight ($M_n$) of the hydrophobic polymer (e.g., polystyrene) ranges from about 1500 g/mol to about 5000 g/mol. In certain embodiments, $M_n$ for each polymer is about 2000 g/mol to about 3000 g/mol (e.g., about 2500 g/mol).

The internal region of the particle can further include an additional hydrophobic, non-fluorescent polymer, as disclosed herein. In certain embodiments, the additional hydrophobic polymer is polystyrene. In such systems, the amount of unmodified, hydrophobic polymer relative to the total amount of unmodified and dye-modified hydrophobic materials residing in the core of the particle is typically less than about 25% and typically ranges from about 5% to about 15% (e.g., about 10%). The mixture of hydrophobic polymers is encapsulated by an amphiphilic polymer, as described herein, yielding sub-micron sized, water-dispersible, fluorescent nanoparticles that emit at about 560 nm to about 605 nm (e.g., yellow to orange) light upon excitation at about 480 nm to 520 nm.

In certain embodiments, a water-dispersible, fluorescent particle is provided that includes a hydrophobic internal region, including a mixture of one or more fluorescent, first hydrophobic polymers and one or more non-fluorescent, second hydrophobic polymers, wherein the amount of the one or more first hydrophobic polymer relative to the sum total weight of first and second hydrophobic polymers in the internal region is about 80% to about 95%. The one or more first hydrophobic polymer comprises residues of vinyl aromatic monomers and is linked to one or more fluorescent organic dyes, and has a number average molecular weight ($M_n$) of about 1200 g/mol to about 3000 g/mol, and a solubility parameter of 8.8 $cal^{1/2}$ $cm^{-3/2}$ to 9.3 $cal^{1/2}$ $cm^{-3/2}$. The second hydrophobic polymer includes residues of vinyl aromatic monomers and is optionally linked to one or more fluorescent organic dyes, has a number average molecular weight ($M_n$) of about 1200 g/mol to about 3000 g/mol, and a solubility parameter of 8.8 $cal^{1/2}$ $cm^{-3/2}$ to 9.3 $cal^{1/2}$ $cm^{-3/2}$, wherein the first organic dye and the second organic dye, if present, undergo FRET upon excitation at an appropriate wavelength of light, wherein the solubility parameters of the first and second hydrophobic polymers differ by less than 1 $cal^{1/2}$ $cm^{-3/2}$. The fluorescent particle further includes an external region encapsulating the hydrophobic internal region that comprises one or more amphiphilic polymers, each comprising at least one hydrophobic segment embedded in the hydrophobic internal region of the particle and at least one hydrophilic segment that renders the particle dispersible in water, wherein the solubility parameter of the at least one hydrophobic segment of the one or more amphiphilic polymers differs from the solubility parameter of the one or more non-fluorescent, hydrophobic polymers by less than 1 $cal^{1/2}$ $cm^{-3/2}$.

In yet other embodiments, the fluorescent polymer is included in the external region of the particle. For example, the external region of the particle can include an amphiphilic fluorescent polymer. In certain embodiments, the amphiphilic polymer that forms the external region of the particle can include a hydrophilic or hydrophobic segment that is attached to one or more fluorophores. In certain embodiments, the fluorescent polymer includes an amphiphilic polymer that includes a hydrophilic segment attached to one or more fluorophores. In other embodiments, the fluorescent polymer includes an amphiphilic polymer that includes a hydrophobic segment attached to one or more fluorophores. The core of the particle can include only non-fluorescent, hydrophobic polymers (e.g., polystyrene). However, in certain constructions, the internal region of the particle further includes a fluorescent polymer, as disclosed herein, and/or fluorophore that is the same or different than the fluorophore that is attached to the amphiphilic polymer.

The fluorophore attached to the hydrophilic or hydrophobic segment of the amphiphilic polymer can be hydrophilic or hydrophobic, depending on whether it is desired to retain the fluorophore within the internal or external region of the particle. Representative dyes that can be linked to the amphiphilic polymer include, without limitation, fluorescent dyes that can be excited by light having a wavelength of 400 nm to 800 nm and emit in the visible to far-red region of the spectrum. For example, certain particles including an amphiphilic, fluorescent polymer provided herein can emit from about 500 nm to about 700 nm light upon excitation at about 465 nm to 670 nm. The dyes that can be linked to the amphiphile are typically water-soluble, however, less hydrophilic dyes can be used, as well. Representative dyes include rhodamine and cyanine-based fluorescent dyes, such as, those available from Thermo Fisher Scientific (e.g., ALEXA FLUOR 405, ALEXA FLUOR 488, ALEXA FLUOR 546, ALEXA FLUOR 555, ALEXA FLUOR 568, ALEXA FLUOR 594, ALEXA FLUOR 647, ALEXA FLUOR 680, ALEXA FLUOR 700, DYLIGHT 405, DYLIGHT 488, DYLIGHT 550, DYLIGHT 650) and ATTO-TEC GmbH, Germany (e.g., ATTO 488 and ATT0594).

In yet another embodiment, an organic dye is conjugated to the terminus of the hydrophilic segment of the amphiphilic polymer. An exemplary amphiphilic polymer for use in such a construction is an aminoPEG-polystyrene block copolymer, where the organic dye is conjugated to the terminal amino group of the polymer. The molecular weight of the amphiphilic polymer used in an amphiphilic, fluorescent polymer can vary but typically ranges from about 2500 g/mol to about 7000 g/mol. In certain embodiments, that amphiphilic polymer in such a construction has a $M_n$ of about 3500 g/mol to about 5500 g/mol. The amount of fluorophore in the fluorophore-amphiphilic polymer conjugate can be controlled and typically ranges from about 1:50 by weight or less (e.g., 1:40 or 1:30 by weight). In certain embodiments, the total weight of hydrophobic polymers and polymer segments of the amphiphilic polymers relative to the weight of the fluorophore(s) in the particle is typically less than about 25% by weight and is typically 10% by weight or less.

Particles including an amphiphilic, fluorescent polymer also include a non-fluorescent, hydrophobic polymer within the hydrophobic, internal region of the particle. For example, the internal region of such a particle can include a hydrophobic polymer, such as polystyrene, having a $M_n$ of about 1500 g/mol to about 5000 g/mol; or about 2000 g/mol to about 3000 g/mol (e.g., about 2500 g/mol). In certain embodiments, the hydrophobic polymer (e.g., polystyrene) has a $M_n$ of about 1500 g/mol to about 2000 g/mol. The mixture of hydrophobic polymers is encapsulated by an amphiphilic polymer, as described herein, yielding submicron sized, water-dispersible, fluorescent particles.

In certain embodiments, a water-dispersible, fluorescent particle is provided that includes a hydrophobic internal region, including a one or more non-fluorescent, hydrophobic polymers, each including residues of vinyl aromatic monomers and has a number average molecular weight ($M_n$) of about 1200 g/mol to about 3000 g/mol, and a solubility parameter of 8.8 $cal^{1/2}$ $cm^{-3/2}$ to 9.3 $cal^{1/2}$ $cm^{-3/2}$. The fluorescent particle further includes an external region encapsulating the hydrophobic internal region that comprises one or more amphiphilic polymers, each comprising at least one hydrophobic segment embedded in the hydrophobic internal region of the particle and at least one hydrophilic segment that renders the particle dispersible in water, wherein the at least one hydrophobic segment and/or hydrophilic segment is linked to a fluorescent organic dye, wherein the solubility parameter of the at least one hydrophobic segment of the one or more amphiphilic polymers differs from the solubility parameter of the one or more non-fluorescent, hydrophobic polymers by less than 1 $cal^{1/2}$ $cm^{-3/2}$.

The water-dispersible, fluorescent particles described herein are typically spherical in shape and have at least one major dimension from about 1 to about 1000 nm. Particles having a mean hydrodynamic diameter of less than 1 micron and referred to herein as "sub-micron sized particles" or "nanoparticles." As used herein, "mean hydrodynamic diameter" refers to the mean diameter of the particle, as measured by intensity distribution using dynamic light scattering (DLS). Nanoparticles provided herein can have a mean hydrodynamic diameter of about 10 nm to 1000 nm. In certain embodiments, nanoparticles are provided having a mean hydrodynamic diameter of about 20 nm to about 100 nm. In other embodiments, nanoparticles are provided having a mean hydrodynamic diameter of the particle is about 35 nm to about 60 nm.

The particle size depends on various factors, including, e.g., 1) the amount of non-fluorescent, hydrophobic polymer relative to amount of fluorescent polymer in the particle, and 2) the miscibility of the hydrophobic polymers and hydrophobic segments of the amphiphilic polymer residing within the hydrophobic core of the particle. When the hydrophobic segments of the amphiphile and the non-fluorescent polymer have similar solubility parameters, smaller particle sizes with low polydispersity can be achieved than if the solubility parameters of the core hydrophobic polymers and segments differ. The solubility parameters can be matched if the hydrophobic block of the amphiphilic polymer and the hydrophobic, non-fluorescent polymer include the same type of monomer repeat unit. For example, in a particle made using PEG-b-PS as the amphiphilic polymer and polystyrene as the non-fluorescent, hydrophobic polymer, both hydrophobic components in the particle include styrene repeat units, so the solubility parameters for these materials are substantially the same. As a result, the hydrophobic segment of the amphiphile and the non-fluorescent polymer are miscible, such that the hydrophobic segment of the amphiphile can be efficiently incorporated into the hydrophobic core containing the non-fluorescent polymer during particle formation to yield a sub-micron sized population of fluorescent particles, as disclosed herein.

The size of the particle also can be affected by the amount of hydrophobic, non-fluorescent polymer in the particle. In particular, it was found that there is an inverse relationship between particle size and the amount of non-fluorescent, hydrophobic polymer that is contained within the particle. Without wishing to be bound by theory, it is believed that increasing the amount of the non-fluorescent, hydrophobic polymer in the fluorescent particle improves incorporation efficiency of the hydrophobic segment of the amphiphile into the hydrophobic core during particle formulation. This effect is particularly evident when the particle includes miscible hydrophobic polymers. Improved incorporation efficiency can shorten the timescale for arresting particle growth, thereby reducing the hydrodynamic diameter of the particle. As demonstrated in Example 3, increasing the ratio of a non-fluorescent, hydrophobic polymer (i.e., polystyrene) relative to the amphiphilic polymer (PEG-b-PS) resulted in a reduction in the hydrodynamic diameter of the fluorescent particle. Further, the distribution of particle sizes was not negatively impacted with increased PS content. Thus, the reduction in particle size as a function of increasing PS content may be attributed to improved incorporation of the hydrophobic block (i.e., polystyrene) of the amphiphilic polymer into the hydrophobic composite PFO/PS core of the particle.

The fluorescent particles disclosed herein are dispersible and stable in aqueous media, such as, for example, water, saline, buffered aqueous solutions (e.g., borate, carbonate, or phosphate buffer and the like). Aqueous compositions can include a fluorescent particle or conjugate thereof, as described herein, that is dissolved or dispersed in an aqueous medium. Typically, fluorescent particles provided herein are colloidally stable and remain dispersed in aqueous environment and do not aggregate, precipitate or sediment over extended periods of time (e.g., 18 months storage at 4° C.).

The fluorescent particles described herein exhibit minimal non-specific binding to other components (e.g., proteins). High background signal in fluorescence-based assay has been attributed to non-specific binding of molecules (e.g., proteins) to fluorophores. This problem can interfere with accurate signal detection in and is particularly pronounced in complicated multi-component systems, such as encountered in cell-based assays (e.g., flow cytometry). Because the disclosed particles exhibit minimal non-specific binding to other assay components (e.g., proteins), these materials also produce negligible background fluorescence in cell-based assays.

Often, additional components (e.g., blocking agents) are utilized in an assay sample to combat non-specific binding, thereby minimizing undesired background signal. Surprisingly, the water-dispersible, fluorescent particles described herein are exceptionally bright, yet produce remarkably low background signal without the addition of additional components to combat non-specific binding to the particles, even in demanding cell-based assays, such as flow cytometry. For example, it was found that incorporation into the core of at least 10% by weight of non-fluorescent, hydrophobic polymer relative to fluorescent, hydrophobic polymer (e.g., 1:1 ratio or greater) reduced the occurrence of background signal in flow cytometric data significantly (see, Example 35). The reduction was improved further with increasing amounts of non-fluorescent, hydrophobic polymer (i.e., greater than 30%), and the lowest levels of background signal could be achieved when the hydrophobic core contained at least 90% non-fluorescent, hydrophobic polymer. The ability to control the amount of background signal by packaging precise ratios of miscible, fluorescent and non-fluorescent, hydrophobic polymers within the particle core provides a significant advancement over other fluorescent nanoparticle technologies that rely on the use of hydrophilic groups in the shell of the particle to prevent non-specific binding of molecules to the particle surface.

In addition to minimizing background fluorescence, the ability to tailor the amount of miscible fluorescent and non-fluorescent polymers within the particle permits precise control of the amount of fluorophore contained in the particle. The ability to manipulate fluorophore loading in the hydrophobic core of a fluorescent particle has not been possible with previously-described water-soluble, fluorescent particles having a core formed solely from hydrophobic, fluorescent polymers. As a result, water-soluble, fluorescent particles of similar size but different optical properties (e.g., fluorescence intensity and quantum yield) can be prepared by simply adjusting the ratio of fluorescent to non-fluorescent, hydrophobic polymers.

Multiplexed (i.e. multi-color) assays often utilize pairs of fluorescent labels that can interact through a Förster resonance energy transfer process (FRET). Effective FRET systems typically use an amount of acceptor fluorophore that is sufficiently high to minimize interference resulting from emitted light of the donating fluorophore. Although using large amounts of the second, acceptor fluorophore can help minimize the effect of the donor's emission, too much acceptor dye can cause further artifacts. For example, in assays using multiple lasers, if a large quantity of acceptor fluorophore is present, it can be possible to excite the acceptor fluorophore by a laser wavelength that is different from that used to excite the donor fluorophore. Excitation of the acceptor dye can produce interference in this other laser channel. Therefore, in assays using multiple excitation lasers, it is desirable to minimize the amount of acceptor dye in the FRET system. To date, however, reduction in the concentration of acceptor dye has the undesirable consequence of reduced FRET efficiency. A significant advancement provided by the disclosed fluorescent FRET-capable particles is that extremely low amounts of acceptor fluorophore (e.g., 5 mol % or less) are needed to produce highly efficient energy transfer between donor and acceptor fluorophores. As a result, the described particles produce intense Stokes-shifted fluorescence in the desired laser channel, while minimizing spillover of signal into undesired laser channels. This unique combination of properties makes FRET-capable particles, as disclosed herein, particularly suitable for complicated assays utilizing multiple excitation lasers (e.g., flow cytometry).

Thus, in another aspect, a fluorophore is provided that includes a hydrophobic, semiconducting, fluorescent polymer, as disclosed herein (e.g., polyfluorene), that includes a pendant group, and an organic dye, as disclosed herein (e.g., BODIPY) is attached to the pendant group of the fluorescent polymer. The ratio of the organic dye to polymer can be 5 mol % or less. In some embodiments, the ratio of dye to polymer is 3 mol % or less. In certain embodiments, the fluorescent polymer includes at least 93 mol % of a polyfluorene. Upon excitation at an appropriate wavelength of light, the fluorescent polymer can transfer energy to the organic dye, such that the organic dye emits light at a second wavelength. Fluorophores are provided in which the efficiency of energy transfer from polymer to dye is greater than about 80%. In some embodiments, the energy transfer efficiency is 85% or greater. In some embodiments, the energy transfer efficiency is 90% or greater.

The fluorescent particles described herein are photostable and do not dim significantly or exhibit large shifts in emission peak that can result from high intensity and/or prolonged irradiation, making them particularly useful in applications that utilize high intensity lasers (e.g., cell imaging and flow cytometry). The disclosed fluorescent particles also resist self-quenching, which is a phenomenon frequently encountered when fluorescent polymers are condensed into particulate form.

Surprisingly, certain fluorescent polymers described herein exhibit a pronounced increase in fluorescence intensity when in particulate form. In certain embodiments, e.g., fluorescent polymers that exhibit FRET in solution show an increase in FRET efficiency when in particulate form. For example, a significant improvement in FRET efficiency (e.g., about 2-fold) was observed for certain fluorescent polymers when packaged into particles as described herein, and in some cases the improvement was even greater (e.g., about 4-fold).

The sub-micron sized particles provided herein typically include a large number of fluorescent polymer molecules. Due to the high fluorophore to volume ratio, the disclosed particles are exceptionally bright and exhibit intense fluorescence over a wide range of emission wavelengths when irradiated at an appropriate wavelength of light; and routinely exhibit quantum yields of greater than 30% (e.g., greater than 40%; or greater than 50%) in aqueous solution. Interestingly, fluorescent signal and quantum yield was found to improve for certain types of particles when the hydrophobic core contained a significant amount (e.g., greater than about 25%) of non-fluorescent polymer. Without wishing to be bound by theory, the close packing of fluorophores confined within a particle is thought to give rise to fluorescence quenching due at least in part to collisional quenching between adjacent fluorophores. By adding non-fluorescent, hydrophobic polymer that is miscible with the hydrophobic fluorescent polymer into the particle formulations, as disclosed herein, the relative amount of fluorescent polymer contained in the hydrophobic core of the particle decreases. Dilution in the concentration of fluorescent polymer is thought to increase the distance between adjacent fluorophores. As a result, the level of fluorescence quenching is reduced relative to the level experienced by particles in the absence of added hydrophobic, non-fluorescent polymer.

Various strategies can be employed to prepare the fluorescent particles described herein, including precipitation, aggregation and emulsion methods. However, to produce particles with diameters of ≤50 nm, it is desirable to employ nanoprecipitation techniques. These techniques generally involve slowly mixing an organic water miscible solvent, containing dissolved hydrophobic polymeric materials, with an aqueous solvent under sonication. Generally, very low concentrations of hydrophobic, fluorescent polymers (µg/mL) are utilized to prevent large scale (>100 nm) aggregation during particle formation.

Methods of precipitating particles disclosed herein demonstrate good control of particle size and produce nanoparticles in high yield. Small (e.g., ≤50 nm) particles with high quantum yield can be generated using precipitation methods described herein. Surprisingly, the disclosed precipitation methods do not broaden the emission band of the fluorescent materials, as would have been expected due to complex polymer backbone folding behaviors, disordered morphologies and chain aggregation. Rather, the precipitated, fluorescent particles disclosed herein exhibited narrow-band emission in water (e.g., Full Width at Half Maximum, FWHM, of less than 50 nm). In certain embodiments, the emission FWHM is about 10 nm to about 50 nm. For example, the emission FWHM can be about 10 nm to about 20 nm; or about 20 nm to about 30 nm; or about 30 nm to about 40 nm; or about 40 nm to about 50 nm.

A representative method for preparing the particles involves precipitation of particles from solution (e.g., flash nanoprecipitation). Flash nanoprecipitation methods can utilize a mixture of an aqueous and hydrophobic solvent (e.g., an organic solvent that is miscible with water such as THF) to form sub-micron-sized particles (i.e., nanoparticles). In a representative method, a solution of hydrophobic and amphiphilic polymers is rapidly added to an excess of water with rapid agitation (e.g., ultrasonication or high-speed mixing). Upon mixing, the hydrophobic polymers and the hydrophobic segments of the amphiphilic polymers aggregate to form the particles. The hydrophilic segments of the amphiphilic polymers orient towards the exterior portion of the particle into the aqueous phase, such that the hydrophilic segments are concentrated in the shell region of the particle, while the hydrophobic polymer is encapsulated by the amphiphilic polymers. The organic solvent then can be removed from the mixture. Nanoprecipitation methods disclosed herein provide nanoparticles that include a hydrophobic core and a hydrophilic shell that renders the particles dispersible in aqueous media.

Flash nanoprecipitation methods provided herein differ from emulsion and other types of aggregation methods known to those skilled in the art. As an initial matter, the disclosed methods can provide a homogenous distribution of fluorescent particles. In some embodiments the particles can be prepared to display multiple surface reactive groups in a single step. The conditions implemented in nanoprecipitation methods also do not favor the formation of polymeric micelles, because the use of suitable polymers and solvents and rapid mixing conditions can limit self-assembly of amphiphilic polymers prior to encapsulation of hydrophobic polymers. Nanoprecipitation methods disclosed herein also differ processes that rely on self-aggregation, because the polymer components are subjected to rapid mixing (e.g., 1-2 m/s or greater). Rapid mixing favors production of a homogeneous population of similarly sized nanoparticles, without undesired formation of particles or aggregates of particles and/or particles that exceed 100 nm in diameter. The instant methods also differ from methods relying on sonication, requiring very low concentrations of hydrophobic materials (μg/mL) and very slow removal of the chosen solvent to prevent aggregation of the formed nanoparticles. As a result, flash nanoprecipitation can employ much higher polymer concentrations (mg/mL), making scale up more robust.

Flash precipitation can be achieved using various devices known to those skilled in the art. Such devices can introduce components under a controlled mixing velocity in either a batch or continuous manner to produce a high yield of nanoparticles of very small size and narrow particle size distribution. In an exemplary flash precipitation process, separate solvent streams are combined with polymeric components using high mixing speeds (e.g., about 0.02 m/s to about 15 m/s). The mixing velocity, mixing time, solvent type, and ratio of reaction components and temperature can influence the speed of precipitation, as well as particle size and size distribution. Typically, higher mixing speeds yield smaller particle sizes. Once a critical mixing velocity is reached, the particle size no longer decreases.

In one representative method, water-dispersible, fluorescent particles are prepared by dissolving one or more amphiphilic polymers and one or more fluorescent, first hydrophobic polymers (FP) and one or more non-fluorescent, second hydrophobic polymers in an organic solvent to provide a solution. The weight of fluorescent polymer relative to the total weight of the hydrophobic polymers (HP) in the polymer solution is about 99% or less (e.g., less than 95%; or less than 90%; or less than 85%; or less than 80%). This solution then is introduced into water or an aqueous solution that includes a buffering agent or salt. Generally, the solution is introduced into aqueous media at a flow rate of about 10 m/sec to about 15 m/s or greater to flash precipitate fluorescent particles.

By way of illustration, one or more hydrophobic polymers and an amphiphilic polymer in an appropriate solvent (e.g., THF) are flash precipitated to provide sub-micron sized fluorescent particles in water. In certain embodiments, one or more fluorescent, hydrophobic polymers and one or more non-fluorescent polymers and an amphiphilic polymer are precipitated in water to provide fluorescent nanoparticles. In other embodiments, one or more non-fluorescent, hydrophobic polymers and a fluorescent, amphiphilic polymer(s) are precipitated in water to provide fluorescent nanoparticles.

The mean diameter and size distribution of the fluorescent particles produced by flash precipitation can be controlled by, for example, adjusting the type and/or concentration of the components and/or solvent, temperature, and mixing velocity. For example, the fluorescence properties of the particles can be altered by varying the amount of fluorescent polymer relative to the non-fluorescent hydrophobic polymer and/or amphiphilic polymer used in the reaction mixture. The size of the particles can be adjusted by varying the flow rate. Typically, higher flow rates produce smaller particles. Mixing speeds of about 10 m/s or greater can be used to flash precipitate particles having a mean hydrodynamic diameter about 20 nm to about 100 nm, as measured by dynamic light scattering, although larger particles also can be made using the disclosed flash precipitation process.

Water-dispersible particles provided herein can be used in applications that are conducted in aqueous systems. The particles described herein can be used in a biological assay, for example, as fluorescent probes in cell imaging and cell sorting, flow cytometry, as biological and chemical sensors, in hybridization assays (e.g., FISH), PCR assays, Western blotting, and immunoassays, including fluorescent immunosorbent assays such as ELISA and lateral flow assays.

Thus, also provided are methods to determine the presence of target molecule in a sample. Generally, the method involves providing a solution of water-dispersible fluorescent particles and then treating a sample (e.g., a biological material or cells) that contains or is thought to contain target molecules within the solution. The sample can be any material that contains a target molecule or is suspected of containing a target molecule and can contain materials of biological or synthetic origin. The target molecule can be free in solution or contained with a biological material, such as a cell. Exemplary target molecules include, without limitation, proteins (e.g., antibodies or antigens), polysaccharides, lipids, nucleic acids, biotin, streptavidin, and the like. Representative examples of samples include blood, urine, semen, milk, sputum, mucus, a buccal swab, a vaginal swab, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, tumors, organs, in vitro cell culture constituents, and recombinant libraries of polynucleotide sequences.

For biological assays, the particles are typically provided in a biologically compatible solution, such as water or a buffer. In addition, changes in the concentration of particles in the aqueous medium and/or shell thickness can be used to control aggregation of the particles and/or transfer of fluorescence between particles. Thus, particles provided herein typically are utilized at concentrations of less than about 50 mg/mL (e.g., about 1 mg/mL to about 30 mg/mL).

The methods described herein can utilize live cells, dead or fixed cells or a combination of live and dead cells. For labeling of living cells, the fluorescent particles are added to a sample that contains living cells. The sample can include cells suspended in a buffer or media, or cells adherent to a glass or plastic surface, bathed in a buffer or media. Alternatively, or in addition, the sample can include cells that have been lysed or permeabilized to release the cellular components (e.g., proteins, nucleic acid polymers, nucleotides or nucleosides) from within the cells. Cells can be treated with a cell fixative reagent, or a cell fixative reagent combined with a cell permeabilizing reagent, or a cell permeabilizing reagent. The sample can include eukaryotic cells, prokaryotic cells, biological fluids, isolated cell nuclei, or tissue. The cells can be suspended in a fluid (e.g., a biological fluid or an aqueous fluid, such as buffer or water) or may be in a solid form, such as cells adherent to plates, coverslips, dishes, flasks, or solid tissue samples that have been disaggregated.

The fluorescent particle can be used in an unbound form or can be linked to an affinity molecule to provide a composition that can associate with the target molecule under appropriate conditions. The association can be achieved by covalent or non-covalent bonding of the composition to the target molecule. The affinity molecule can recognize and bind to the target molecule through non-covalent interactions (e.g., hydrogen bonding, van der Waals force, and the like), or the particle can include a reactive group that is capable of binding covalently to the target molecule. Representative examples of affinity molecules include biomolecules, such as proteins (e.g., antibody or antigen), nucleic acids, biotin, and avidin and derivatives thereof (e.g., streptavidin), and the like.

In certain embodiments, the particle can bear a reactive group that can react with a complementary reactive group on an affinity or target molecule to provide a covalent linkage between the particle and the target molecule. Various types of reactions can be utilized to couple a reactive fluorescent particle to an affinity molecule or target molecule, including, for example, various types of click reactions (e.g., [3+2] cycloadditions, such as the Huisgen 1,3-dipolar cycloaddition) and Diels-Alder reactions. For example, the particle can bear a reactive pendant group (e.g., an azide or alkyne) that can react via a click reaction with a complementary reactive group (e.g., an alkyne or azide) on the target molecule to bind the particle to the target molecule. The alkyne can be a branched or unbranched hydrocarbon group containing at least one —C≡C— triple bond and can be optionally substituted at one or more positions. Substituents on substituted alkynyl groups include, for example, hydroxyl, cyano, alkoxy, =O, =S, —NO$_2$, halogen, haloalkyl, heteroalkyl, amine, thioether and —SH. In certain embodiments, the alkyne group is a terminal alkyne. Examples of terminal alkynyl groups include ethynyl, n-propynyl, isopropynyl, propargyl, octynyl, decynyl and the like. In other embodiments, the alkyne is a cyclic alkyne. In certain embodiments, the cyclic alkyne is a cyclooctyne. Representative cyclooctynes include monocyclic or bicyclic or tricyclic, unsubstituted or substituted cyclooctynes including, for example, monofluorinated cyclooctynes and difluorinated cyclooctynes. In certain embodiments, the cyclic alkyne is a cyclooctyne, monoarylcyclooctyne, or diarylcyclooctyne, such as a dibenzocyclooctyne (DIBO). Use of a strained cyclooctyne as the reactive group can facilitate a click cycloaddition reaction in the absence of a metal catalyst (e.g., copper), such as when using living cells or delicate fluorescent proteins and antigens.

Thus, in yet another embodiment, fluorescent particles provided herein can include a cyclic alkyne group, such as DIBO or a DIBO derivative. DIBO containing polymers can be conjugated to a complementary azide-containing molecule such as streptavidin-azide or azide-derivatized primary antibodies. For example, antibodies site-specifically modified at an Fc-glycan can be prepared using the SITE-CLICK labeling products available from Thermo Fisher Scientific. For some applications, it can be advantageous to remove unreacted DIBO-derivatized polymer from a reaction mixture. In such applications, azide-derivatized resins can be used to remove excess particles from conjugation mixtures.

It is known that non-specific binding of biomolecules on the surface of fluorescent nanoparticles can interfere with attachment of target molecules to the particle surface and can cause optical artifacts (e.g., high background signal) that can interfere with accurate signal detection in biological imaging and flow cytometry assays. Surprisingly, fluorescent particles including a combination of fluorescent and non-fluorescent hydrophobic polymer (e.g., polystyrene) within the core can exhibit far less background signal than exhibited by fluorescent particles lacking additional hydrophobic polymer within the core. However, to further combat non-specific binding, additional components (e.g., blocking agents) optionally can be added to the sample to improve sensitivity (i.e., improve signal-to-noise ratio) of an assay by reducing background signal. Ideally, the blocking agent will bind to all potential sites of nonspecific interaction, eliminating background altogether, without altering or obscuring signal from the target molecule.

Representative examples of blocking agents include both non-ionic and charged water-soluble polymers, detergents (i.e. surfactants), carbohydrates and proteins. Representative examples of water soluble polymers include polyoxyalkylene such as polyalkylene glycol (e.g., a PEG), polypropylene glycol, polyvinylpyrrolidone, polyvinyl alcohol, polyzwitterions and the like. Representative examples of detergents that can be utilized as blocking agents include a non-ionic detergent or surfactant, such as, e.g., TRITON X-100 (Dow Chemical Company, Midland, Mich.), TWEEN 20 or TWEEN 80 (Croda Americas LLC, Wilmington, Del.), a Brij detergent, and the like. Zwitterionic detergents such as sulfobetaines, carboxybetaines such as CHAPS and the like. Representative examples of proteins that can be utilized as blocking agents include BSA, casein, serum solution, milk proteins, gelatin, and the like. Representative examples of carbohydrates that can be utilized as blocking agents include, for example, dextran, amylose, glycogen, and the like. Further, the sample solution can include additional components, such as antioxidants to minimize photodegradation of the fluorescent nanoparticles and preservatives to prevent bacterial growth (e.g., sodium azide).

After sufficient time for a particle to complex with target molecules in the sample, the sample is excited with a light source (e.g., a laser). Due to its optical properties, the particle can emit a fluorescence signal upon excitation at an appropriate wavelength of light. Excitation can be achieved using a light source such as a laser providing photons having a wavelength that falls within the absorption wavelength range of the compound (e.g., 350-650 nm). The sample can be contacted with the fluorescent particles under conditions and for a time sufficient to allow the particles to associate with or bind to the target molecule, if present, using methods that are known to those skilled in the art. The particles are typically present in a concentration sufficient to yield a detectable optical response under the desired conditions (e.g., about 1 µg/mL to about 150 µg/mL). The method can further include an optional washing step using methods known to those skilled in the art to remove unbound particles and other reagents from the particle-bound target molecule. At any time after or during treatment of the sample with the particle, the sample is illuminated with a wavelength of light selected to give a detectable optical response, and observed with a means for detecting the optical response. Any suitable instrument and technique known to those skilled in the art can be used to excite the fluorescent polymer and detect the emitted light. Equipment that is useful for illuminating fluorescent particles includes, but is not limited to, hand-held ultraviolet lamps, mercury arc lamps, xenon lamps, lasers and laser diodes. These illumination sources are optionally integrated into flow cytometers, laser scanners, fluorescence microplate readers, fluorometers, or chromatographic detectors. Certain particles provided herein are excitable at or near wavelengths in regions that closely match the output of standard equipment. For example, for flow cytometry and imaging experiments, it is common to excite the sample using a violet laser (i.e. ~405 nm) although excitation lasers that emit light beyond 405 nm also can be used.

Detection of the light emitted from the particles indicates the presence of the target molecule in the sample. The optical response can be detected by visual inspection, or by devices such as CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is analyzed using a flow cytometer, examination of the sample, optionally, can further include sorting portions of the sample according to their fluorescence response. Methods for detecting the presence of target molecules in a sample can further include quantification of the detected target molecules.

Detection of target molecules in a sample can be accomplished using, e.g., flow cytometry analysis or imaging. For flow cytometry assays, the particles can be added to the buffer or media containing living cells, incubated, and data acquired without washing the dye out of the sample. To ensure analysis is performed on living cells, a dead cell dye or a live cell dye can be included in the testing for gating out of dead cells or gating on living cells. For imaging, the particles are combined with a sample (e.g., a biological fluid or a sample of cells) that contains or is thought to contain target molecules to form a mixture. The solution is incubated for a sufficient amount of time for the particle to associate with the target molecule in the sample (about 5 minutes to 15 minutes to one hour or more). The incubated sample is then illuminated with an appropriate wavelength of light to generate a detectable optical response resulting from the presence of a complex of the compound with a target molecule in the sample. Illumination may be achieved by the use of a laser diode laser, mercury arc lamp or other such focused light source. The optical response can be detected to determine presence and location of target molecules in the sample and may be achieved using detection methods well known to those skilled in the art. Detection may be achieved by imaging to determine the presence and location of target molecules in a sample. In one embodiment, labeled particles and nuclei can be used for instrument set-up and calibration purposes (e.g., set-up and calibration of an instrument).

In certain methods, fluorescent particles provided herein can be used to label cells (e.g., flow cytometry or cell imaging experiments). The method can include contacting a cell with the fluorescent particle or a conjugate thereof for a time sufficient to allow the particle or conjugate to bind to the surface of the cell or enter into the cell. In certain methods, the affinity molecule (e.g., an antibody) can bind to a target molecule (e.g., cell surface protein) on the surface of the cell. Thus, also provided herein is a cell that includes a fluorescent particle or conjugate. The particle or conjugate can reside within the cytoplasm or nucleus of the cell, on or within a portion of the cell membrane, or is associated with the surface of the cell.

The particles and conjugates disclosed herein can be incorporated into kits that facilitate the practice of various assays. For example, kits are provided for use in biological experiments (e.g., cell imaging and flow cytometry). The kits can be packaged with the particles in a dry form or with the compound in solution. The kits can optionally further include one or more buffering agents, typically present as an aqueous solution, sample preparation reagents, blocking agents, anti-oxidants, additional detection reagents, organic solvent, other fluorescent detection probes, standards, microspheres, specific cell lines, antibodies and/or instructions for carrying out an assay. Additional optional agents include components for testing of other cell functions in conjunction with the compound. Also provided is a kit for labeling cells that includes a conjugate of a fluorescent particle and an affinity molecule that is capable of binding to a target molecule located in a cell, within a portion of the extracellular membrane or on the surface of a cell; and instructions for labeling the cell and detecting the conjugate labeled cell. In another embodiment, a kit for detecting a target molecule in a sample is provided that includes a conjugate, as disclosed herein, wherein the ligand is capable of binding to a target molecule in a sample, if present; and instructions for binding the target molecule to the conjugate and detecting the labeled target molecule.

The following examples are included to demonstrate certain embodiments of the invention. It should be appreciated by those of skill in the art that the techniques disclosed in the examples which follow represent techniques discovered by the inventor(s) to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

The examples provided herein utilize the following general methods unless indicated otherwise. Particles were formulated using a confined impinging jet mixer with two inlets. Hydrodynamic mean diameter (HD) and particle distribution (PdI) were determined via dynamic light scattering (DLS) using a Malvern-Zetasizer Nano Series DLS detector with a laser operating at $\lambda=531$ nm or 632.8 nm, an avalanche photodiode detector with high quantum efficiency and an ALV/LSE-5003 multiple $\tau$ digital correlator electronics system. All nanoparticle (NP) solutions were filtered with a PALL ACRODISC 0.2 µm SUPOR membrane syringe filter (Pall Corp., Port Washington, N.Y.) and diluted 4 to 5-fold into deionized (DI) water prior to all DLS measurements. Molecular weights for polymers are reported as the number average molecular weight ($M_n$), as measured using standard gel permeation chromatography (GPC) methods, using polystyrene standards with THF as an eluent with a Waters UV-vis photo diode array (PDA) detector. The 400 nm wavelength was used to analyze synthesized polymers. Fluorescence spectra were collected in either THF or aqueous solution at room temperature using excitation wavelengths of 405, 488, 561 or 633 nm. UV-Vis spectra and molar extinction coefficients were measured using an Agilent 8453 UV-Vis Spectrophotometer. Nanoparticles were diluted 1500 fold into DI water for fluorescence excitation and emission spectra and recorded on a LS 45 Fluorescence Spectrometer or a TECAN plate reader. Fluorescent quantum yield (QY) was measured in aqueous solution at room temperature using a Hamamatsu absolute PL quantum yield measurement system with excitation wavelengths of 405, 488, 561 or 633 nm. Energy transfer efficiency was estimated by comparing the ratio of peak fluorescence intensity (PFI) of the energy acceptor emission to the sum of the peak fluorescence intensity of the energy acceptor emission and energy donor emission according to the following equation:

$$\text{Energy transfer efficiency}(\%) = \frac{\text{Acceptor emission } PFI}{\text{Acceptor emission } PFI + \text{Donor emission } PFI} \times 100 \quad \text{(Equation 1)}$$

Example 1

Preparation of PFO/PS-b-PEG Particles in Phosphate Buffer Solution

Fluorescent particles were prepared using two different shell polymer compositions. 3.3 mg of poly(9,9-dioctylfluorenyl-2,7-diyl) (PFO; $M_n$=28,700 g/mol) (Sigma-Aldrich Corp., St. Louis, Mo.), 4.43 mg of poly(styrene)-block-poly(ethylene glycol) (PS-b-PEG; $M_n$=3900 g/mol) copolymer (Polymer Source, Dorval, Quebec), 2.27 mg PS-b-PEG ($M_n$=6600 g/mol) copolymer (Polymer Source) were dissolved in 1 mL of tetrahydrofuran (THF) (Sample 1). 2.0 mg of the same PFO material, as described for Sample 1, 2.65 mg of PS-b-PEG ($M_n$=3900 g/mol) copolymer and 1.35 mg of PS-b-PEG ($M_n$=6600 g/mol) copolymer were dissolved in 1 mL of THF (Sample 2). Upon complete dissolution of polymers, the THF solution in Sample 1 or Sample 2 was rapidly mixed with an equivalent volume of aqueous phosphate buffer saline (PBS), pH 7.4, using a confined impinging jet mixer with two inlets. Impingement and homogenous mixing of the streams formed nanoparticles through controlled nanoprecipitation. The combined streams exiting the mixer were immediately introduced to 8 mL of PBS resulting in a final THF:PBS water volume ratio of 1:9. THF was subsequently removed via rotary evaporation and/or dialysis against aqueous PBS to form a solvent free, aqueous NP solution. The NP HD and PdI were 90 nm and 0.11 for Sample 1 and 65 nm and 0.09 for Sample 2, respectively. Fluorescence measurements of the particles revealed a blue shift in the excitation spectra and a red shift in the emission spectra, relative to PFO in THF, indicating successful encapsulation and aqueous dispersion of PFO by the amphiphilic copolymers (PS-b-PEG).

Example 2

Preparation of PFO/PS/PS-b-PEG Particles in Phosphate Buffer Solution

Fluorescent nanoparticles were formulated with a hydrophobic fluorescent polymer and non-fluorescent hydrophobic polymer in the core. 1.0 mg of PFO ($M_n$=97,000 g/mol) (American Dye Source, Inc., Baie d'Urfé, Quebec), 1.0 mg of polystyrene (PS) ($M_n$=1700 g/mol; Polymer Source), 3.56 mg of PS-b-PEG ($M_n$=3900 g/mol) copolymer and 0.44 mg of PS-b-PEG ($M_n$=9200 g/mol) copolymer (Polymer Source) were dissolved in 1 mL of THF. Upon complete dissolution, the THF solution was rapidly mixed with an equivalent volume of aqueous PBS, at pH 7.4, using a confined impinging jet mixer as described in Example 1. The NP HD and PdI were 46 nm and 0.11, respectively (Sample 3). Fluorescence measurements of the particles revealed a blue shift in excitation and a red shift in emission spectra, relative to PFO in THF, indicating successful encapsulation and aqueous dispersion of PFO and PS by the amphiphilic copolymers (PS-b-PEG).

Example 3

Preparation of Particles with Different Hydrophobic Polymer Core Ratios

This example demonstrates the ability to modulate the mean hydrodynamic diameter of particles by varying the hydrophobic fluorescent polymer to non-fluorescent hydrophobic polymer weight ratio. The weight ratio of fluorescent hydrophobic polymer (PFO) and non-fluorescent hydrophobic polymer (PS) was varied from 1:0 to 1:9 with the total core weight of each sample equating to 2.0 mg. PFO ($M_n$=69,000 g/mol) (American Dye Source), PS ($M_n$=1700 g/mol; Polymer Source) and 4 mg total PS-b-PEG (3.56 mg PS-b-PEG ($M_n$=3900 g/mol) copolymer and 0.44 mg of PS-b-PEG ($M_n$=9200 g/mol) copolymer (Polymer Source)) were dissolved in 1 mL of THF. All NP samples were formulated and isolated as described in Example 1, and NPs were narrowly and homogenously dispersed in DI water, as determined by DLS. Surprisingly, NP HDs decreased from 55 to 35 nm as the amount of PS increased and PFO decreased (see, FIG. 1). Because both the PFO and PS materials used for each NP sample were the same (i.e., same molecular weight and lot of material), changes in NP size were solely due to changes in the ratio of PFO to PS. The decrease in particle HD with increasing PS content was unforeseen and contrary to what would have been expected as a result of increasing the amount of hydrophobic material in the core. Excitation and emission spectra were essentially identical for each sample with the exception that NP emission fluorescent intensity increased as PFO content per particle increased. The results demonstrate that addition of PS not only reduces NP size, but also allows for accurate control of the amount of fluorophore loaded into the NP. Precise control the amount of fluorophore contained in the particle can be advantageously used to tailor signal intensity for a population of NPs.

Example 4

Figure 2:
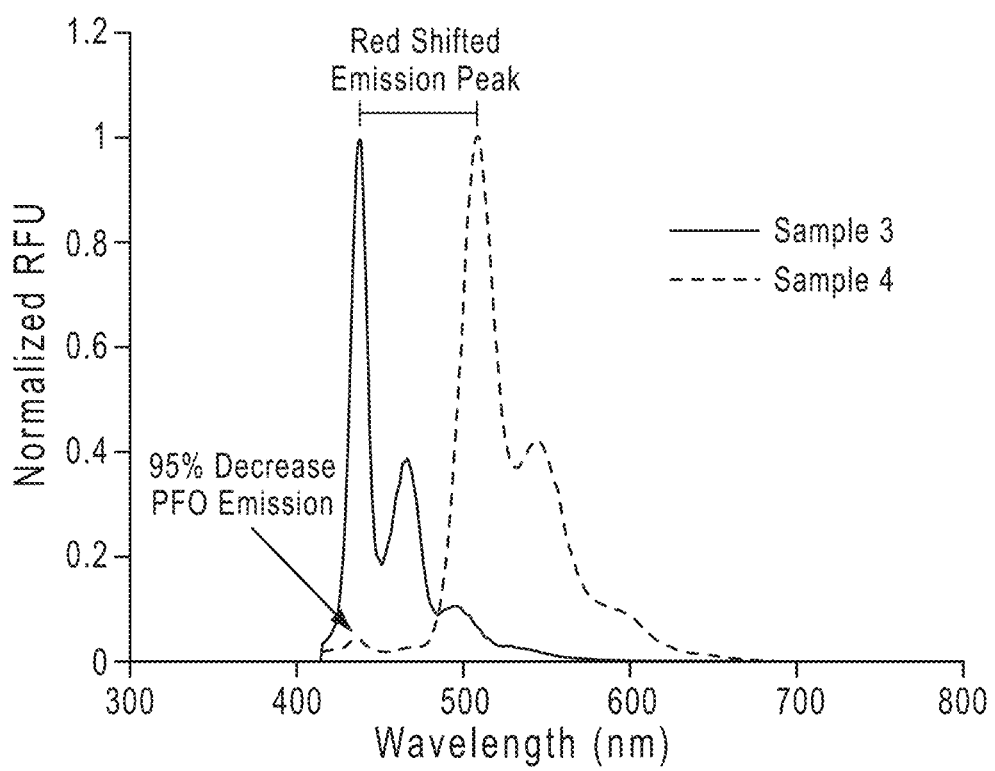
FIG. 2 is a plot showing the change in the emission peak maximum for NPs prepared using PFO (Sample 3) or a mixture of PFO and PFPV (Sample 4) as the hydrophobic fluorescent polymer, upon excitation at 405 nm

Preparation of Particles with Multiple Hydrophobic Fluorescent Copolymers in the Core Fluorescent particles were prepared using a mixture of hydrophobic, fluorescent polymers that exhibited Förster Resonance Energy Transfer (FRET) upon excitation at 405 nm. NPs were prepared and isolated, as described in Example 1, using a mixture of PFO and (poly[(9,9-dioctylfluorenyl-2,7-diyl)-alternating-(2-methoxy-5-(2-ethylhexyloxy)-1,4-phenylene)]) (PFPV) (Sample 4). NPs were prepared by dissolving 1.8 mg of PFO ($M_n$=28,700 g/mol) (Sigma-Aldrich Corp.), 0.2 mg of PFPV ($M_n$=53000 g/mol) (American Dye Source, Inc.), 2.52 mg of PS-b-PEG ($M_n$=3900 g/mol) copolymer and 1.48 mg of PS-b-PEG ($M_n$=9200 g/mol) copolymer in 1 mL of THF. NP HD and PdI were 57 nm and 0.09, respectively. Comparing Sample 3 to Sample 4 (FIG. 2) the maximum emission at 439 nm for Sample 3 decreased 95% when PFPV was added, and the emission wavelength maximum red-shifted from 439 nm for Sample 3 to 508 nm for Sample 4, resulting from highly efficient energy transfer between donor and acceptor fluorophore. Efficient energy transfer indicated that PFO and PFPV were homogenously mixed within the NP core, consistent with their having similar solubility parameters, such that they are miscible. Due to the high FRET efficiency and lack of undesired donor (PFO) emission, this NP system can be advantageously implemented in applications using multiple fluorescent detection reagents that can be excited at the same wavelength but have different maximum emission wavelengths.

Example 5

Synthesis of $(PFO)_{xn}$-co-$(NH_2—PF)_{yn}$ Copolymer

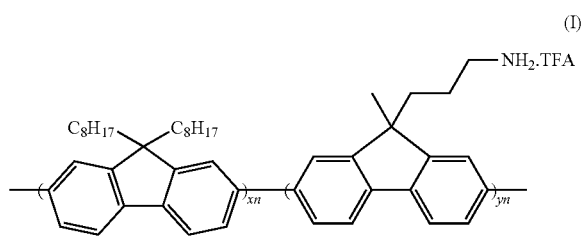

(I)

Hydrophobic fluorescent polymers with primary amine pendant groups for conjugation reactions can be synthesized from poly[(9,9-dioctylfluorenyl-2,7-diyl)$_{xn}$-co-(tert-butyl-4-(2,7-dibromo-9-methyl-9H-fluoren-9-yl)propylcarbamate)$_{yn}$] (($PFO)_{xn}$-co-(t-Boc-PF)$_{yn}$), where x and y refer to mol % monomer in the polymerization reaction and n refers to the degree of polymerization, or number of repeat units (Compound I). The synthesis of (($PFO)_{0.97n}$-co-(t-Boc-PF)$_{0.03n}$) copolymer is described. 9,9-Dioctyl-9H-fluorene-2,7-diboronic acid bis(pinacol) ester (437 mg, 0.68 mmol), 9,9-dioctyl-2,7-dibromofluorene (350 mg, 0.639 mmol), tert-butyl-4-(2,7-dibromo-9-methyl-9H-fluoren-9-yl)propylcarbamate (20 mg, 0.04 mmol; t-Boc-PF), 0.5 mL of N-Methyl-N,N,N-trioctylammonium chloride (Aliquat 336), and 20 mL of toluene were placed in a 100 mL 2-neck round-bottom flask. The reagent mixture was carefully degassed through 3 cycles of freeze-pump-thaw (pump for 10 min, 5 min and 5 min). After the last cycle, the flask was refilled with argon. Under argon, Pd(PPh$_3$)$_4$ (12 mg, 0.01 mmol) and 7 mL of 2 M degassed Na$_2$CO$_3$ aqueous solution were added. The reaction mixture was heated at 80° C. overnight (18 h) with vigorous stirring. The upper organic layer was poured into 300 mL of MeOH/H$_2$O (10/1), filtered, and washed with water and methanol. The precipitate was dried in a vacuum oven to obtain a green-grey fibrous copolymer (540 mg); GPC M$_n$=32,400 g/mol, PDI=2.4. For t-Boc deprotection, the resulting copolymer (500 mg, 15.4 nmol) was dissolved in 20 mL anhydrous dichloromethane (DCM) and 2.5 mL of trifluoroacetic acid was added into the solution and stirred overnight. The solution was diluted with 10 mL toluene and evaporated to dryness. The polymer product then was dissolved in 20 mL THF and precipitated in methanol (300 mL). The final powder was collected by filtration and dried in a vacuum oven to obtain the green-grey fibrous $(PFO)_{0.97n}$-co-$(NH_2—PF)_{0.03n}$ polymer (480 mg, 96%).

Example 6

Conjugation of BODIPY Dye Derivatives to $(PFO)_{xn}$-co-$(NH_2—PF)_{yn}$ Copolymers To prepare hydrophobic fluorescent copolymers with FRET capabilities, BODIPY dyes with reactive ester groups were covalently attached to pendant primary amine groups of $(PFO)_{xn}$-co-$(NH_2—PF)_{yn}$ copolymers. For example, BODIPY 493/503 NHS Ester (succinimidyl ester) (Thermo Fisher Scientific) (25 mg, 60 nmol) and $(PFO)_{0.97n}$-co-$(NH_2—PF)_{0.03n}$ copolymer (480 mg, 14.8 nmol), as described in Example 5, were dissolved in 15 mL anhydrous THF followed by addition of 1.5 mL N,N-diisopropylethylamine. This was stirred and reacted at room temperature overnight. The product was precipitated in methanol (200 mL). The resulting hydrophobic, fluorescent polymer was collected by filtration and washed with methanol three times. The final product was dried in a vacuum oven to obtain a yellow fibrous copolymer $(PFO)_{0.95n}$-co-(PF-BODIPY 493/503)$_{0.03n}$ (M$_n$=27,400 g/mol; 470 mg, 98%) (Polymer 1). Hydrophobic fluorescent copolymers were prepared similarly using the method described herein but incorporating the NHS ester form of commercially available BODIPY dyes (Thermo Fisher Scientific): BODIPY 493/503 at 5 mol % (Polymer 2), BODIPY FL at either y=5 mol % (Polymer 3) or 20 mol % (Polymer 4), respectively, 5 mol % BODIPY 576/589 (Polymer 5) and 10 mol % BODIPY 581/591 (Polymer 6).

Example 7

Preparation of FRET NPs with Polymer 2/PS/PS-b-PEG Copolymers

FRET-capable NPs were formulated using the hydrophobic fluorescent copolymers described in Example 6. For example, 1.0 mg of Polymer 2 (M$_n$=17,400 g/mol), 1.0 mg of PS (1700 g/mol) (Polymer Source), 3.56 mg of PS-b-PEG (M$_n$=3900 g/mol) copolymer and 0.44 mg of PS-b-PEG (M$_n$=9200 g/mol) copolymer (Polymer Source) were dissolved in 1 mL of THF. NPs including 50% by weight polystyrene were formulated and isolated as described in Example 1. The NP mean HD and PdI, measured via DLS, were 37 nm and 0.11, respectively (Sample 5). Additional FRET-capable NP samples with similar HD and PdI were prepared as described herein but using Polymer 1 (BODIPY 493/503 3 mol %) (Sample 6), Polymer 3 (BODIPY FL 5 mol %) (Sample 7), Polymer 4 (BODIPY FL 20 mol %) (Sample 8), Polymer 5 (BODIPY 576/589 5 mol %) (Sample 9), and Polymer 6 (BODIPY 581/591 10 mol %) (Sample 10). Optical properties for each sample are listed in Table 3 (see, Example 27).

Example 8

Preparation of FRET NPs with Polymer 1 and PS at Different Weight Percent Ratios NPs with $(PFO)_{0.97}$-co-(PF-BODIPY 493/503)$_{0.03}$ (M$_n$=27,400 g/mol; Polymer 1) were formulated and characterized, as described in Example 1, using different weight ratios of hydrophobic fluorescent polymer to PS (M$_n$=1700 g/mol) (Polymer Source). NPs were prepared using a weight ratio of Polymer 1 to PS of 1:3 (Sample 11) and 3:1 (Sample 12). For each sample, 2.0 mg of core material (fluorescent hydrophobic polymer and PS), 3.17 mg of PS-b-PEG ($M_n$=3900 g/mol) copolymer and 0.83 mg of PS-b-PEG ($M_n$=9200 g/mol) copolymer (Polymer Source) were dissolved in 1 mL of THF. As was the case with NPs prepared in Example 3, HD decreased as PS content increased. HD and PdI were 39 nm and 0.06 for Sample 11 and 48 nm and 0.07 for Sample 12. In addition to affecting NP size, QY increased from 0.57 to 0.68 as PS content in the core increased (see, Table 3). This data shows that QY, which contributes to fluorescent brightness, can be manipulated with changes in weight percent ratio of fluorescent and non-fluorescent hydrophobic polymers in the core of the particle.

Example 9

Energy Transfer Efficiency Enhancement for NPs Formulated with Polymer 1

Energy transfer efficiency was measured for Polymer 1 dissolved in THF using an excitation wavelength of 405 nm. Upon excitation, ~50% energy transfer efficiency from PFO to BODIPY 493/503 was observed. Efficiency was estimated by comparing the ratio of peak intensity of the BODIPY 493/503 acceptor dye emission at 507 nm over the sum of the peak intensity of the acceptor emission plus PFO donor emission at 417 nm. QY of Polymer 1 in THF was 0.76.

NPs incorporating Polymer 1 were formulated and isolated as described in Example 1 using 1.5 mg of Polymer 1 ($M_n$=27,400 g/mol), 0.5 mg of polystyrene (PS) (1700 g/mol) (Polymer Source), 3.56 mg of PS-b-PEG ($M_n$=3900 g/mol) copolymer and 0.44 mg of PS-b-PEG ($M_n$=9200 g/mol) copolymer (Polymer Source) (Sample 13). The NP's included 25 wt. % polystyrene. The HD and PdI for the NPs were 47 nm and 0.11, respectively. QY of Polymer 1 in NPs was 0.54. The reduction in QY for the NPs was consistent with the expected quenching that results from condensing fluorescent polymers into particulate form. Upon packaging Polymer 1 into aqueous-dispersible NPs, the energy transfer efficiency increased to 98% (see, Table 4; Example 28), an almost 2-fold enhancement in energy transfer from PFO to the covalently attached BODIPY 493/503.

Figure 3:
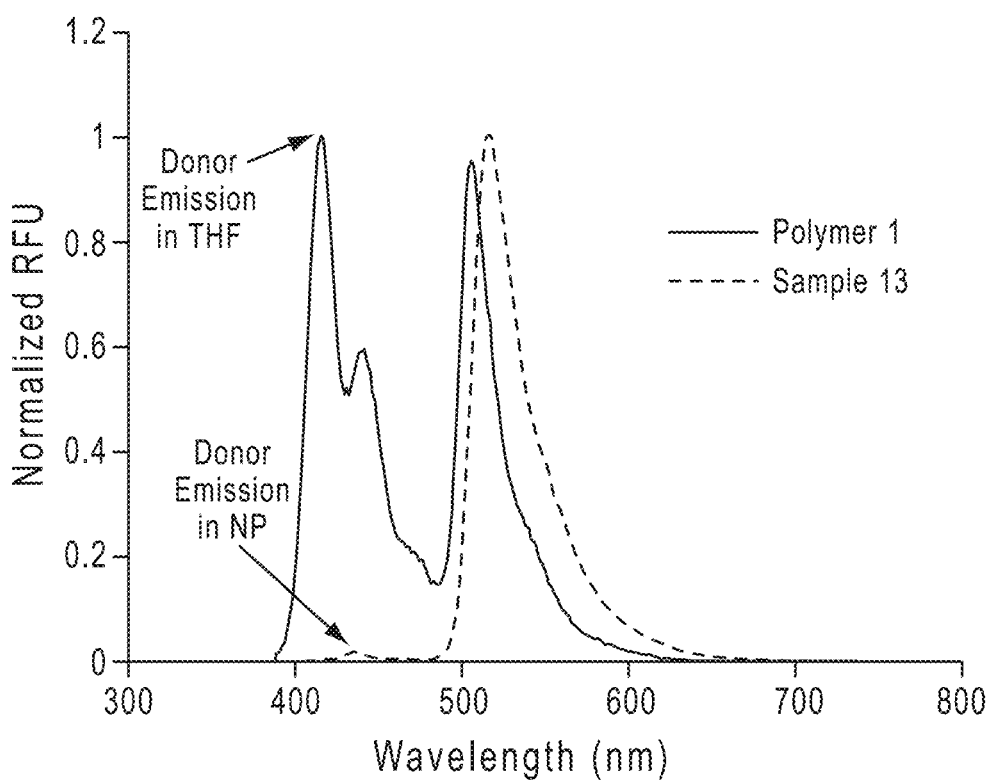
FIG. 3 is a plot showing fluorescent emission of Polymer 1 in THF and formulated into water-dispersible NPs (Sample 13, upon excitation at 405 nm FIG. 4 is a plot showing the emission profiles of NPs prepared using two different mol % of BODIPY-FL (Sample 7 and Sample 8).

Energy transfer of PFO emission to BODIPY 493/503 for Polymer 1 in NPs exhibited a dramatic and unanticipated enhancement in efficiency relative to the energy transfer exhibited for Polymer 1 in THF solution. In addition, upon condensation into particulate form, the excitation peak of Polymer 1 shifted from 390 nm (THF) to 380 nm (NPs), PFO donor emission shifted from 417 nm to 439 nm, and the BODIPY 493/503 acceptor emission shifted from 507 nm to 517 nm (FIG. 3). The enhanced energy transfer experienced by Polymer 1 when contained within a NP, relative to when dissolved in THF solution, allows for the possibility of using less acceptor dye in the FRET-capable polymer, while still efficiently quenching donor emission. Because less acceptor dye needs to be included in the polymer, fluorescent interference from the acceptor dye can be significantly reduced. Reduction in fluorescent interference is especially advantageous in applications requiring multiple excitation sources that can excite both the donor and acceptor fluorophores (e.g., in flow cytometry).

Figure 4:
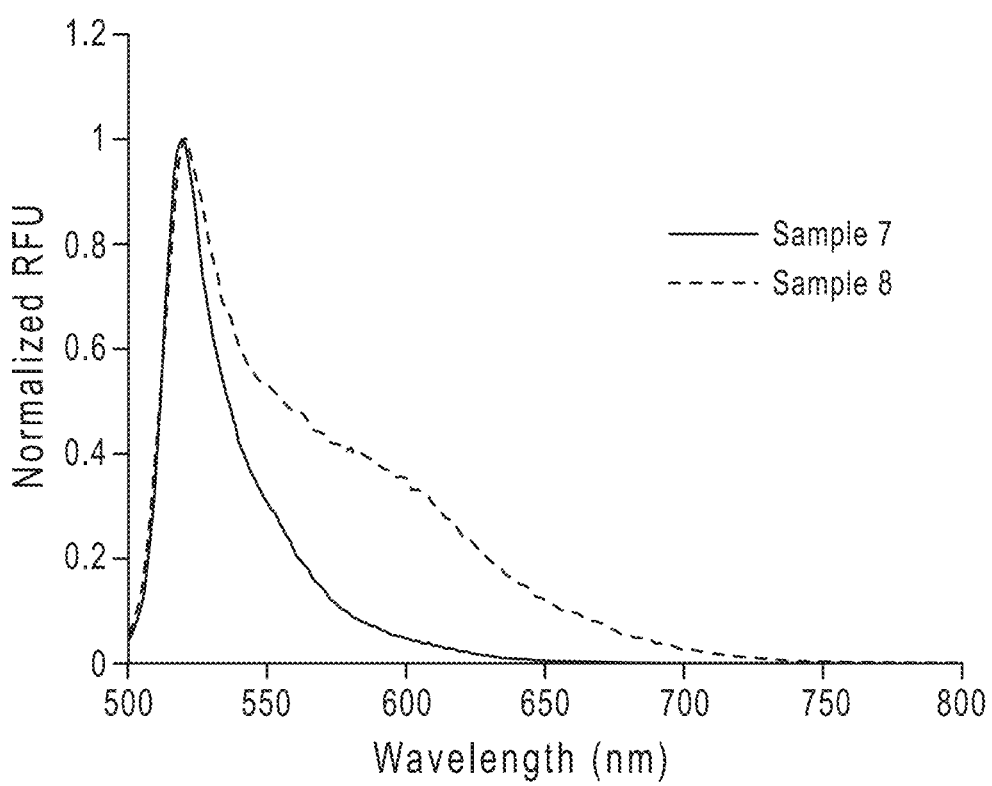

Enhancement in energy transfer efficiency was also measured for Polymer 2-6 in THF and in particulate form (Sample 5, Sample 7, Sample 8, Sample 9, and Sample 10). Referring to Table 4, Polymer 2-6 experienced an increase in FRET efficiency when contained in particulate form. For certain samples, the FRET efficiency increased by 30% or greater. Sample 8 (20 mol % BODIPY-FL) exhibited slightly higher energy transfer efficiencies in both THF and NP's than Sample 7 (5 mol % BODIPY-FL), likely due to the higher mol % conjugation of BODIPY-FL. Although energy transfer was higher, the emission profile of Sample 8 was much broader than that of Sample 7 (FIG. 4). This increased broadness was attributed to the presence of more BODIPY-FL dyes within the particle. The data from Samples 5 and 7-10 demonstrates narrow fluorescent emission profiles and high energy transfer efficiencies (e.g., >90%) can be effectively achieved using dye conjugations of 5 mol % or less, while higher levels of dye conjugation (e.g., 20 mol % or more) can result in broadening of the emission peak. In addition, this data indicates that emission profiles can be manipulated by changing the type and/or amount of conjugated small molecule fluorescent dyes on the polymer. This attribute of the disclosed FRET-capable polymers is particularly advantageous if multiple unique emission profiles are needed such as, e.g., for cell fluorescent barcoding applications.

Example 10

Synthesis of $(PFO)_{xn}$-co-$(PBT)_{yn}$-co-$(NH_2-PF)_{zn}$ Copolymer

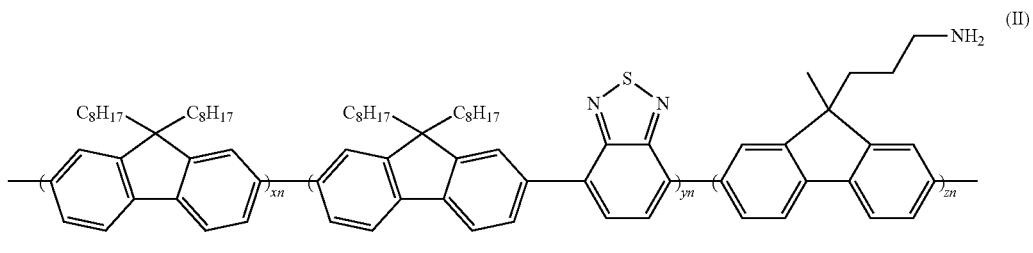

(II)

Hydrophobic fluorescent polymers capable of 2-step FRET can be synthesized using a method similar to that described in Example 5, where the polymers can include pendant reactive amine groups for higher wavelength emissions and conjugation (Compound II). Described herein is the synthesis of poly[(9,9-dioctylfluorenyl-2,7-diyl)$_{xn}$-co-(4,7-dibromobenzo[c][1,2,5]thiadiazole)$_{yn}$-co-(tert-butyl-4-(2,7-dibromo-9-methyl-9H-fluoren-9-yl) propylcarbamate)$_{zn}$] (($PFO)_{xn}$-co-$(PBT)_{yn}$-co-$(NH_2-PF)_{zn}$) copolymer, where x, y and z refer to mol % monomer in the polymerization reaction and n refers to the degree of polymerization, or number of repeat units. 9,9-dioctyl-9H-fluorene-2,7-diboronic acid bis(pinacol) ester (437 mg, 0.68 mmol), 9,9-dioctyl-2,7-dibromofluorene (350 mg, 0.639 mmol), 4,7-dibromobenzo[c][1,2,5]thiadiazole (8 mg, 0.0272 mmol), tert-butyl-4-(2,7-dibromo-9-methyl-9H- fluoren-9-yl)propylcarbamate (6.7 mg, 0.0136 mmol), 5 drops of Aliquat 336, and 20 mL of toluene were placed in a 100 mL 2-neck round-bottom flask. The reagent mixture was carefully degassed through 4 cycles of freeze-pump-thaw and after the last cycle the flask was refilled with argon. Pd(PPh$_3$)$_4$ (12 mg, 0.01 mmol) and 7 mL of 2 M degassed Na$_2$CO$_3$ aqueous solution were added under argon. The reaction mixture was heated overnight at 80° C. with vigorous stirring. The upper organic layer was poured into 300 mL of MeOH/H$_2$O (10/1), filtered, and washed with water and methanol. The precipitate was dried in a vacuum oven to obtain a yellow fibrous copolymer (560 mg); M$_n$=27500 g/mol, PDI=2.0. For t-Boc deprotection, the resulting copolymer (60 mg, 2.2 nmol) was dissolved in 3 mL anhydrous DCM, followed by adding 0.3 mL of trifluoroacetic acid into a solution and stirring overnight. The solution was diluted with 10 mL toluene and evaporated to dryness. The polymer product was then dissolved in 2 mL THF and precipitated in methanol (30 mL). The final powder was collected by filtration, and dried in a vacuum oven to obtain a yellow fibrous copolymer (PFO)$_{0.97n}$-co-(PBT)$_{0.02n}$-co-(NH$_2$—PF)$_{0.01n}$ (45 mg, 75%).

Example 11

Conjugation of BODIPY Dye Derivatives to (PFO)$_{xn}$-co-(PBT)$_{yn}$-co-(NH$_2$-PF)$_{zn}$ To prepare hydrophobic fluorescent copolymers with 2-step FRET capabilities, BODIPY dyes with reactive ester groups were covalently attached to pendant primary amine groups of (PFO)$_{xn}$-co-(PBT)$_{yn}$-co-(NH$_2$—PF)$_{zn}$ copolymers, prepared as described in Example 10. For example, BODIPY 576/589 NHS Ester (Succinimidyl Ester) (1 mg, 2.3 nmol; Thermo Fisher Scientific) and (PFO)$_{0.97n}$-co-(PBT)$_{0.02n}$-co-(NH$_2$—PF)$_{0.01n}$ copolymer (45 mg, 1.6 nmol) were dissolved in 3 mL anhydrous THF, followed by adding 0.2 mL N,N-diisopropylethylamine. The reaction mixture was stirred overnight in the dark at room temperature, and the product was precipitated in methanol (30 mL). The copolymer was collected by filtration, and washed with methanol three times. The final product was dried in a vacuum oven to obtain a red fibrous hydrophobic fluorescent copolymer (PFO)$_{0.97n}$-co-(PBT)$_{0.02n}$-co-(PF-BODIPY 576/589)$_{0.01n}$ (M$_n$=27,500 g/mol; 35 mg, 78%) (Polymer 7). Hydrophobic fluorescent copolymers were prepared using a method as described for Polymer 7 that incorporated BODIPY 576/589 at 8 mol % (Polymer 8), 5 mol % (Polymer 9) 3 mol % (Polymer 10) or 2 mol % (Polymer 11). Copolymers with z=5 mol % for BODIPY 530/550 (Polymer 12), BODIPY R6G (Polymer 13), BODIPY 630/650 (Polymer 14), and BODIPY 650/665 (Polymer 15) also were synthesized using similar methods. All BODIPY derivatives listed were purchased from Thermo Fisher Scientific as NHS esters and reacted to pendant amine groups, as described herein.

Example 12

Preparation of 2-Step FRET NPs with Polymer 9/PS/PS-b-PEG Copolymers

Several 2-step FRET NPs were formulated using hydrophobic fluorescent copolymers described in Example 11 and including 50% by weight PS. For example, 1.0 mg of PFO$_{0.93n}$-co-PBT$_{0.02n}$-co-(PF-BODIPY 576/589)$_{0.05n}$ (M$_n$=20,000 g/mol; Polymer 9), 1.0 mg of PS (M$_n$=1700 g/mol) (Polymer Source), 3.56 mg of PS-b-PEG (M$_n$=3900 g/mol) copolymer and 0.44 mg of PS-b-PEG (M$_n$=9200 g/mol) copolymer (Polymer Source) were dissolved in 1 mL of THF. NPs were formulated and isolated as described in Example 1. NP mean HD and PdI were 37 nm and 0.08, respectively (Sample 14). 2-step FRET-capable NP samples with similar HD and PdI also were prepared using the procedure described for Polymer 7 (Sample 15), Polymer 8 (Sample 16) Polymer 10 (Sample 17), Polymer 11 (Sample 18), Polymer 12 (Sample 19), Polymer 13 (Sample 20), Polymer 14 (Sample 21), and Polymer 15 (Sample 22). Optical properties for each of the materials are listed in Table 3. Lower QY levels for Sample 16-17 may have been the result of increased fluorescence quenching resulting from the increased BODIPY dye content in these samples.

Example 13

Preparation of 2-Step FRET NPs with Different Hydrophobic Core Ratios

This example demonstrates how the size and QY of particles including the same type of hydrophobic, fluorescent polymer can be systematically controlled by incorporating different amounts of a non-fluorescent hydrophobic polymer into particles. NPs were formulated and isolated, as described in Example 1, using different weight ratios of PS (M$_n$=1700 g/mol) (Polymer Source) to hydrophobic fluorescent polymer. PF$_{0.97n}$-co-PBT$_{0.02n}$-co-(PF-BODIPY 576/589)$_{0.01n}$ (M$_n$=40,000 g/mol) (Polymer 16) was synthesized as described in Example 10 and Example 11. Polymer 16 is a 2-step FRET-capable polymer. Upon irradiation at a first wavelength, PFO absorbs and transfers energy to PBT, and then PBT transfers energy to the covalently attached BODIPY 576/589, which then emits at a second wavelength. NPs with three different weight ratios of Polymer 16:PS were investigated: 1:3 (Sample 23), 1:1 (Sample 24), and 3:1 (Sample 25). For each sample, 2.0 mg of core material (PS plus Polymer 16), 1.19 mg of PS-b-PEG (M$_n$=3900 g/mol) copolymer and 2.81 mg of PS-b-PEG (M$_n$=9200 g/mol) copolymer (Polymer Source) were dissolved in 1 mL of THF. Similar to the particles prepared in Example 3 and 8, HD decreased as PS content increased. HD and PdI were 45 nm and 0.08 (Sample 23), 49 nm and 0.08 (Sample 24) and 55 nm and 0.08 (Sample 25). Referring to Table 3, the QY increased from 0.53 (Sample 25) to 0.60 (Sample 24) to 0.66 (Sample 23) as PS content by weight in the core increased from 25% to 75%. Because QY would be expected to scale inversely with fluorescent polymer concentration, it was not surprising that a NP containing a lower amount of fluorescent polymer would exhibit increased QY relative to a NP containing more fluorescent polymer overall. Interestingly, a decrease in QY occurred with increasing BODIPY dye concentration inside the NP.

Example 14

Energy Transfer Efficiency Enhancement NPs Formulated with Polymer 16

This example demonstrates the difference in energy transfer efficiency for Polymer 16 when dissolved in THF solution and when packaged into a NP. NPs containing Polymer 16 and 25 wt. % PS were formulated and isolated, as described in Example 1, with the following composition: 1.5 mg of Polymer 16 ($M_n$=40000 g/mol), 0.5 mg of polystyrene (PS) (1700 g/mol) (Polymer Source), 3.56 mg of PS-b-PEG ($M_n$=3900 g/mol) copolymer and 0.44 mg of PS-b-PEG ($M_n$=9200 g/mol) copolymer (Polymer Source) (Sample 26). NP HD and PdI were 52 nm and 0.07, respectively. QY was 0.71 (Polymer 16 dissolved in THF) and 0.59 (Sample 26).

Figure 5:
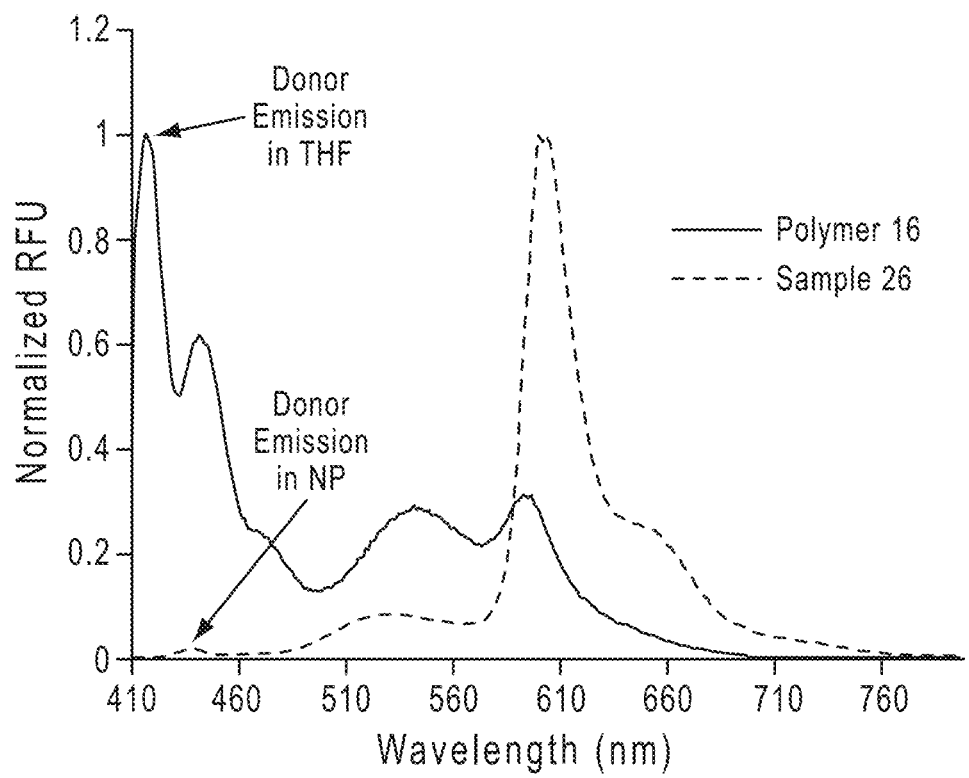
FIG. 5 is a plot showing the emission profile of Polymer 16 when dissolved in THF and when packaged into a NP in DI water (Sample 26).
Figure 6:
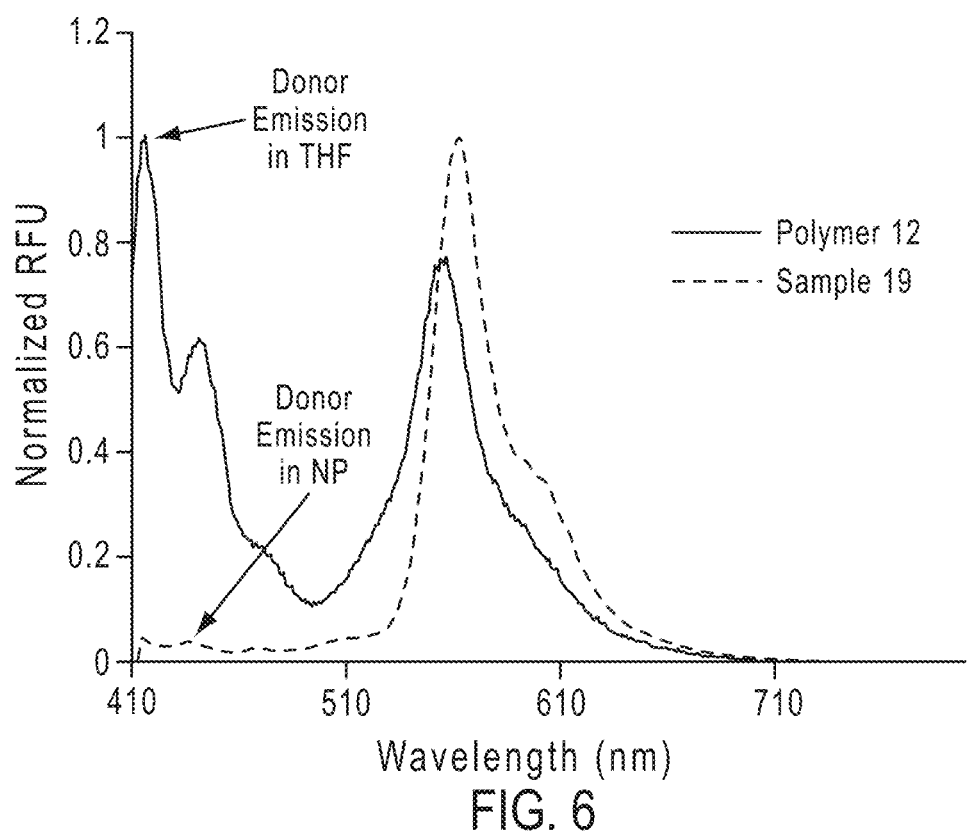
FIG. 6 is a plot showing the emission profile of Polymer 12 when dissolved in THF and when packaged into a NP in DI water (Sample 19).
Figure 7:
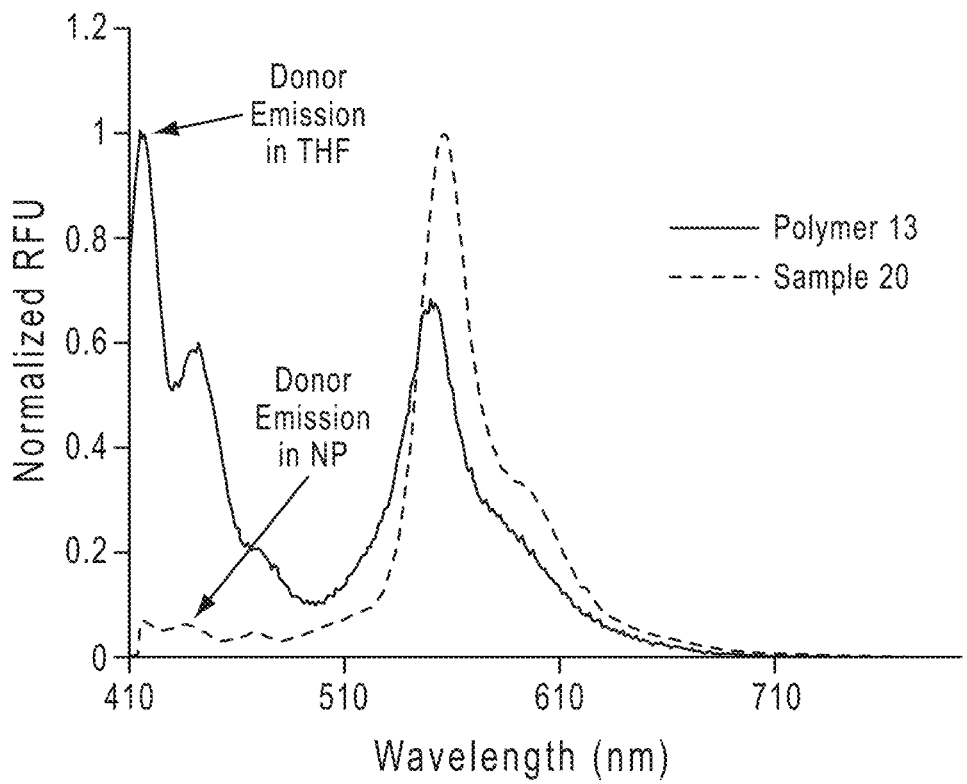
FIG. 7 is a plot showing the emission profile of Polymer 13 when dissolved in THF and when packaged into a NP in DI water (Sample 20).
Figure 8:
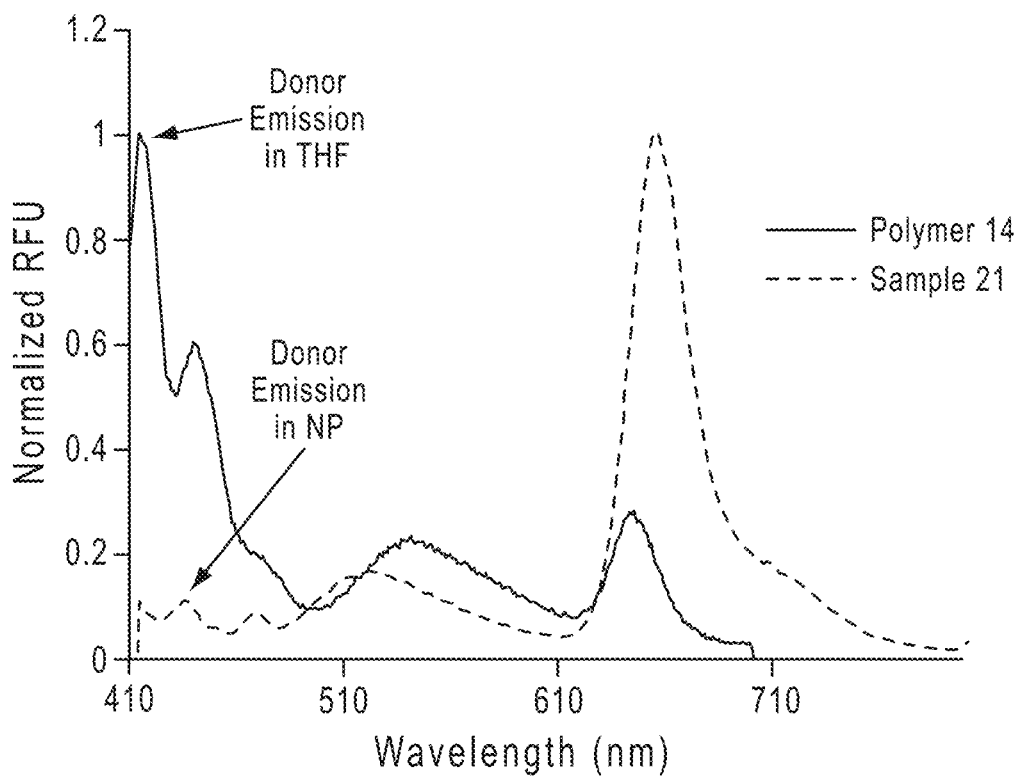
FIG. 8 is a plot showing the emission profile of Polymer 14 when dissolved in THF and when packaged into a NP in DI water (Sample 21).

Polymer 16 dissolved in THF was excited at 405 nm, resulting in ~24% energy transfer efficiency from PFO and PBT to BODIPY 576/589. Energy transfer efficiency was estimated by comparing the ratio of peak intensity of the BODIPY 576/589 acceptor dye emission at 593 nm over the sum of the peak intensity of the acceptor emission plus PFO donor emission at 417 nm. Upon packaging Polymer 16 into NPs, the energy transfer efficiency to BODIPY 576/589 increased to 98% in aqueous NPs (see, Table 4), a ~4-fold enhancement in energy transfer. Upon condensation into particulate form, the excitation peak of Polymer 16 in THF shifted from 391 nm to 377 nm, the PFO donor emission shifted from 417 nm to 439 nm, and the BODIPY 576/589 acceptor emission shifted from 593 nm to 603 nm (FIG. 5). A similar shift in emission peaks and enhancement in energy transfer efficiency also was detected for the following NP samples: Sample 19 (FIG. 6), Sample 20 (FIG. 7) and Sample 21 (FIG. 8). Energy transfer efficiencies for each of the samples prepared in this example are listed in Table 4. As discussed in Example 9, the observed enhancement in energy transfer efficiency experienced by fluorescent polymer, as disclosed herein, when packaged into water-soluble NPs has significant benefits.

Example 15

Comparison of 1-Step and 2-Step FRET NPs

Figure 9:
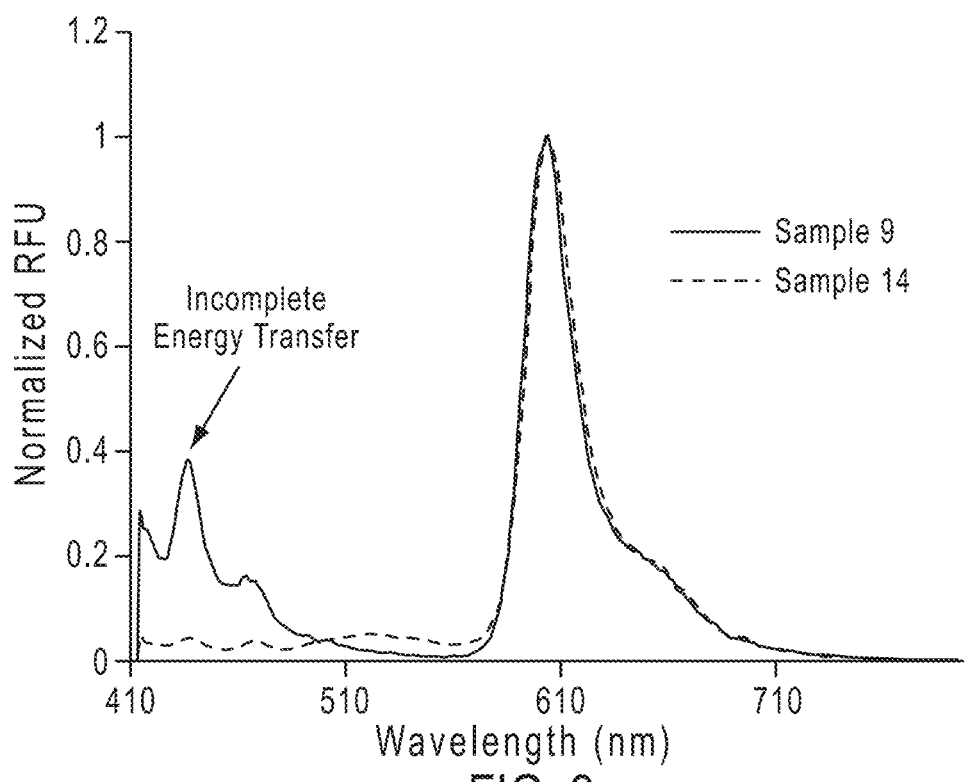
FIG. 9 is a plot comparing the emission profiles of a 1-step (Sample 9) and 2-step (Sample 14) FRET system.

A FRET system involving more than one energy transfer step can be advantageous for providing higher energy transfer efficiency, especially when there is little to no spectral overlap between the acceptor dye excitation spectrum and the emission spectrum of the donor dye. The advantage of a 2-step FRET system is demonstrated by comparing Sample 9 and Sample 14, where both NP samples use 5 mol % BODIPY 576/589 containing polymers as the acceptor fluorophore. In Sample 9, the fluorescent polymer in the core includes a backbone made up of only PFO monomer repeat units, while in Sample 14, the fluorescent polymer in the core includes a backbone formed of PFO and 2 mol % PBT monomer repeat units. The maximum emission peaks for PFO and PFO-co-PBT in nanoparticle form are 438 nm and 525 nm, respectively. As shown in FIG. 9, the energy transfer efficiency upon 405 nm excitation for Sample 9 is less than for Sample 14 (96%) (Table 4). This data demonstrates that a 2-step FRET polymer system can be particularly advantageous for achieving energy transfer efficiencies ≥90% when a small molecule acceptor dye having excitation maxima above ~550 nm (e.g., BODIPY 576/589) is covalently attached to a hydrophobic fluorescent polymer with emission wavelength of ~450 nm or less (e.g., PFO).

Example 16

Preparation of 2-Step FRET NPs with Varying Amounts of BODIPY 576/589

NPs were formulated with Polymer 7, Polymer 8, Polymer 10 or Polymer 11 and isolated, as described in Example 1 and Example 12, to monitor the effect of different amounts (mol %) of BODIPY 576/589 on NP fluorescent properties. A series of polymers having the general structure $(PFO)_{0.97n}$-co-$(PBT)_{0.02n}$-co-(PF-BODIPY 576/589)$_{zn}$ were prepared varying the BODIPY 576/589 content from 8 to 1 mol % (z=0.08, 0.03, 0.02 and 0.01). The following formulation was used for each NP sample: 1.5 mg of Polymer 7, 8, 10 or 11 ($M_n$=20,000 g/mol for Polymer 8 and 10, $M_n$=30,300 g/mol for Polymer 11, or $M_n$=40,000 g/mol for Polymer 7), 0.5 mg of PS (1700 g/mol) (Polymer Source), 3.56 mg of PS-b-PEG ($M_n$=3900 g/mol) copolymer and 0.44 mg of PS-b-PEG ($M_n$=9200 g/mol) copolymer (Polymer Source) were dissolved in 1 mL of THF. Particles sizes and optical properties were measured as disclosed herein (see, Table 1 and Table 3).

TABLE 1

Properties of NPs Containing Varying Amounts of BODIPY 576/589

| BODIPY 576/589 (mol %) | Sample/Polymer | HD (nm) | PdI | QY |
|---|---|---|---|---|
| 8 | Sample 16/Polymer 8 | 45 | 0.10 | 0.07 |
| 3 | Sample 17/Polymer 10 | 42 | 0.08 | 0.17 |
| 2 | Sample 18/Polymer 11 | 49 | 0.09 | 0.32 |
| 1 | Sample 15/Polymer 7 | 52 | 0.07 | 0.59 |

Figure 10:
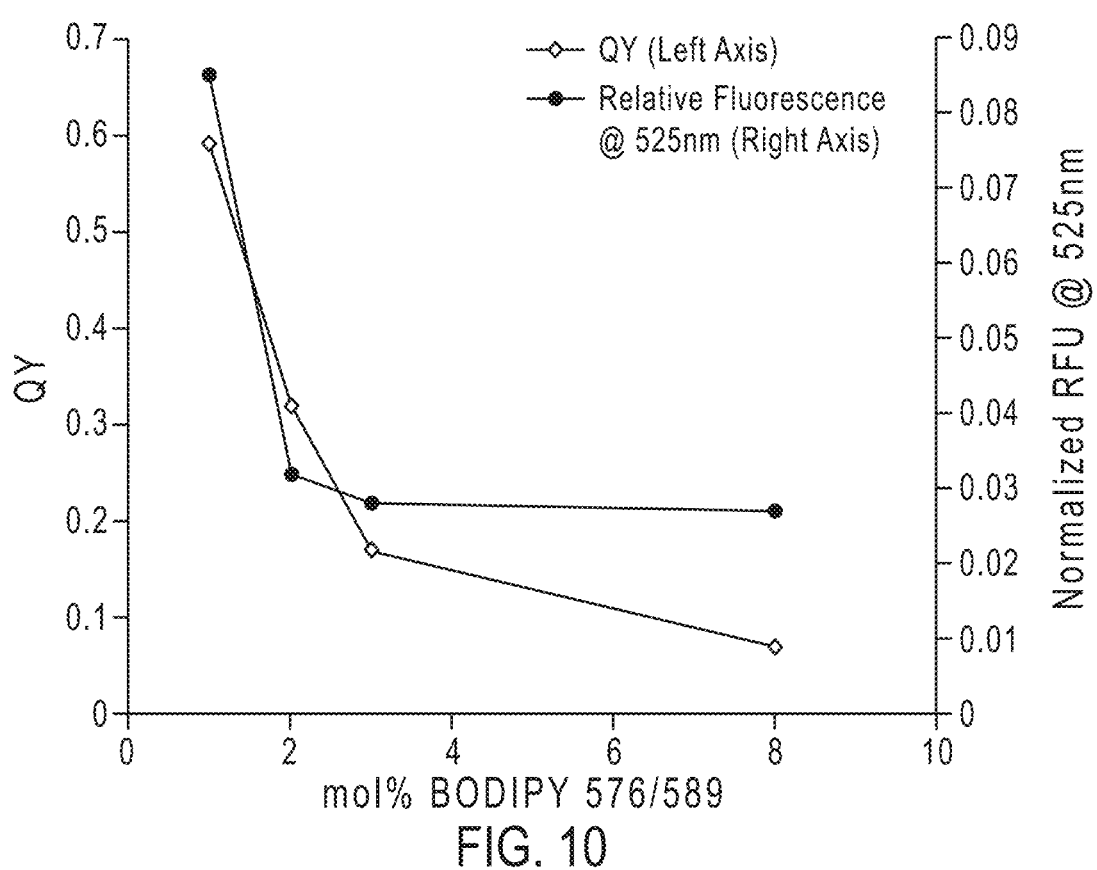
FIG. 10 is a plot showing the emission profile and QY for fluorescent polymers including different amounts of BODIPY 576/589.

Referring to Table 1, the particles were sub-micron sized and had low polydispersity. Energy transfer efficiency from PBT to BODIPY 576/589 was consistently high (≥85%) for each of the samples tested. Interestingly, QY increased dramatically from 0.07 to 0.59, and the normalized fluorescent intensity measured at 525 nm increased from 0.027 to 0.085 (FIG. 10) as the amount of BODIPY 576/589 linked to the polymer backbone was decreased from 8 to 1 mol %. This example demonstrates that optical properties (e.g., QY and emission intensity) can be improved in a controlled manner by decreasing the amount of BODIPY dye in the FRET-capable polymer. While not wishing to be bound by theory, as BODIPY content within the particle increases, so too does the number of fluorophores packaged into the finite space of the hydrophobic internal region of the particle. Confinement of large numbers of fluorophores within the hydrophobic core of the particle can result in self-quenching of fluorescent emission and a decrease in QY. However, the ability to precisely control the size and optical properties of fluorescent particles makes these 2-step FRET particles particularly attractive especially for use in fluorescence-based applications requiring fluorophores with well-defined fluorescence and physical properties.

Example 17

Synthesis of 2-Step FRET Fluorescent Copolymer $(PFO)_{0.92n}$-co-$(PBT2T)_{0.03n}$-co-(PF-BODIPY 630/650)$_{0.05n}$ (Polymer 17)

(III)

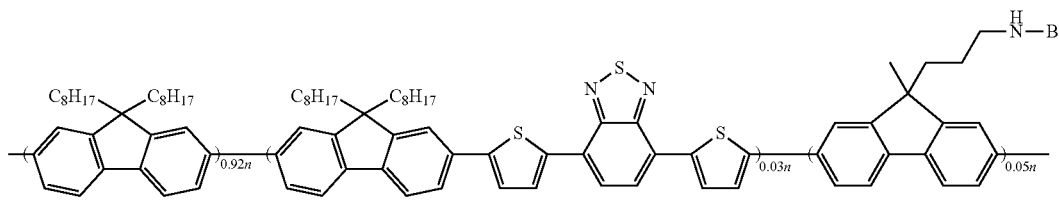

The amine reactive copolymer precursor to Polymer 15 (Compound III) was synthesized as described in Example 10, with the exception that monomer 4,7-dibromobenzo[c][1,2,5]thiadiazole was replaced with 4,7-bis(5-bromothiophen-2-yl)benzo[c][1,2,5]thiadiazole. Deprotection of the t-Boc group was achieved using the same method as described in Example 10. The deprotected polymer then was reacted with BODIPY 630/650 NHS Ester (Thermo Fisher Scientific) as described in Example 11 to yield $(PFO)_{0.92n}$-co-$(PBT2T)_{0.03n}$-co-(PF-BODIPY 630/650)$_{0.05n}$ ($M_n$=20,000 g/mol; Polymer 17).

Example 18

Figure 11:
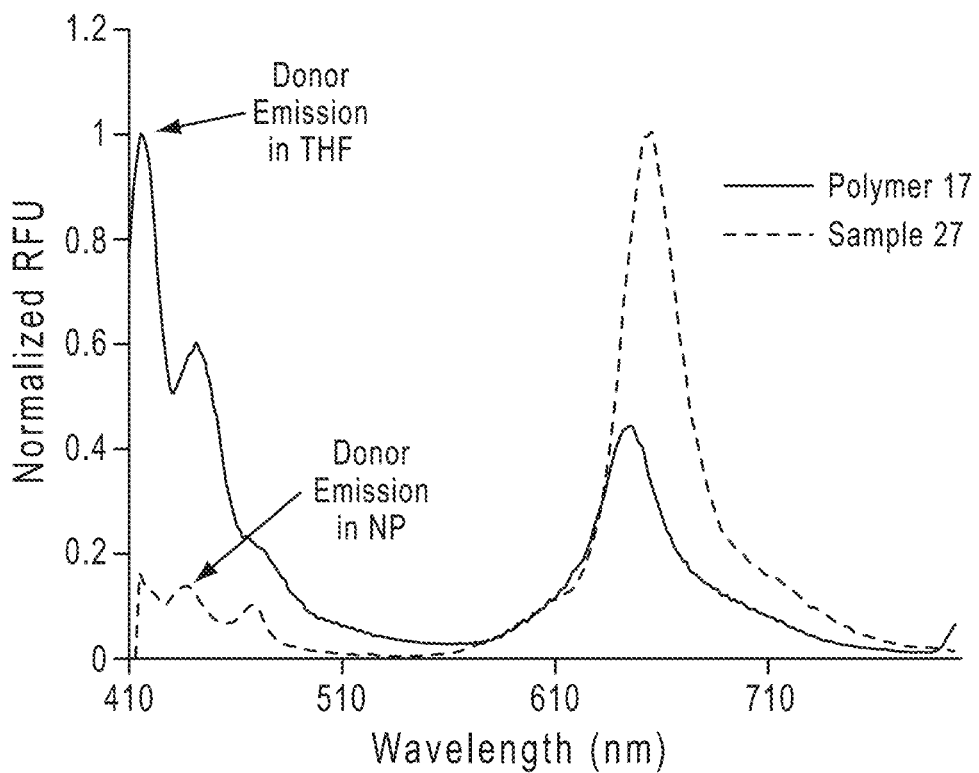
FIG. 11 is a plot showing the emission profile of Polymer 17 when dissolved in THF and when packaged into a NP in DI water (Sample 27).

Energy Transfer Efficiency Enhancement for NPs Formulated with $(PFO)_{0.92n}$-co-$(PBT2T)_{0.03n}$-co-(PF-BODIPY 630/650)$_{0.05n}$ This example demonstrates the difference in energy transfer efficiency for Polymer 17 in THF compared to when packaged in NPs (Sample 27). Polymer 17 involves a 2-step FRET process. Upon excitation of the NPs, energy is transferred from PFO to PBT2T and then from PBT2T to the covalently attached BODIPY 630/650. Excitation of Polymer 17 in THF and at 405 nm resulted in ~30% energy transfer efficiency from PFO and PBT2T to BODIPY 630/650. Efficiency was estimated by comparing the ratio of peak intensity of the BODIPY 630/650 acceptor dye emission at 645 nm over the sum of the peak intensity of the acceptor emission plus PFO donor emission at 415 nm. NPs were formulated as described in Example 14, but NP size was not measured due to unavailability of a suitable laser source. QY for Sample 27 (Polymer 17) was 0.18 (see, Table 3). Energy transfer efficiency to BODIPY 630/650 was 88%, a ~3-fold enhancement in energy transfer to the covalently attached BODIPY 630/650 relative to when measured for Polymer 17 in THF (~30%) (see, Table 4 and FIG. 11). A similar increase in energy transfer efficiency was observed for Polymer 14 in THF and Sample 21 in water (FIG. 8) except that the emission from the PBT2T repeat unit (~520 nm-600 nm) is less intense for both Polymer 17 in THF and NP Sample 27 (FIG. 11) in water than the emission from the PBT repeat unit at 520-600 nm of Polymer 14 and Sample 21. This seems to indicate that energy transfer from PBT2T to BODIPY 630/650 is more complete. Thus, incorporation of PBT2T repeat units into the fluorescent polymer can effectively transfer energy from PFO to higher wavelength emitting BODIPY dyes. The ability of PBT2T to relay energy more efficiently than PBT to acceptor fluorophores with an excitation maximum at 630 nm or greater expands the obtainable fluorescent emission range that can be accessed using the fluorescent particles. This feature of the instant particles has particular benefits in fluorescent assays where multi-color emission is required for simultaneous detection of several properties, while using only one excitation wavelength.

Example 19

Preparation of PFO/BODIPY 569/574/PS-b-PEG NPs in Phosphate Buffer Solution

NPs including a hydrophobic core containing a mixture of a hydrophobic, conjugated polymer and a small molecule, hydrophobic BODIPY fluorescent dye that emits light in the orange region of the spectrum were prepared. 2.0 mg of PFO ($M_n$=28,700 g/mol) (Sigma-Aldrich Corp.), 0.2 mg of BODIPY 569/574 dye, 2.52 mg of PS-b-PEG ($M_n$=3900 g/mol) copolymer and 1.48 mg of PS-b-PEG ($M_n$=9200 g/mol) copolymer (Polymer Source) were dissolved in 1 mL THF. NPs were formulated and isolated as described in Example 1 (Sample 28). HD and PdI for the NPs were 57 nm and 0.05, respectively. Upon excitation with a violet laser at 405 nm, the NPs dissolved in phosphate buffer solution yielded a maximum emission peak at 612 nm and a QY of 0.20, indicating the there was a moderate level of intermolecular energy transfer from the conjugated polymer to the fluorescent dye within the NP core.

Example 20

Preparation of PFO/PEGylated-Phospholipids/PS-b-PEG NPs in Phosphate Buffer Solution Fluorescent NPs were prepared as described in Example 1, with the exception that a phospholipid-based amphiphilic molecule was used to help colloidal dispersion of the hydrophobic fluorescent polymer in water. 2.0 mg of PFO ($M_n$=28,700 g/mol) (Sigma-Aldrich Corp.), 1.52 mg of PEGylated-phosphatidylethanolamines (mPEG-PE; $M_n$=1415 g/mol; Avanti Polar Lipids, Alabaster, Ala.) and 2.48 mg of PS-b-PEG ($M_n$=9200 g/mol) copolymer (Polymer Source) were dissolved in 1 mL of THF. HD and PdI were 67 nm and 0.05, respectively (Sample 29).

Example 21

Synthesis of PS-Dye Conjugates

Polystyrene-dye conjugates were synthesized by reacting amine terminated polystyrene with fluorescent dyes containing N-hydroxysuccinimide (NHS) reactive esters. For example, 25 mg (9.6 μmol) amine terminated polystyrene (NH$_2$—PS; M$_n$=2600 g/mol; Polymer Source) was dissolved in 0.4 mL THF and 4.41 mg (10.5 μmol) BODIPY 493/503, NHS ester (Succinimidyl ester) (Thermo Fisher Scientific) was dissolved in 1.5 mL anhydrous THF. After complete dissolution, 100 μL of NH$_2$—PS and 3.35 μL of 0.717 M triethylamine (TEA) in THF were added to the dye solution every 30 minutes. This reaction was placed on a vortex mixer in the dark at room temperature. The reaction continued overnight, ~18 h. After reaction, the product was precipitated into ~10 mL cold methanol to remove unreacted BODIPY 493/503 from the product. The precipitate was washed 3 times with 10 mL cold methanol until there was no more visible free BODIPY 493/503 dye in solution. The product was dried in vacuo overnight at room temperature yielding ~20 mg (Polymer 18). The amount of conjugated dye was determined by dissolving the PS-dye conjugate in THF and measuring the absorption of the conjugate at 499 nm. The same procedure was used to prepare PS-dye conjugates with either 2600 or 2500 g/mol NH$_2$—PS using the following commercially-available hydrophobic and hydrophilic fluorescent dyes in NHS ester form (Thermo Fisher Scientific): BODIPY FL, NHS ester (Polymer 19), BODIPY TMR-X, NHS ester (Polymer 20), BODIPY TR-X, NHS ester (Polymer 21), ALEXA FLUOR 546, NHS ester (Polymer 22), ALEXA FLUOR 488, NHS ester (Polymer 23), and ALEXA FLUOR 568, NHS ester (Polymer 24).

Example 22

Preparation of Fluorescent NPs Using PS-Dye Conjugates in Phosphate Buffer Solution Fluorescent NPs were formulated using a combination of polystyrene modified with fluorescent dyes, non-fluorescent polystyrene and amphiphilic polymers. 0.6220 mg of BODIPY FL modified polystyrene (Polymer 19), 2.7 mg of polystyrene (PS) (1700 g/mol) (Polymer Source), 5.31 mg of PS-b-PEG (M$_n$=3900 g/mol) copolymer and 1.39 mg of PS-b-PEG (M$_n$=9200 g/mol) copolymer (Polymer Source) were dissolved in 1 mL THF/DMSO mixture (50/50 by volume). Upon complete dissolution, the THF/DMSO solution was rapidly mixed with an equivalent volume of aqueous PBS, at pH 7.4, using a confined impinging jet mixer with two inlets. Upon impingement and homogenous mixing of the streams nanoparticles were formed through controlled precipitation. The combined streams exiting the mixer were immediately introduced to 8 mL of PBS resulting in a final THF:DMSO:PBS water volume ratio of 1:1:18. THF:DMSO was subsequently removed via dialysis against PBS water to form a solvent free NP solution (Sample 30). Using the same procedure, NPs were prepared using the PS-dye conjugate polymers listed in Example 21. Sizing data and optical properties are listed in Table 2 and Table 3.

TABLE 2

Sizing Data for Particles Containing PS-Dye Conjugates

| Sample | Polymer | HD (nm) | PdI |
|---|---|---|---|
| 30 | 19 | 43 | 0.06 |
| 31 | 18 | 42 | 0.04 |
| 32 | 20 | 40 | 0.03 |
| 33 | 21 | HD and PdI could not be measured on available instrumentation | |

TABLE 2-continued

Sizing Data for Particles Containing PS-Dye Conjugates

| Sample | Polymer | HD (nm) | PdI |
|---|---|---|---|
| 34 | 22 | 36 | 0.05 |
| 35 | 23 | 57 | 0.11 |
| 36 | 24 | 53 | 0.13 |

This example shows that hydrophobic or hydrophilic organic dyes can be linked to a hydrophobic, non-fluorescent polymer and successfully packaged into particulate form to provide a fluorescent particle. Hydrophobic dyes such as ALEXA FLUOR 546 were incorporated well into the particle, as (Sample 34) evidenced by the small HD and low PdI. However, formulations including hydrophilic dyes such as ALEXA FLUOR 488 (Polymer 23) and ALEXA FLUOR 568 (Polymer 24) yielded larger particles with higher polydispersity and lower QY, suggesting that these dyes were less well incorporated into the hydrophobic core of the fluorescent particle.

Example 23

Preparation of NPs Formulated with Multiple PS-Dye Conjugates

Figure 12:
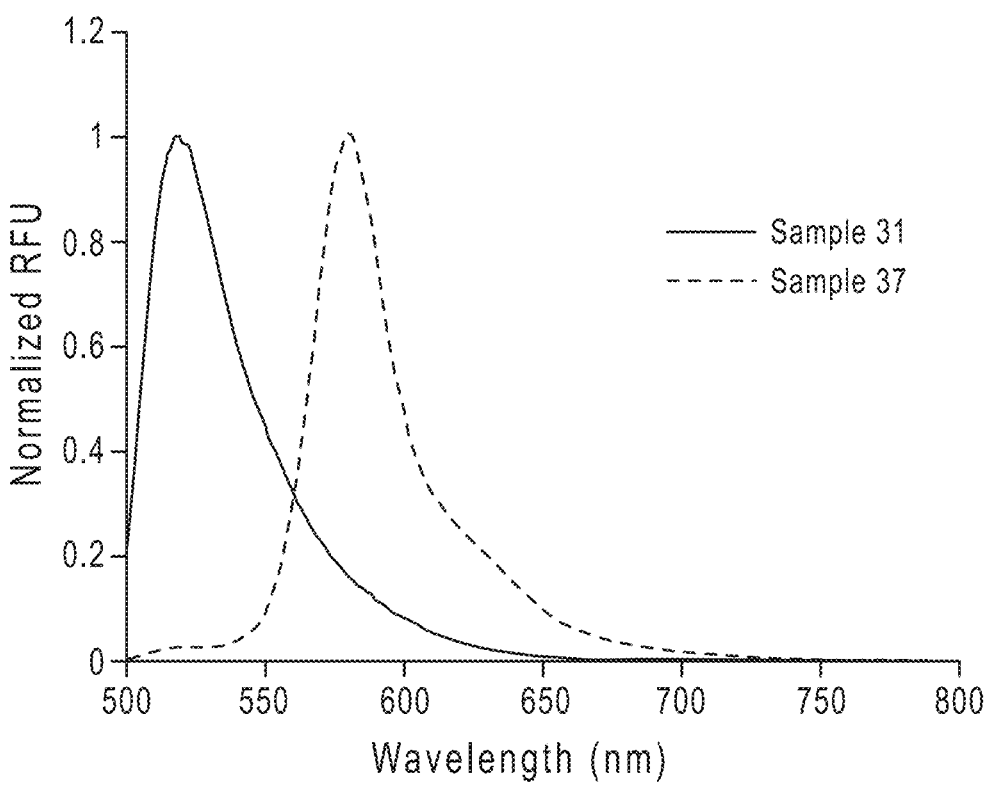
FIG. 12 is a plot comparing the emission profiles for Sample 31 and Sample 37.
Figure 13:
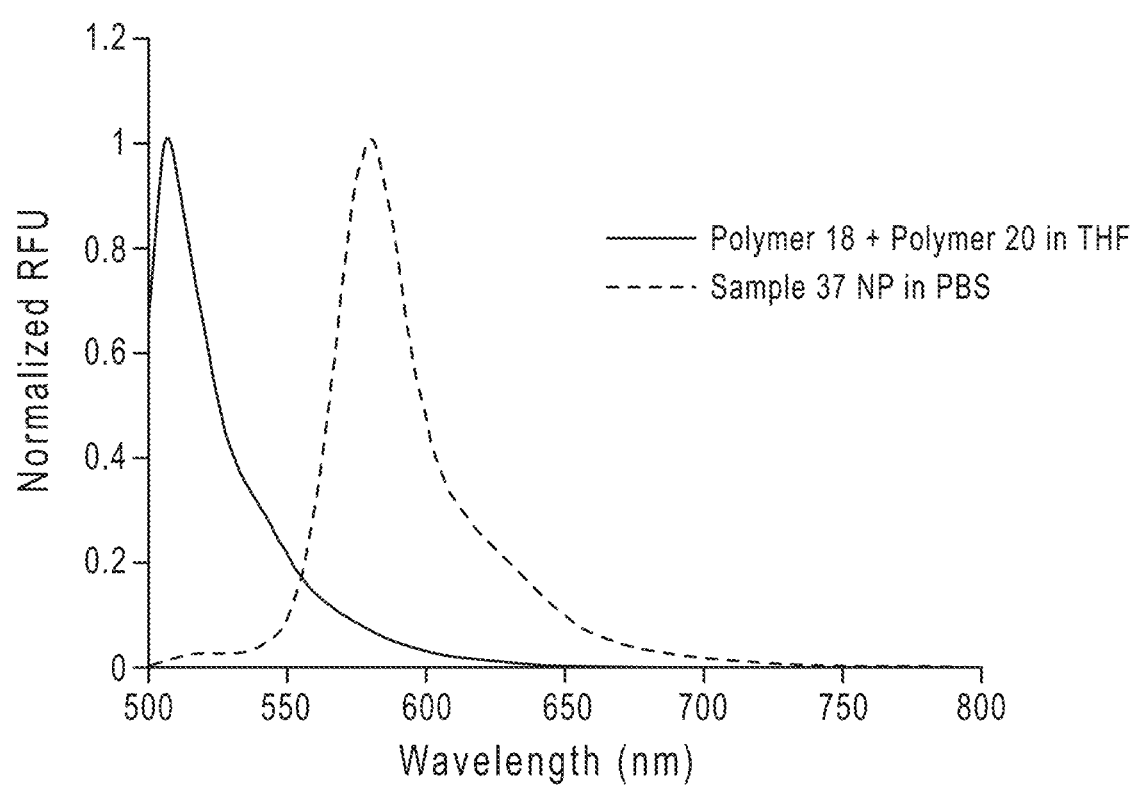
FIG. 13 is a plot comparing emission profiles for Polymer 18 and Polymer 20 in THF and Sample 37 in PBS.

FRET-capable NPs were formulated by loading two different PS-dye conjugates into the particle. The hydrophobic core of the NPs includes a first conjugate that includes a donor dye, a second conjugate that includes an acceptor dye, and non-fluorescent hydrophobic polymer. The synthesis of a particle including Polymer 18 and Polymer 20 using a 12:1 molar ratio is described. 8.16 mg of PS-BODIPY 493/503 (M$_n$=2800 g/mol; Polymer 18), 0.75 mg PS-BODIPY-TMR (M$_n$=3000 g/mol; Polymer 20), 1.0 mg PS (M$_n$=1700 g/mol; Polymer Source), 15.9 mg of PS-b-PEG (M$_n$=3900 g/mol) copolymer and 4.17 mg of PS-b-PEG (M$_n$=9200 g/mol) copolymer (Polymer Source) were dissolved in 3 mL THF/DMSO mixture (50/50 by volume). The particles were formulated and isolated, as described in Example 22, with the exception that the combined streams exiting the mixer were introduced to 27 mL of PBS to produce a final THF:DMSO:PBS water volume ratio of 1:1:18 (Sample 37). HD and PdI were 47 nm and 0.06, respectively. FIG. 12 compares the emission profiles for Sample 37 and NPs loaded with only PS-BODIPY493/503 (Sample 31). For comparison, FIG. 13 compares the emission spectra for Sample 37 in PBS and for a mixture of Polymer 18 and Polymer 20 in THF to illustrate that enhanced FRET efficiency occurs when these polymers are contained in NP form under aqueous conditions, but not when both the donor and acceptor fluorophores are dissolved in THF. The emission spectrum for Sample 31 has an emission peak at 518 nm resulting from fluorescence of BODIPY 493/503, whereas emission at 518 nm was substantially reduced (~97% less) for Sample 37 (see, FIG. 12). The reduction in emission at 518 nm indicates highly efficient energy transfer from BODIPY 493/503-PS to BODIPY TMR-PS when these PS-dye conjugates are packaged into NPs. Because the energy transfer is so complete when this tandem dye system is incorporated into the hydrophobic core of a water-soluble NP, it becomes possible to use lower quantities of acceptor dye in the fluorescent NP than would be required if the tandem system were being utilized in solution. As a result, the likelihood of fluorescent interference in assays using multiple excitation sources can be minimized.

Example 24

Synthesis of Polystyrene-Block-PEG-Dye Conjugates

This example describes the synthesis of a fluorescent, amphiphilic polymer. Polystyrene-block-PEG-dye (PS-b-PEG-dye) conjugates were synthesized by reacting amine terminated PS-b-PEG with fluorescent dyes containing N-hydroxysuccinimide (NHS) reactive esters. First, the hydroxyl end group of PS-b-PEG ($M_n$=3900 g/mol; Polymer Source) was converted to a mesylate and then to a primary amine 800 mg (0.205 mmol) PS-PEG was added to a 50 mL one-neck round-bottom flask installed with a distilling receiver and a condenser. 30 mL of anhydrous toluene was added. The flask was heated in an oil bath (~130° C.) to distill ~20 mL toluene. Then, 20 mL of anhydrous toluene was added and 10 mL was distilled off again to give ~10 mM polymer solution. The solution was then cooled to room temperature. 65 µL (0.615 mmol) TEA was added to the solution under $N_2$, and the mixture was stirred at room temperature for 15 minutes. Then 80 µL (1.03 mmol) methanesulfonyl Cl (Sigma-Aldrich Corp.) was dripped slowly into the mixture. The reaction continued at room temperature for 24 h. The TEA chloride salts were filtered from the reaction using a 0.2 inn PTFE filter. The solution was concentrated via rotary evaporation to approximately 3 mL. The product was precipitated into ice cold diethyl ether and allowed to sit for 20 minutes and then vortexed. The precipitate was washed twice with cold diethyl ether, and the product was collected through centrifugation at 4500 rcf. The product was dried under house vacuum overnight to yield 630 mg and analyzed by 41 NMR. NMR (400 MHz, $CDCl_3$) δ 7.2-6.2 (br, 72H, $C_6H_5$), 4.38 (t, 2H, $CH_2$), 3.65 (br, ~160H, $CH_2$), 3.08 (s, 3H, $CH_3$).

In a next step, 550 mg (0.140 mmol) PS-PEG-mesylate was added to a 50 mL round-bottomed flask equipped with a stir bar. 15-16 mL (225 mmol) of ammonium hydroxide was added (28% $NH_3$). After addition the flask was sealed with a rubber septum and clamped shut with copper wire. The flask was vigorously stirred at room temperature for 96 h. After the fourth day, the rubber septum was removed and the ammonia was allowed to evaporate for 48 h. The pH was adjusted to 13 with 1.0 N NaOH and the $NH_2$—PEG-b-PS product was extracted with DCM. Brine was added during extraction to help force the product into DCM. 20 mL DCM washings were repeated in triplicate. The DCM washes were combined and dried over potassium carbonate. The potassium carbonate was filtered off using a 0.2 µm PTFE syringe filter and the DCM solution was concentrated via rotary evaporation to ~2 mL. The product was precipitated into ice cold diethyl ether and the precipitate was washed three times with ice cold diethyl ether. The product was collected by centrifugation and dried overnight under house vacuum to yield 410 mg amine modified PS-b-PEG (PS-b-PEG-$NH_2$). NMR (400 MHz, $CDCl_3$) δ 7.2-6.2 (br, 72H, $C_6H_5$), 3.65 (br, ~170H, $CH_2$), 2.9 (m, 2H, $CH_2$—$NH_2$). The conversion of mesylate to amine was apparent by the disappearance of the proton shifts due to the presence of mesylate. Conversion to amine was also detected using a colorimetric amine assay and TLC with subsequent staining with ninhydrin.

In the final step, PS-b-PEG-$NH_2$ was reacted to dyes containing NHS reactive esters. For example, 15 mg (3.3 µmol) PS-b-PEG-$NH_2$ ($M_n$=3900 g/mol) was dissolved in 0.2 mL of anhydrous DMSO and 4.95 mg (3.9 µmol) ALEXA FLUOR 546, NHS ester (Thermo Fisher Scientific) was dissolved in 0.45 mL anhydrous DMSO. After complete dissolution, the PS-b-PEG-$NH_2$ solution and 9.12 µL of 0.717 M triethylamine (TEA) in DMSO were added to the dye solution. This reaction was placed on a vortex mixer, in the dark at room temperature and allowed to react overnight, ~18 h. After reaction, unreacted dye was removed by dialysis using 3.5 kDa molecular weight cut-off tubing (Spectrum Laboratories, Inc., Rancho Dominguez, Calif.). Dialysis was first performed against DMSO for 4 h and then DI water with 4 media changes over 24 h. The product was frozen on dry ice and water was removed via lyophilization to yield ~15 mg of a bright red solid (Polymer 25). The amount of conjugated ALEXA FLUOR 546 was determined by dissolving PS-b-PEG-dye conjugate in THF and then diluting 10 fold into aqueous PBS and measuring the absorption of the conjugate at 556 nm. PS-b-PEG-dye conjugates were also synthesized following the same procedure with (ALEXA FLUOR 488, NHS ester (Polymer 26) and ALEXA FLUOR 647, NHS ester (Polymer 27), both available from Thermo Fisher Scientific.

Example 25

Preparation of Fluorescent NPs Using Polystyrene-Block-PEG-Dye Conjugates in Phosphate Buffer Solution This example demonstrates formulation of fluorescent NPs using PS-b-PEG-dye conjugates (e.g., fluorescently tagged PS-b-PEG copolymers as described in Example 24) and a hydrophobic, non-fluorescent polymer. 0.89 mg of ALEXA FLUOR 546 modified PS-b-PEG (Polymer 25), 3.3 mg of PS ($M_n$=1700 g/mol; Polymer Source), 4.39 mg of PS-b-PEG ($M_n$=3900 g/mol) copolymer and 1.39 mg of PS-b-PEG ($M_n$=9200 g/mol) copolymer (Polymer Source) were dissolved in THF/DMSO mixture that was 50/50 by volume. NPs were then formulated and isolated as described in Example 22 (Sample 38). HD and PdI were 47 nm and 0.06, respectively. This same procedure was used to prepare NP samples with Polymer 26 and Polymer 27 to give Sample 39 (HD=48 nm and PdI=0.08) and Sample 40 (HD=43 nm and PdI=0.05), respectively. The sizing data indicates that the disclosed process can be used to successfully prepare bright, sub-micron sized particles with fluorescent, amphiphilic polymers and that these polymers do not adversely affect the PdI of the prepared particles. The relatively high QY for each of the prepared samples indicated that the fluorescence of the dye conjugated to the amphiphilic polymer was not significantly quenched when contained in the shell of the NPs (see, Table 3).

Example 26

Preparation of FRET NPs with Polymer 1 and Non-Fluorescent Hydrophobic Polymers This example demonstrates that fluorescent NPs can be formulated with various types of non-fluorescent hydrophobic polymers to produce NPs with QY of 50% or greater. Miscibility in the NP core between hydrophobic fluorescent copolymer and hydrophobic non-fluorescent polymer is dictated by the difference in the solubility parameter and molecular weight of the material. NPs with Polymer 1 ($M_n$=27,400 g/mol) and three different non-fluorescent hydrophobic polymers were formulated with a 1:1 Polymer 1:non-fluorescent hydrophobic polymer weight ratio. The three non-fluorescent hydrophobic polymers tested were polymethyl methacrylate ($M_n$=1600 g/mol; Polymer Source), poly($\alpha$-methyl styrene) ($M_n$=1300 g/mol; Polymer Source) and poly(4-methyl styrene) ($M_n$=1500 g/mol; Polymer Source). For each sample, 1.0 mg of Polymer 1, 1.0 mg of non-fluorescent hydrophobic polymer, 3.17 mg of PS-b-PEG ($M_n$=3900 g/mol) copolymer and 0.83 mg of PS-b-PEG ($M_n$=9200 g/mol) copolymer (Polymer Source) were dissolved in 1 mL of THF. Each NP sample was formulated as described in Example 1. After formulation, the HD and PdI were measured via DLS. Each sample exhibited similar HD and PdI to samples that used PS. Sample 41 contained polymethyl methacrylate (HD=39 nm, PdI=0.1), Sample 42 contained poly($\alpha$-methyl styrene) (HD=42 nm, PdI=0.11) and Sample 43 contained poly(4-methyl styrene) (HD=43 nm, PdI=0.07). Table 3 lists optical properties of these samples.

Example 27

Measurement of Optical Properties

The spectral properties for fluorescent particles prepared as described herein are listed in Table 3. ND denotes parameter was not determined.

TABLE 3

| Optical Properties for Fluorescent NPs | | | | |
|---|---|---|---|---|
| Sample | Polymer | Ex $\lambda_{max}$ (nm) | Em $\lambda_{max}$ (nm) | QY |
| 1 | Supplier | 383 | 438 | 0.43 |
| 2 | Supplier | 383 | 438 | 0.43 |
| 3 | Supplier | 383 | 438 | 0.52 |
| 4 | Supplier | 383 | 508 | 0.47 |
| 5 | 2 | 380 | 517 | 0.34 |
| 6 | 1 | 380 | 517 | 0.58 |
| 7 | 3 | 389 | 520 | 0.39 |
| 8 | 4 | 387 | 521 | ND |
| 9 | 5 | 388 | 603 | 0.35 |
| 10 | 6 | 384 | 607 | ND |
| 11 | 1 | 380 | 517 | 0.68 |
| 12 | 1 | 380 | 517 | 0.57 |
| 13 | 1 | 380 | 517 | 0.54 |
| 14 | 9 | 383 | 604 | 0.31 |
| 15 | 7 | 377 | 604 | 0.59 |
| 16 | 8 | 360 | 609 | 0.07 |
| 17 | 10 | 367 | 605 | 0.17 |
| 18 | 11 | 378 | 602 | 0.32 |
| 19 | 12 | 383 | 563 | 0.31 |
| 20 | 13 | 384 | 557 | 0.21 |
| 21 | 14 | 383 | 656 | 0.28 |
| 22 | 15 | 383 | 676 | ND |
| 23 | 16 | 384 | 603 | 0.66 |
| 24 | 16 | 381 | 602 | 0.60 |
| 25 | 16 | 377 | 604 | 0.53 |
| 26 | 16 | 377 | 604 | 0.59 |
| 27 | 17 | 387 | 655 | 0.18 |
| 28 | Supplier | 382 | 612 | 0.20 |
| 29 | Supplier | 383 | 438 | 0.48 |
| 30 | 19 | 512 | 524 | 0.55 |
| 31 | 18 | 503 | 518 | 0.64 |
| 32 | 20 | 551 | 579 | ND |
| 33 | 21 | 606 | 632 | 0.37 |
| 34 | 22 | 558 | 576 | 0.57 |
| 35 | 23 | 499 | 523 | 0.11 |
| 36 | 24 | 578 | 603 | 0.04 |
| 37 | 18 & 20 | 505 | 581 | 0.73 |
| 38 | 25 | 559 | 573 | 0.53 |
| 39 | 26 | 495 | 519 | 0.78 |
| 40 | 27 | 653 | 669 | 0.28 |
| 41 | 1 | 380 | 517 | 0.56 |

TABLE 3-continued

| Optical Properties for Fluorescent NPs | | | | |
|---|---|---|---|---|
| Sample | Polymer | Ex $\lambda_{max}$ (nm) | Em $\lambda_{max}$ (nm) | QY |
| 42 | 1 | 380 | 517 | 0.60 |
| 43 | 1 | 380 | 517 | 0.61 |

Example 28

Measurement of FRET Efficiency

Energy transfer efficiencies were evaluated for fluorescent polymers and particles listed in Table 4. Percent relative energy transfer was estimated using Equation 1 to compare the ratio of the relative intensity of the acceptor fluorophore to the sum of the relative intensity (RFU) of the acceptor fluorophore and donor fluorophore.

TABLE 4

| FRET Efficiencies | | |
|---|---|---|
| Example | Material (Polymer/Sample) | Relative Energy Transfer Efficiency Polymer in THF/Sample in DI $H_2O$ |
| 9 | Polymer 1/Sample 13 | 50%/98% |
| 9 | Polymer 2/Sample 5 | 57%/97% |
| 9 | Polymer 3/Sample 7 | 60%/91% |
| 9 | Polymer 4/Sample 8 | 69%/97% |
| 9 | Polymer 5/Sample 9 | 61%/72% |
| 9 | Polymer 6/Sample 10 | 55%/72% |
| 14 | Polymer 12/Sample 19 | 43%/96% |
| 14 | Polymer 13/Sample 20 | 40%/94% |
| 14 | Polymer 14/Sample 21 | 22%/90% |
| 14 | Polymer 16/Sample 26 | 24%/98% |
| 15 | Polymer 9/Sample 14 | 34%/96% |
| 18 | Polymer 17/Sample 27 | 30%/88% |

Example 29

Synthesis of PS-b-PEG Terminated with Reactive Groups

This example describes preparation of PS-b-PEG copolymers terminated with various reactive groups, represented as PS-b-PEG-R, where R can be a carboxylic acid, primary amine, azide, alkyne or cycloalkyne. PS-b-PEG terminated at the PEG end with hydroxyl functionality is commercially available (Polymer Source). Conversions of a hydroxyl group to a carboxylic acid, primary amine, azide, alkyne or cycloalkyne are well-known to those skilled in the art.

Amine terminated PEG-b-PS can be synthesized and purified as described in Example 24 using PS-b-PEG with molecular weight $M_n$=9200 g/mol (PEG $M_n$=7500 g/mol and PS $M_n$=1700 g/mol; Polymer Source). The amine terminated PS-b-PEG can be reacted with a heterobifunctional cross-linker carrying an activated ester group to yield reactive PS-b-PEG copolymers. For example, 50 mg (5.4 μmol) of amine terminated PS-b-PEG ($M_n$=9200 g/mol) was dissolved in 400 μL of anhydrous DMSO and 4.75 mg (16.3 μmol) of (1R,8S,9s)-bicyclo[6.1.0] non-4-yn-9-ylmethyl succinimidyl carbonate (BCN-NHS) (Berry & Associates Inc., Dexter, Mich.) was dissolved in 690 μL of anhydrous DMSO. 200 μL of amine terminated PS-b-PEG solution and 7.6 µL of 0.717 M TEA in DMSO was added to the BCN-NHS DMSO solution in two aliquots in 30 min intervals. This solution was allowed to react overnight in the dark at room temperature on a vortex shaker. The product was purified by dialysis first against DMSO and then against DI water and isolated by lyophilization, as described in Example 24 for the PS-b-PEG dye conjugates. 4l NMR in CDCl₃ confirm the presence of BCN in the product, apparent from the presence of methylene protons adjacent to the carbamate bond (—NH—C(O)—O—CH₂—CH—) at 4.2 ppm, and the methylene protons adjacent to the alkyne moiety in the cyclooctyne ring at ~2.2 ppm.

To synthesize azide terminated PS-b-PEG, mesylate terminated PS-b-PEG ($M_n$=9200 g/mol) was synthesized as described in Example 24. Then mesylate terminated PS-b-PEG (500 mg; 54 µmol) and NaN₃ (21.2 mg; 326 µmol) were added to a 25 mL round-bottomed flask equipped with a stir bar. 6 mL of anhydrous dimethylformamide (DMF) ([PS-PEG-mesylate] ≅9-10 mM) was added under N₂. The flask was heated and stirred in an oil bath at 70° C. overnight. Following reaction, DMF was removed via vacuum distillation at 70° C. on a rotary evaporator (pressure ≅30 mbar). 6 mL of toluene was added and the salts were filtered off using a 0.2 µM PTFE syringe filter. The resulting azide terminated PS-b-PEG was isolated (460 mg), as described in Example 24. ¹H NMR was run in CDCl₃ on the product to confirm the disappearance of the mesylate group at 3.08 ppm and presence of the azide functionality by the adjacent methylene protons at 3.4 ppm.

To synthesize alkyne terminated PS-b-PEG, 300 mg (33 µmol) of PS-PEG ($M_n$=9200; Polymer Source) was placed in a 50 mL one-neck round bottomed flask and 2 ml of dry DCM was added. Anhydrous toluene (10 ml) was added and the solvent was evaporated on a rotary evaporator at 30° C. To the residue another 10 mL of dry toluene was added and the solvent was evaporated to dryness. The residue was further dried under high vacuum for 1 hour to remove any remaining residual water. To the flask 15 mg of 60 wt % NaH was added and the flask was capped with a septum and a needle inlet to purge with argon. Anhydrous THF (5 mL) was added under argon and the mixture was stirred at room temperature for 1 h. Propargyl bromide was added via syringe under argon, and the mixture was stirred for 18 h. The septum was removed, water (several drops) was added to quench the reaction, and then solvent was removed by rotary evaporation, and the residue was dissolved in 20 mL of chloroform. The solution was filtered and the solvent was evaporated. The residue was purified by column chromatography on a 25 g SNAP column (Biotage, Charlotte, N.C.). The desired fractions were combined and evaporated to dryness. After complete solvent removal 260 mg of a waxy solid was obtained.

Example 30

Preparation of Surface Reactive Fluorescent NPs

A method for formulating fluorescent NPs with surface reactive groups is described. To produce NPs with reactive functional groups, PS-b-PEG copolymer terminated with a given reactive R group, as described in Example 29, is incorporated into the NP formulation, as described herein. Through the incorporation of a reactive PS-b-PEG-R in the formulation, NP surfaces present reactive groups (R) in a single step. This method is particularly convenient as the NP surface does not need to be modified after formulation to introduce reactive functionality for conjugation to subsequent molecules. Reactive NPs were formulated using this procedure, where R was carboxylic acid, primary amine, azide, alkyne or cycloalkyne.

Example 31

Figure 14:
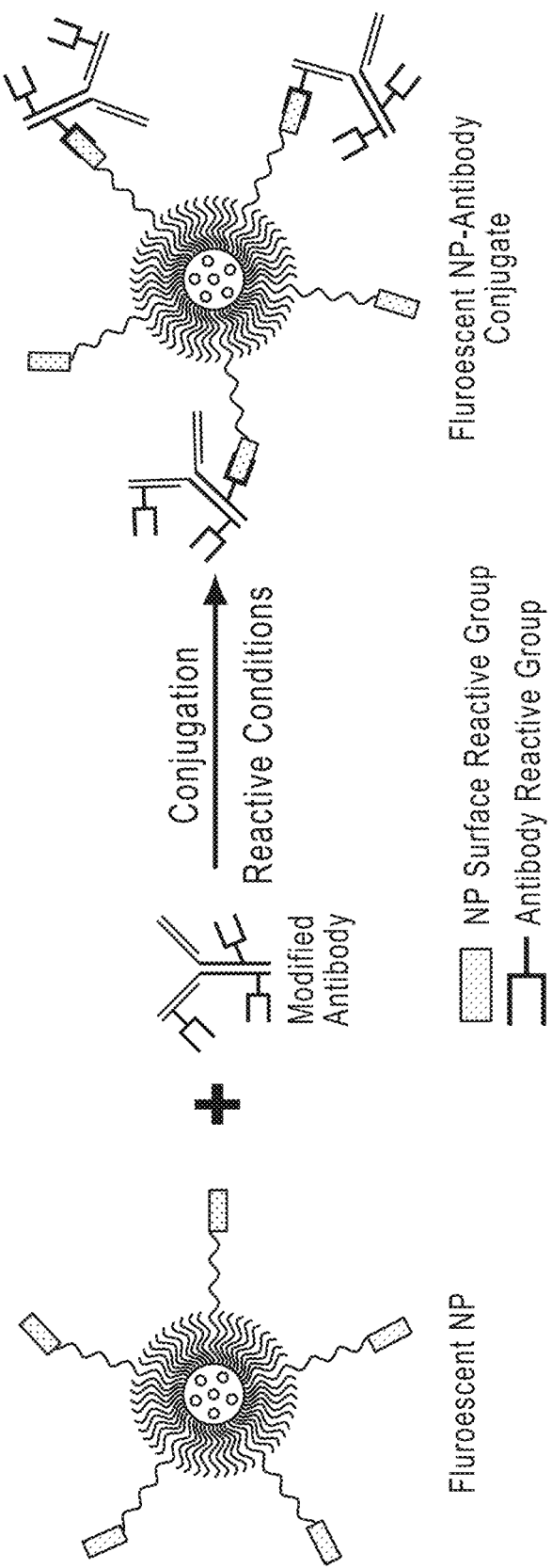
FIG. 14 is a diagram illustrating a general scheme for conjugation of antibodies to the surface of fluorescent NPs.

Preparation of Fluorescent NP-Antibody Conjugates Using Carbodiimide Chemistry A general scheme for conjugation of antibodies to the surface of fluorescent NPs is shown in FIG. 14. This example describes conjugation of a mouse monoclonal antibody against human CD4 (Thermo Fisher Scientific) to amine functionalized fluorescent NPs, prepared according to the methods described herein Amine functionalized fluorescent NPs ([amine]=2 µM) and 1 µM of antibody were mixed together at a final volume of 960 µL of PBS. A fresh solution of 1-ethyl-3-(3-dimethylaminopropyl)carbodiimide (EDAC) in PBS was prepared at 5 mg/mL, and 40 µL (0.64 µmol) was added to the fluorescent NP and antibody solution. This solution was allowed to react at room temperature for 4 h. Unreacted antibody was removed by 300 kDa molecular weight cut-off (MWCO) centrifugal spin filters in PBS. Conjugation of antibody to fluorescent NP was confirmed by sodium dodecyl sulfate polyacrylamide gel electrophoresis (SDS-PAGE). Carbodiimide chemistry can also be used to conjugate antibodies to carboxylic acid functionalized fluorescent NPs in place of amine functional fluorescent NPs.

Example 32

Preparation of Fluorescent NP-Antibody or Antibody Fragments F(ab) Conjugates Using Copper Catalyzed Click Chemistry A method for conjugation of antibodies to alkyne functional fluorescent NPs is described. A mouse monoclonal antibody against human CD4 was modified with a water-soluble amine-reactive ester of an alkyl azide (azido (PEO)₄ propionic acid, succinimidyl ester) (Thermo Fisher Scientific). The protein was brought to 1.25 mg/mL in sodium azide free PBS, pH 7.4. Sodium bicarbonate (1.0 M), pH 9.0, was added to a final concentration of 100 mM. Lysines on the antibody were modified by adding 20 molar equivalents of azido (PEO)₄ propionic acid, succinimidyl ester in DMSO, for every equivalent of protein. After incubation for 1 h at 25° C., the conjugate material was purified with 2-mL disposable spin columns using P-30 Gel (medium) in PBS. The azide-modified eluate also could be concentrated with centrifugal filters with a 10K MW cut-off, washing 4× with PBS, pH 7.4. Azide-modified protein (0.5 mg/mL in sodium azide free PBS), THPTA/Cu$^{2+}$ (0.25 mM final concentration), sodium ascorbate (1.25 mM final concentration), and alkyne-terminated fluorescent NPs (described in Example 30) at 100 µM alkyne final concentration. The reaction was incubated for 20 hours at 25° C. Conjugation of antibody to fluorescent NP was confirmed by SDS-PAGE. The described method was also implemented with antibody fragments (F(ab)) using an affinity purified F(ab) fragment of a goat anti-mouse IgG₁. The methods described herein also can be used for the conjugation of alkyne modified antibodies or F(ab)s with azide functionalized fluorescent NPs.

Example 33

Preparation of Fluorescent NP-Antibody Conjugates Using Copperless Click Chemistry A method for conjugation of antibodies bearing strained alkyne groups to azide functional fluorescent NPs is described. A mouse monoclonal antibody against human CD4 was modified with a water-soluble amine-reactive ester of an alkyl dibenzoazacyclocotyne (DBCO-PEG$_4$-NHS; Click Chemistry Tools, Scottsdale, Ariz.). The protein was brought to 1.25 mg/mL in sodium azide free PBS, pH 7.4. Sodium bicarbonate (1.0 M), pH 9.0, was added to a final concentration of 100 mM$_n$. Lysine residues on the antibody were modified by adding 20 molar equivalents of DBCO-PEG$_4$-NHS in DMSO, for every equivalent of protein. After incubation for 2 h at 25° C., the conjugate material was purified with 2-mL disposable spin columns using P-30 Gel (medium) in PBS. If necessary, the cyclooctyne-modified eluate was concentrated with centrifugal filters with a 10K MW cut-off, washing 4× with PBS, pH 7.4. The product with a degree of substitution of ~3-5 DBCO moieties per antibody was used at 0.5 mg/mL in PBS for modification with azide functionalized fluorescent NPs, such as described in Example 30, at 100 μM final azide concentration for 72 hours at 25° C. Conjugation of antibody to fluorescent NP was confirmed by SDS-PAGE. The same method was applied to antibody fragments (F(ab)) using an affinity purified F(ab) fragment of a goat anti-mouse IgG$_1$. Similar methods described herein can also be used if the reactive groups are switched and fluorescent NPs with surface reactive strained alkynes are used in conjunction with azide modified antibodies or F(ab)s. As an alternative to using DBCO-PEG$_4$-NHS cross-linker to modify an antibody, water soluble dibenzocyclooctyne (DIBO) derivatives or BCN-NHS (Berry & Associates Inc.) can be used under similar conditions described herein.

Example 34

Preparation of Fluorescent NP-Antibody Conjugates Using Maleimide-Thiol Chemistry A method for conjugation of antibodies using amine functional fluorescent NPs and subsequent maleimide-thiol chemistry is described. 120 μg of mouse monoclonal antibody against human CD4 was modified in PBS buffer with 1 μL of a 2 mg/mL 2-iminothiolane (2-IT) in DI H2O. The antibody was allowed to react with 2-IT for 30 min at room temperature and excess 2-IT was removed through P-30 Gel (medium) in PBS. Simultaneously, amine functionalized fluorescent NPs were modified with succinimidyl 4[N-maleimidomethyl]cyclohexane-1-carboxylate (SMCC) cross-linker (Thermo Fisher Scientific). 100 μL of amine functional fluorescent NPs ([amine]=270 μM) add 3 μL 10 mM SMCC in DMSO, reacted at room temperature for 1 h. Excess SMCC was removed by P-30 gel (medium) in PBS. The purified SMCC modified fluorescent NPs were then mixed with the purified 2-IT modified CD4 antibody and reacted for 2 h at room temperature. Excess antibody was removed using an Äkta Pure 25 fast protein liquid chromatography (FPLC; GE Healthcare Life Sciences, Piscataway, N.J.). Conjugation of antibody to fluorescent NPs was confirmed by SDS-PAGE. As an alternative to using 2-IT chemistry, introduction of thiols to the antibody can be achieved by first reducing the mouse monoclonal antibody against human CD4 in the presence of dithiothreitol (DTT) and then reacting with SMCC modified fluorescent NPs.

Example 35

Figures 15A, 15B:
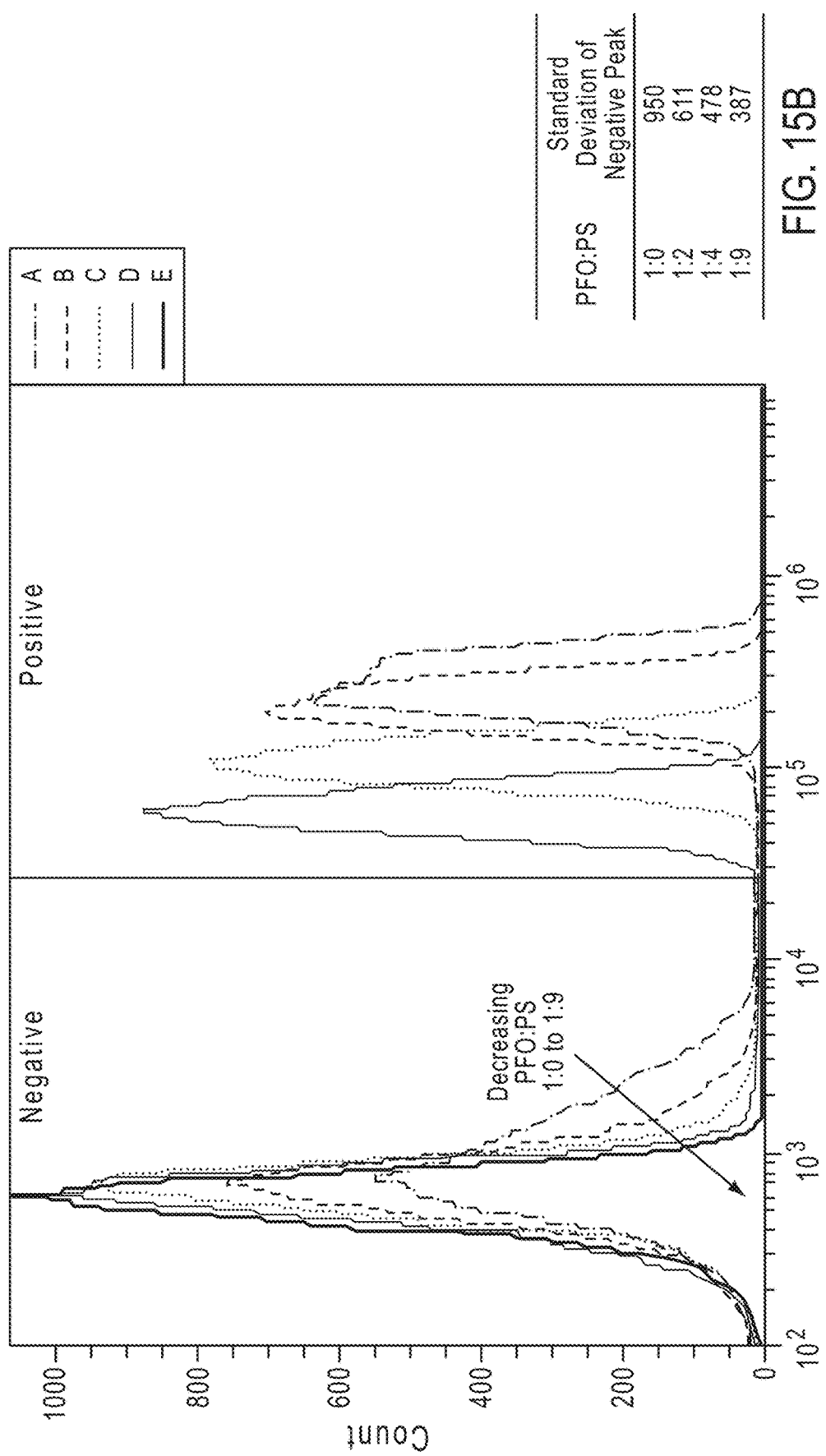
FIG. 15A is a plot of flow cytometric data comparing the effect of PS content in a NP on background signal for NPs having a PFO:PS ratio of 1:0 (A), 1:2 (B), 1:4 (C), 1:9 (D) and unstained cells with no added particle-antibody conjugates (E) (control).
FIG. 15B is a legend for the plot shown in FIG. 15A and lists the standard deviation of the negative peak for samples A-D.

Effect of Hydrophobic Polymer Core Ratio on Non-Specific Background Cell Fluorescence This example shows that a decrease in the ratio of PFO:PS in the core results in a significant reduction in the non-specific cellular fluorescent background as measured by flow cytometry. Azide functional fluorescent particles, prepared according to the methods described in Example 29, including PFO:PS ratios of 1:0 to 1:9 were conjugated to DIBO modified mouse monoclonal antibody against human CD4. White blood cells were prepared from lysed whole blood. Antibody conjugates were diluted in 1% BSA in PBS, pH 7.4, and 10 μL of the conjugates were added to 90 μL of 1×10$^6$ cells. No additional blocking agents were included in the solution. Conjugates and cells were incubated for 20 minutes at room temperature. The cells were then washed 2 times in 1% BSA in PBS, pH 7.4. After the final wash, the cells were resuspended in 500 μL of 1% BSA in PBS, pH 7.4 with no added blocking agent. Stained cells were analyzed using the ATTUNE N×T Acoustic Cytometer (Thermo Fisher Scientific). For CD4 specific staining, 10,000 lymphocyte events were collected, and an excitation laser source of 405 nm was used with a bandpass filter of 415 to 465 nm. Collected data was represented as histograms Cells treated without conjugates were used as a control and are shown in the left-most histogram peak in FIG. 15A. Reduction of the non-specific cellular fluorescence with increased loads of PS in the fluorescent NP can be seen by inspection of the histograms shown in FIG. 15A. The reference unstained cell population (E) overlaps with the histogram for the fluorescent NPs with a PFO:PS ratio of 1:9 (D), indicating that NP's having the highest loadings of PS fluoresce at a level that is essentially equivalent to what is observed for the control. Although NPs with less PS (e.g., PFO:PS of 1:2 and 1:4) yielded background signal at a level just slightly exceeding that of the control, the data clearly shows that the addition of PS into the NP significantly diminished background signal, as detected in the negative histograms of FIG. 15A. In addition, the standard deviation of the negative cell population histograms (left panel) clearly decreases as the amount of PS in the core increases (see, FIG. 15B). This decrease in standard deviation provides yet another indication that addition of PS into the NPs reduces the amount of non-specific binding of the conjugates to the cells. Further, the surprising reduction in background fluorescence for fluorescent NPs loaded with PS was achieved in the absence of additional blocking agents that are commonly used in cell-based assay to combat non-specific binding.

Example 36

Analysis of Antibody-Polymer Conjugate by SDS-PAGE

Figure 16:
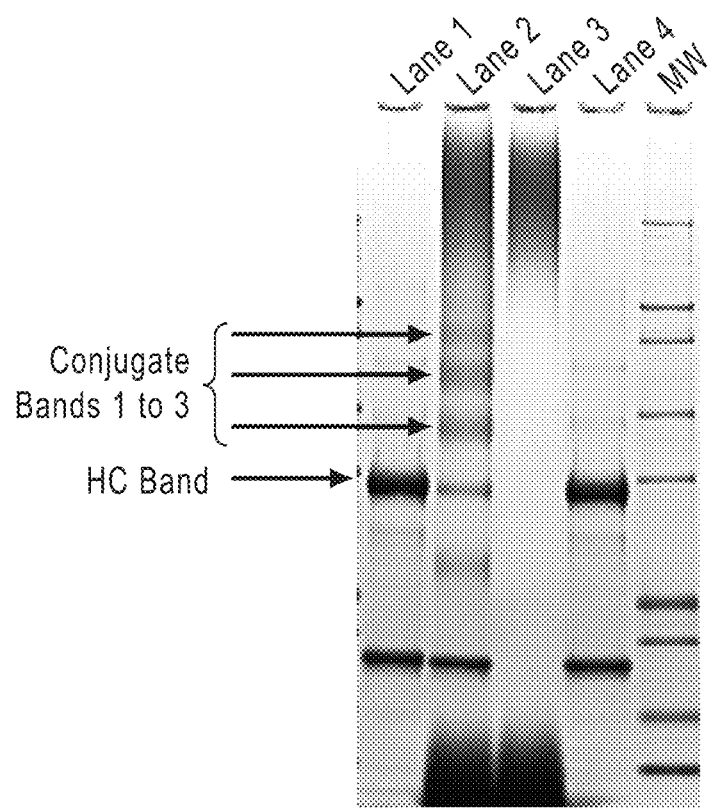
FIG. 16 is a SDS PAGE image for fluorescent particles bearing azide reactive groups upon addition to antibody against human CD4 with DIBO modification, as in Example 36

Antibody-polymer conjugates were analyzed using NUPAGE NOVEX 4-12% Bis-Tris Gels (Thermo Fisher Scientific) in MOPS running buffer. 1 μg antibody from each sample is first incubated with 0.1M dithiothreitol (DTT) at 70° C. for 10 minutes and then applied per lane. After staining with SYPRO Ruby Protein Stain (Thermo Fisher Scientific), the gels were imaged with an FLA-9000 image scanner with an excitation of 473 nm and a 575LP filter (available from Fujifilm Life Science). FIG. 16 shows a PAGE image for an azide functionalized fluorescent NP, similar to Sample 38 in Example 25, upon addition to antibody against human CD4 with DIBO modification. DIBO-modified Ab without the addition of azide functionalized fluorescent NP control (Ab only, lanes 1 and 4); azide functionalized fluorescent NP with addition of DIBO-modified antibody against human CD4 (conjugate, lane 2); azide functionalized fluorescent NP without the addition of DIBO-modified Ab (control (NP only), lane 3).MARK12

Unstained Standard (Thermo Fisher Scientific) was used as the molecular weight standard (MW). As shown in FIG. 16, the antibody heavy chain (HC) band in the gel image (lane 1 and 4) is fainter upon conjugation of the antibody to the fluorescent nanoparticle (lane 2) indicating successful conjugation. In addition, three higher molecular weight bands appear in lane 2, which can be attributed to formation of the antibody-particle conjugates. When running these NPs under reducing conditions in SDS-PAGE the NP amphiphilic shell (PEG-b-PS) can be dissociated from the NP surface due to the applied electric field. Since the antibody is modified with multiple reactive groups, multiple PEG-b-PS polymer chains can be conjugated to the same HC. Therefore, there are three bands because there is one, two or three PEG-b-PS chains per HC. Densitometric quantitation was used to determine that the decrease of free heavy chain (HC) on the antibody resulting from conjugation to the fluorescent nanoparticle was >85%.

Example 37

Figure 17:
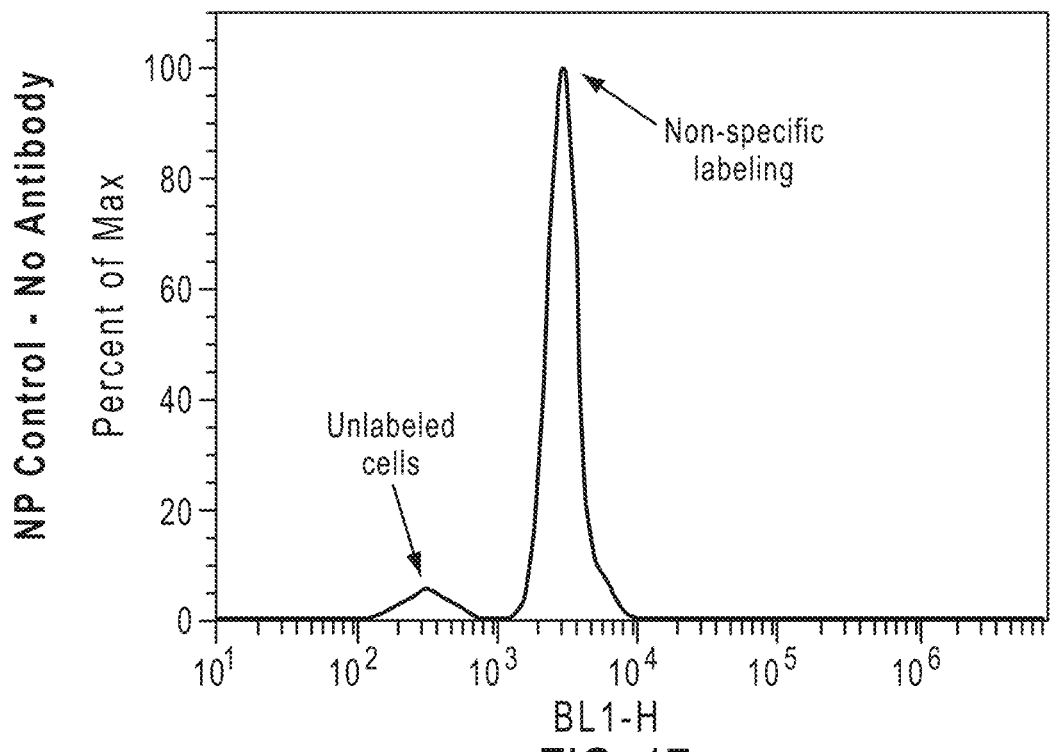
FIG. 17 is a flow cytometry histogram for Sample 44.
Figure 18:
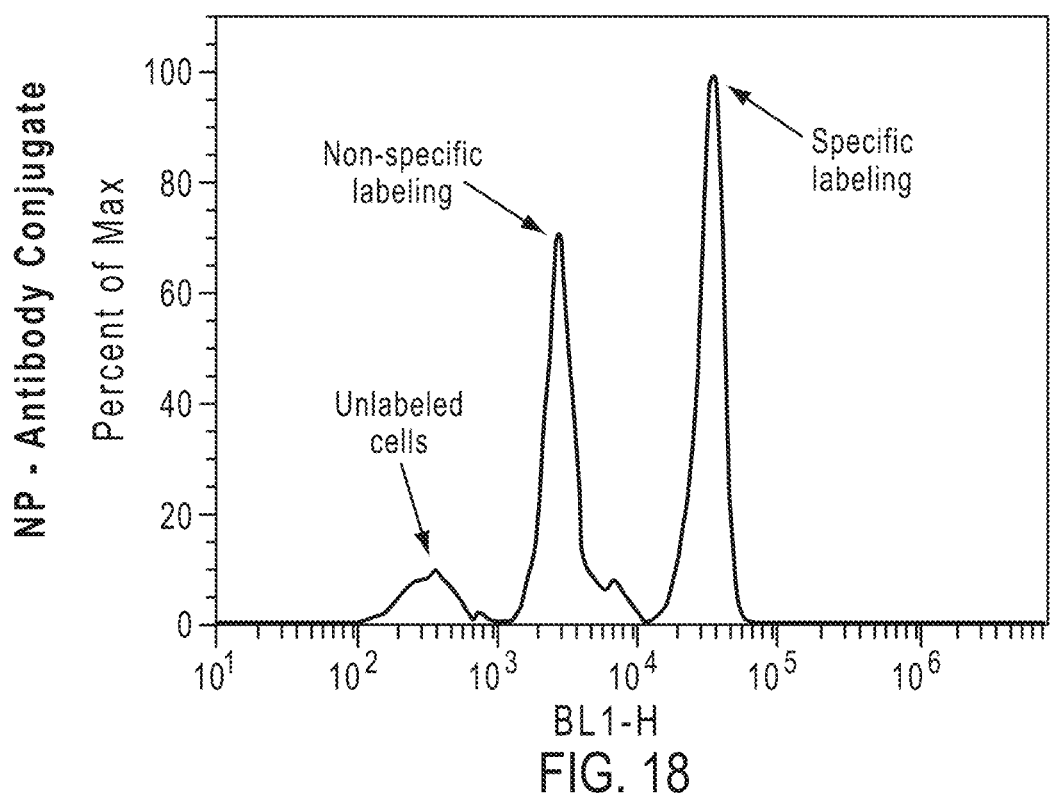
FIG. 18 is a flow cytometry histogram for Sample 44 conjugated to an antibody.
Figure 19:
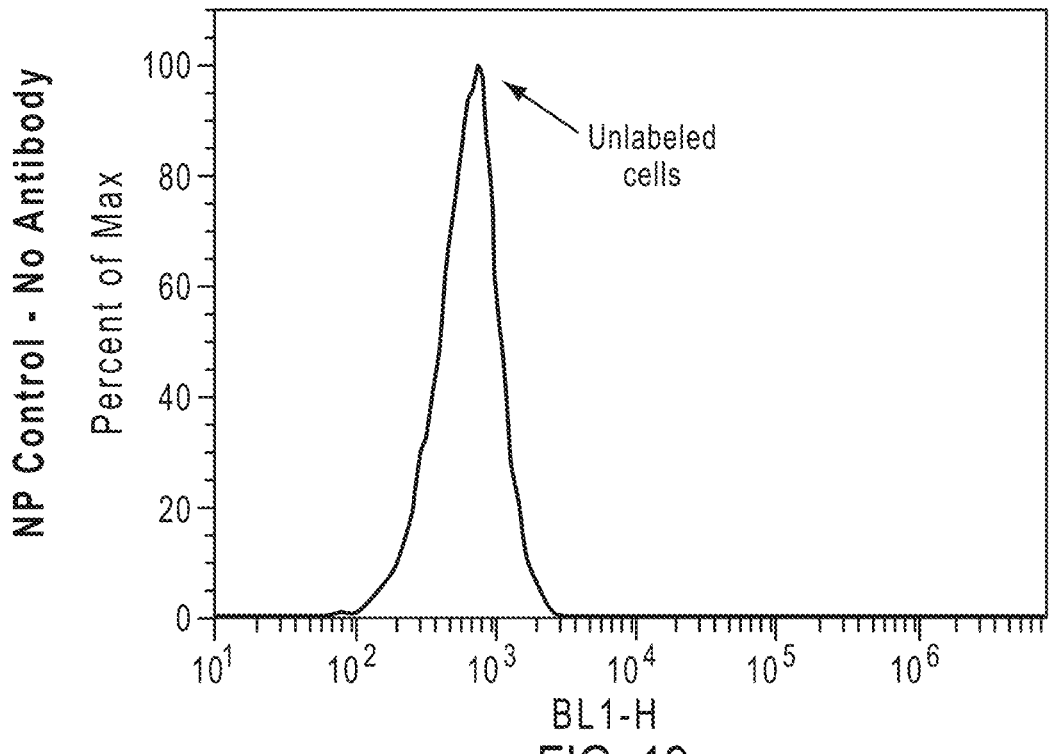
FIG. 19 is a flow cytometry histogram for Sample 31.
Figure 20:
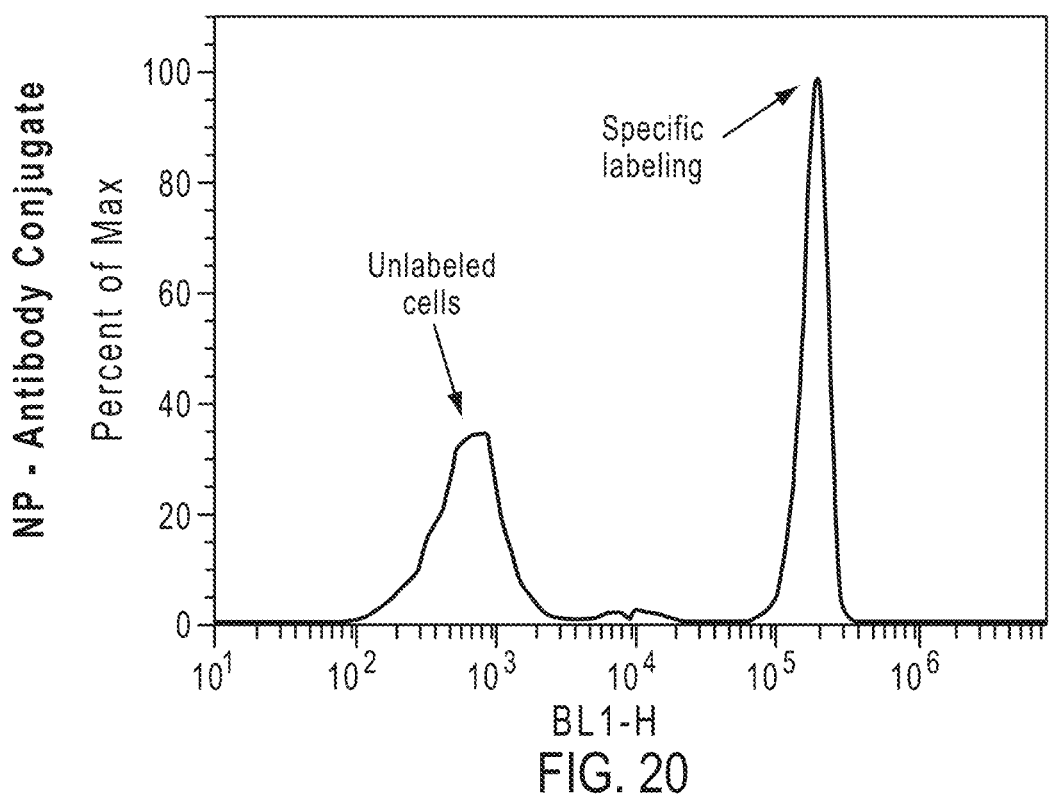
FIG. 20 is a flow cytometry histogram for Sample 31 conjugated to an antibody.

Flow Cytometry Analysis of Fluorescent NPs Loaded with BODIPY Dye and PS-Linked BODIPY Dye This example compares flow cytometry performance of a BODIPY dye that is loaded directly into a NP and a BODIPY dye that is first covalently attached to PS prior to NP formulation. NPs loaded with hydrophobic small molecule dye resulted in unwanted background fluorescence, while covalently attaching the small molecule dye to PS prior to particle formulation eliminated this background. Azide functional NPs containing 1,3-di-n-propyl BODIPY were formulated as described in Example 22, except free 1,3-di-n-propyl BODIPY was added rather than a PS-dye conjugate. 0.22 mg of 1,3-di-n-propyl BODIPY dye, 3.1 mg of polystyrene (PS) (1700 g/mol) (Polymer Source), 4.43 mg of PS-b-PEG ($M_n$=3900 g/mol) copolymer and 2.27 mg of azide functional PS-b-PEG ($M_n$=6600 g/mol) copolymer (prepared as described in Example 29) were dissolved in 1 mL THF/DMSO mixture that was 50/50 by volume and formulated as described in Example 22 with a HD of 45 nm and PdI of 0.05 as determined by DLS (Sample 44). Azide functional fluorescent nanoparticles using PS-dye conjugate Polymer 18 were prepared according to the methods described in Example 22 (Sample 31). Both azide functional fluorescent particles were conjugated as described in Example 29 to DIBO modified mouse monoclonal antibody against human CD4. White blood cells were prepared from lysed whole blood, stained with fluorescent NPs and analyzed by flow cytometry as described in Example 35. For CD4 specific staining, 10,000 lymphocyte events were collected, and an excitation laser source of 488 nm (blue laser) was used with a bandpass filter of 515 to 545 nm. Collected data was represented as histograms. The histogram for cells treated with only NPs (no antibody present) were used as a control and is shown in FIG. 17, where the y axis represents the percent of maximum cell count and the x axis represents the fluorescence intensity as measured using a blue laser as channel 1 (BL1-H). The histogram for cells treated with NP-antibody CD4 conjugates is shown in FIG. 18. Referring to FIG. 17, the control condition for Sample 44 (free 1,3-di-n-propyl BODIPY dye) exhibited a large amount of non-specific cell labeling. This non-specific binding was also evident even when the NPs were conjugated to monoclonal antibody against human CD4 (FIG. 18). Non-specific labeling can arise when hydrophobic free 1,3-di-n-propyl BODIPY dye partitions from the NPs into lipophilic cellular membranes. Non-specific labeling was eliminated for particles prepared using BODIPY 493/503 conjugated to PS, as described in Example 21, prior to the NP formulation (Sample 31). This is evident for Sample 31, where essentially no non-specific labeling was seen in the control (FIG. 19) or NP-antibody conjugate histograms (FIG. 20). The nominal background signal in FIG. 20 is thought to be due to a very low level of non-specific labeling of the antibody. The elimination of non-specific labeling is attributed to the dye conjugate having a higher hydrophobicity and greater miscibility in the PS core as compared to small molecule dye freely loaded in the NP core. The data demonstrates that multiple dyes can be loaded into particles to maximize brightness by covalently attaching the dyes to a hydrophobic polymer, such as PS, such that non-specific labeling or false positives are eliminated. The approach described herein is particularly effective for fluorescent applications, such as flow cytometry, where there is a need for bright fluorescent reagents that exhibit minimal non-specific labeling to other assay components.

All of the compositions and/or methods and/or processes and/or apparatuses disclosed and claimed herein can be made and executed without undue experimentation in light of the present disclosure. While the compositions and methods of this invention have been described in terms of particular embodiments, it will be apparent to those of skill in the art that variations may be applied to the compositions and/or methods and/or apparatus and/or processes and in the steps or in the sequence of steps of the methods described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope and concept of the invention.

All publications and patent applications mentioned in this specification are herein incorporated by reference to the same extent as if each individual publication or patent application was specifically and individually indicated to be incorporated by reference.

What is claimed is:

1. A water-dispersible fluorescent particle comprising:
   an internal hydrophobic region comprising a mixture of one or more first hydrophobic polymers and one or more second hydrophobic polymers, wherein the first hydrophobic polymer is fluorescent and has a first solubility parameter and the second hydrophobic polymer is non-fluorescent and has a second solubility parameter, and wherein the first and second solubility parameters differ by less than 1 $cal^{1/2}$ $cm^{-3/2}$, wherein the one or more first hydrophobic fluorescent polymers comprises a non-fluorescent, hydrophobic polymer that is linked to one or more first organic dyes; and
   an external region encapsulating the internal hydrophobic region, wherein the external region comprises one or more amphiphilic block copolymers, wherein each of the one or more amphiphilic block copolymers comprises at least one hydrophobic block segment embedded in the internal hydrophobic region and at least one hydrophilic block segment that renders the particle dispersible in water, wherein the hydrophobic block has a solubility parameter that differs from the first and second solubility parameters by less than 1 $cal^{1/2}$ $cm^{-3/2}$, wherein the one or more first hydrophobic polymers, the one or more second hydrophobic polymers, and the hydrophobic block segment of the one or more amphiphilic copolymers comprise a monomer residue having a structure of the formula, —[Ar]n-, wherein Ar is an aryl or heteroaryl and is optionally substituted with one or more optionally substituted substituents selected from halogen, hydroxyl, C1-C12 alkyl, C2-C12 alkene, C2-C12 alkyne, C3-C12 cycloalkyl, C1-C12 haloalkyl, C1-C12 alkoxy, C2-C18(hetero)aryloxy, and C2-C18 (hetero)arylamino.

2. The particle of claim 1, wherein the solubility parameter for the one or more first hydrophobic polymer and/or the one or more second hydrophobic polymer has a solubility parameter from about 8.0 $cal^{1/2}cm^{-3/2}$ to 10.0 $cal^{1/2}cm^{-3/2}$.

3. The particle of claim 1, wherein the one or more non-fluorescent polymers and/or the one or more fluorescent polymers has a number average molecular weight ($M_n$) of about 1000 g/mol to about 10,000 g/mol.

4. The particle of claim 1, wherein the first hydrophobic polymer and/or the second hydrophobic polymer comprises a hydrophobic segment with a monomer unit having the same composition as the monomer unit of the hydrophobic segment of the one or more amphiphilic polymers.

5. The particle of claim 1, wherein the weight ratio of the one or more first fluorescent, hydrophobic polymers to the one or more second non-fluorescent hydrophobic polymers in the internal region is about 1:10 to about 10:1.

6. The particle of claim 1, wherein the one or more second hydrophobic polymers is selected from the group consisting of poly(alkyl methacrylates), poly(alkyl acrylates), poly (alkyl methacrylamides), poly(alkyl acrylamides), polystyrene, alkyl substituted polystyrenes, wherein alkyl is selected from $C_{1-10}$ alkyl (e.g., methyl-dodecyl), polylactic acid, polycaprolactone, and poly(vinyl acetate).

7. The particle of claim 1, wherein the mean hydrodynamic diameter of the particle is about 20 nm to about 100 nm as measured by dynamic light scattering (DLS).

8. A conjugate, comprising a fluorescent particle of claim 1 linked to a biomolecule selected from the group consisting of an amino acid, peptide, protein, polysaccharide, nucleoside, nucleotide, nucleic acid base, oligonucleotide, and a nucleic acid polymer, wherein the conjugate is optionally dissolved in an aqueous medium.

9. The particle of claim 1, wherein the at least one hydrophilic segment of the one or more amphiphilic polymers comprises a group selected from PEO, poly(acrylamide), poly(N-2-hydroxypropylmethacrylamide, poly(N,N-dimethylacrylamide), PVA, PVP, poly(N-methyl methacrylamide), PVA, PVP, poly(2-ethyl-2-oxazoline), polyzwitterionic groups, vinyl polymers, acrylic polymers ($CR(X)$—$CH_2$), where X is H, C1-C2 alkyl, or CN and R is $COOR^1$ or $CONR^1R^2$, wherein $R^1$ and $R^2$ are independently H, C1-C2 alkyl alcohols, and combinations thereof.

10. The particle of claim 1, wherein the at least one hydrophobic segment of the one or more amphiphilic polymers comprises a group selected from polystyrene, alkyl methacrylates, alkyl acrylates, alkyl methacrylamides, alkyl acrylamides, alkyl substituted polystyrene, wherein alkyl is selected from $C_{1-10}$ alkyl (e.g., methyl-dodecyl), polylactic acid, polycaprolactone, and poly(vinyl acetate).

11. The particle of claim 1, wherein the one or more amphiphilic polymer is a copolymer of a polyethylene glycol or a polyethylene oxide monomer with a monomer selected from the group consisting of acrylamide, polylactic acid, and styrene monomers.

12. The particle of claim 1, wherein the one or more first hydrophobic polymers and/or the one or more second hydrophobic polymers comprises a monomer residue of a vinyl aromatic compound.

13. The particle of claim 12, wherein the vinyl aromatic compound is a styrene compound that is optionally substituted with an alkyl, aryl, halogen, or haloalkyl group.

14. The particle of claim 1, wherein the one or more organic dyes are selected from the group consisting of boron dipyrromethenes (BODIPY) dyes, cyanines, xanthenes, sulfonated pyrenes, rhodamines, sulfonated rhodamines, coumarins, and derivatives thereof.

15. The particle of claim 14, further comprising a third hydrophobic polymer, wherein the third hydrophobic polymer comprises a non-fluorescent, hydrophobic polymer that is linked to one or more second organic dyes, wherein the one or more first organic dyes are different from the one or more second organic dyes, wherein the first organic dye and the second organic dye are capable of functioning as a donor-acceptor FRET system.

16. The particle of claim 1, wherein the hydrophobic block of the amphiphilic block copolymer comprise a monomer unit of the same composition as a monomer unit in one or more of the first or second hydrophobic polymers.

* * * * *

UNITED STATES PATENT AND TRADEMARK OFFICE
CERTIFICATE OF CORRECTION

PATENT NO. : 11,193,057 B2
APPLICATION NO. : 16/324730
DATED : December 7, 2021
INVENTOR(S) : Adam York et al.

Page 1 of 1

It is certified that error appears in the above-identified patent and that said Letters Patent is hereby corrected as shown below:

In the Drawings

FIG. 14, and on the title page, the illustrative print figure, delete "Fluroescent NP-Antibody" and insert -- Fluorescent NP-Antibody --, therefor.

FIG. 14, and on the title page, the illustrative print figure, delete "Fluroescent NP" and insert -- Fluorescent NP --, therefor.

Signed and Sealed this
Fourteenth Day of October, 2025

John A. Squires
*Director of the United States Patent and Trademark Office*